US011053523B2

(12) United States Patent
Ozaki

(10) Patent No.: US 11,053,523 B2
(45) Date of Patent: Jul. 6, 2021

(54) METHOD OF PRODUCING LIPID

(71) Applicant: Kao Corporation, Tokyo (JP)

(72) Inventor: Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/323,847

(22) PCT Filed: Aug. 28, 2017

(86) PCT No.: PCT/JP2017/030759
§ 371 (c)(1),
(2) Date: Feb. 7, 2019

(87) PCT Pub. No.: WO2018/047657
PCT Pub. Date: Mar. 15, 2018

(65) Prior Publication Data

US 2019/0169659 A1 Jun. 6, 2019

(30) Foreign Application Priority Data

Sep. 7, 2016 (JP) ............................ JP2016-174752

(51) Int. Cl.
*C12P 7/64* (2006.01)
*C12N 9/02* (2006.01)

(52) U.S. Cl.
CPC .............. *C12P 7/64* (2013.01); *C12N 9/0071* (2013.01)

(58) Field of Classification Search
None
See application file for complete search history.

(56) References Cited

U.S. PATENT DOCUMENTS 6,136,574 A * 10/2000 Knutzon ................. A23L 33/40 435/134
8,709,766 B2 * 4/2014 Radakovits ............ C12N 15/79 435/134
10,337,037 B2 * 7/2019 Ozaki ................ C12N 15/8247
2009/0104674 A1 * 4/2009 Yadav .................. C12N 9/1029 435/134
2012/0277417 A1 11/2012 Kilian et al.
2015/0104875 A1 4/2015 Kilian et al.

FOREIGN PATENT DOCUMENTS

JP 2014-519810 A 8/2014
WO WO 2012/052468 A2 4/2012
WO WO 2012/149457 A2 11/2012
WO WO 2018/062015 4/2018

OTHER PUBLICATIONS

Kaye et al.,"Metabolic engineering toward enhanced LC-PUFA biosynthesis in Nannochloropsis oceanica: Overexpression of endogenous delta12 desaturase driven by stress-inducible promoter leads to enhanced deposition of polyunsaturated fatty acids in TAG", Algal Research 11: 387-398 (2015) (Year: 2015).*

Ma et al.,"Lipid Production from Nannochloropsis" Marine Drugs 14,61, pp. 1-18 (Mar. 2016) (Year: 2016).*

International Search Report (ISR) for PCT/JP2017/030759; I.A. fd Aug. 28, 2017, dated Nov. 28, 2017 from the Japan Patent Office, Tokyo, Japan.

International Preliminary Report on Patentability (IPRP), Chapter I of the Patent Cooperation Treaty, including the Written Opinion for PCT/JP2017/030759; I.A. fd Aug. 28, 2017, dated Mar. 12, 2019, by the International Bureau of WIPO, Geneva, Switzerland.

Kaye, Y et al., "Metabolic engineering toward enhanced LC-PUFA biosynthesis in *Nannochloropsis oceanica*: Overexpression of endogenous Δl2 desaturase driven by stress-inducible promoter leads to enhanced deposition of polyunsaturated fatty acids in TAG," Algal research 2015 v.11 pp. 387-398, Available online Jun. 2, 2015.

Ma, X et al., "Cloning and characterization of a delta-6 desaturase encoding gene from *Nannochloropsis oculata*," Chinese J Oceanology and Limnology 29(2):290-296 (2011), First Online: Mar. 2, 2011, doi.org/10.1007/s00343-011-0048-0.

Ma, X et al., Accession No: E0YDP2, Definition: Delta-6 desaturase, Nannochloropsis oculata, Uniprot [online], Nov. 2, 2010, sequence version 1; (entry version 23, Oct. 25, 2017) <IRL:www.uniprot.org/uniprot/E0YDP2.txt?version=1> [retrieved on Nov. 13, 2017].

Poliner, E. et al., "A toolkit for Nannochloropsis oceanica CCMP1779 enables gene stacking and genetic engineering of the eicosapentaenoic acid pathway for enhanced long-chain polyunsaturated fatty acid production." Plant Biotechnol J. Jan. 2018;16(1):298-309. doi: 10.1111/pbi.12772. Epub Jul. 13, 2017. PMID: 28605577; PMCID: PMC5785352.

* cited by examiner

*Primary Examiner* — Anand U Desai
(74) *Attorney, Agent, or Firm* — Sterne, Kessler, Goldstein & Fox P.L.L.C.

(57) ABSTRACT

A method of producing lipids, containing the steps of:

culturing an alga belonging to the genus *Nannochloropsis*; and producing fatty acids or lipids containing the same as components;

wherein expressions of genes encoding a Δ12-desaturase and a Δ6-desaturase are enhanced in the alga; and a transformant of an alga belonging to the genus *Nannochloropsis*, wherein expressions of genes encoding a Δ12-desaturease and a Δ6-desaturease are enhanced.

23 Claims, 1 Drawing Sheet

Specification includes a Sequence Listing.

METHOD OF PRODUCING LIPID

TECHNICAL FIELD

The present invention relates to a method of producing lipids. Further, the present invention also relates to a transformant for use in this method.

BACKGROUND ART

Fatty acids are one of the principal components of lipids. In vivo, fatty acids are bonded to glycerin via an ester bond to form lipids such as triacylglycerol. Further, many animals and plants also store and utilize fatty acids as energy sources. These fatty acids and lipids stored in animals and plants are widely utilized for food or industrial use.

For example, long-chain fatty acids having 18 or more carbon atoms are different in chemical properties depending on the number of carbon atoms or a degree of unsaturation, and used in various applications. For example, most of long-chain polyunsaturated fatty acids (hereinafter, also referred to as "PUFA") such as eicosapentaenoic acid (hereinafter, also referred to as "EPA") and docosahexaenoic acid (hereinafter, also referred to as "DHA") are known to be essential fatty acids which are unable to be synthesized in vivo in animals. Therefore, such PUFA is particularly useful in nutritional use and utilized as physiologically functional food and the like.

Generally, a fatty acid synthetic pathway of plants is localized in the chloroplast. In the chloroplast, an elongation reaction of the carbon chain is repeated starting from an acetyl-acyl-carrier-protein (acyl-carrier-protein, hereinafter, also referred to as "ACP"), and finally an acyl-ACP (a composite consisting of an acyl group being a fatty acid residue and an ACP. Here, the number of carbon atoms indicates the number of carbon atoms of the acyl group, and indicates the same hereinafter in several cases) having about 18 carbon atoms is synthesized. A β-ketoacyl-acyl-carrier-protein synthase (hereinafter, also referred to as "KAS") is an enzyme involved in control of chain length of the acyl group, among enzymes involved in the fatty acid synthetic pathway. In plants, four kinds of KASs having different function respectively, namely KAS I, KAS II, KAS III and KAS IV are known to exist. Among them, KAS II is mainly involved in the elongation reaction to the stearoyl-ACP having 18 carbon atoms.

Synthesized acyl-ACP is converted into free fatty acids by acyl-ACP thioesterase (hereinafter, also referred to simply as "TE"), and the resultant products are delivered to an endoplasmic reticulum. Then, on the endoplasmic reticulum, PUFA is synthesized by a multistep reaction in which free fatty acids, acyl-CoA, or an ester compound between fatty acids and glycerol is used as a substrate, and a great number of desaturases or elongases act thereon.

In recent years, researches and developments on renewable energy have been promoted toward realization of a sustainable society. In particular, photosynthetic microorganisms are expected as biofuel organisms without competing with grain in addition to an effect on reducing carbon dioxide.

Especially, among them, algae attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and lipid accumulation ability in comparison with plants. Research has started on a lipid synthesis and accumulation mechanism of the algae and lipid production technologies applied by the lipid productivity or lipid accumulation ability of algae, but unclear parts remain in many respects.

As mentioned above, fatty acids are widely used in various applications. Therefore, attempts have been made on improving productivity of the fatty acids or the lipids in vivo by using hosts such as plants or bacteria. Furthermore, applications and usefulness of the fatty acids depend on the number of carbon atoms (chain length) or unsaturated bonds (degree of unsaturation) thereof. Therefore attempts have been made also on controlling the number of carbon atoms or unsaturated bonds of the fatty acids.

In general, enhancement of desaturase is considered to be effective in improving the productivity of PUFA, and these enzyme groups have been identified from various organisms. For example, desaturase derived from algae belonging to the genus *Nannochloropsis*, on which attention is focused as a next-generation production source for fats and oils, is known to be usable for synthesis of PUFA (see Patent Literature 1, Non-Patent Literature 1 and 2).

Thus, a method of effectively producing the lipids rich in desired PUFA in oleaginous organisms is in demand in the technical field.

CITATION LIST

Patent Literatures

Patent Literature 1: WO 2012/149457

Non-Patent Literatures

Non-Patent Literature 1: Algal Research, 2015, Vol. 11, p. 387-398

Non-Patent Literature 2: Chinese Journal of Oceanology and Limnology, 2011, Vol. 29(2), p. 290-296

SUMMARY OF INVENTION

The present invention relates to a method of producing lipids, containing the steps of:

culturing an alga belonging to the genus *Nannochloropsis*; and producing fatty acids or lipids containing the same as components;

wherein expressions of a Δ12-desaturase and a Δ6-desaturase are enhanced in the alga.

Further, the present invention relates to a method of modifying the composition of fatty acids, containing the steps of:

enhancing expressions of genes encoding a Δ12-desaturase and a Δ6-desaturase in an alga belonging to the genus *Nannochloropsis*; and increasing the proportion of long-chain polyunsaturated fatty acids in the whole fatty acids to be produced in a cell of the alga.

Furthermore, the present invention relates to a transformant of an alga belonging to the genus *Nannochloropsis*, wherein expressions of a Δ12-desaturase and a Δ6-desaturase are enhanced.

Other and further features and advantages of the present invention will appear more fully from the following description, appropriately referring to the accompanying drawings.

MODE FOR CARRYING OUT THE INVENTION

Figure 1:
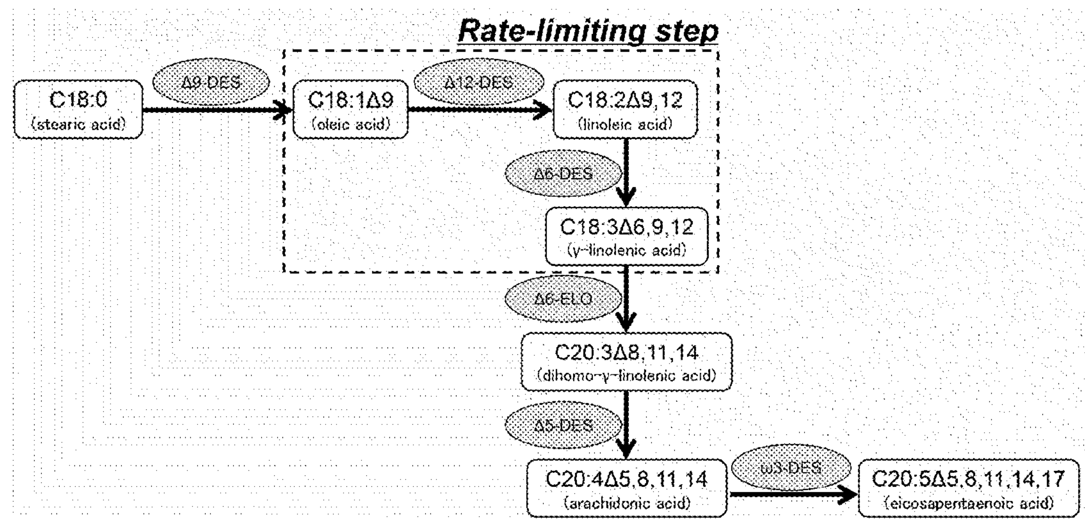
FIG. 1 is a diagram showing a principal pathway of EPA synthesis in algae belonging to the genus *Nannochloropsis*, and a rate-limiting step in synthesis of PUFA such as EPA.

The present invention provides a method of producing lipids, which improves productivity of PUFA or lipids containing the same as components.

Further, the present invention provides a transformant in which the productivity of PUFA or lipids containing the same as components is improved.

The present inventor diligently conducted study on the aforesaid points.

Algae belonging to the genus *Nannochloropsis* are excellent in productivity of PUFA such as EPA. Moreover, production amount of total fatty acids is significantly increased in late culture phase of the algae (specifically, conditions in which a nutrient source such as nitrogen is exhausted). However, the present inventor conducted a detailed study on the PUFA productivity of algae belonging to the genus *Nannochloropsis*, and as a result, found that as culture period becomes longer and production amount of total fatty acids increases, ratio of production amount of PUFA to production amount of total fatty acids significantly decreases.

So the present inventor first conducted a study on a pathway of PUFA synthesis in the algae belonging to the genus *Nannochloropsis* in various ways, and tried to identify the synthesis pathway. The present inventor continued to conduct further studies on a rate-limiting reaction in synthesis of PUFA, and as a result, found that a series of steps in which linoleic acid (hereinafter, also denoted as "C18:2Δ9,12") is formed from oleic acid (hereinafter, also denoted as "C18:1Δ9") by action of Δ12-desaturase being one kind of desaturases, and γ-linolenic acid (hereinafter, also denoted as "C18:3Δ6,9,12") is formed from C18:2Δ9,12 formed by action of Δ6-desaturase also being one kind of desaturase are rate-limiting steps in PUFA synthesis. Then, the present inventor found that the production amount of PUFA is significantly increased by enhancing expression of an enzyme that catalyzes a reaction in the rate-limiting step.

The present invention was completed based on these findings.

According to the present invention, the expression of the enzyme that catalyzes the reaction in the rate-limiting step of a PUFA synthetic pathway is enhanced, and the production amount of PUFA can be increased.

According to the method of producing the lipids of the present invention, the productivity of PUFA or lipids containing the same as components can be improved.

Moreover, a transformant of the present invention is enhanced in the expression of the enzyme that catalyzes the reaction in the rate-limiting step of the PUFA synthetic pathway, and is excellent in productivity of PUFA or lipids containing the same as components.

The term "lipid(s)" in the present specification, covers a simple lipid such as a neutral lipid (monoacylglycerol (MAG), diacylglycerol (DAG), triacylglycerol, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, a part of the fatty acids or a part of the acyl group in molecules of a simple lipid and a complex lipid is expressed as "fatty acid residue". Then, unless otherwise specified, a term "fatty acid" is used as a generic term for "free fatty acid" and "fatty acid residue".

Moreover, a term "fatty acids or lipids containing the same as components" in the present specification is generically used including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above regarding as fatty acids. The weight (production amount) of the fatty acids or the fatty acid composition can be measured according to the method used in Examples.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH7.0), 0.5% SDS, 5×Denhardt and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

Figure 2:
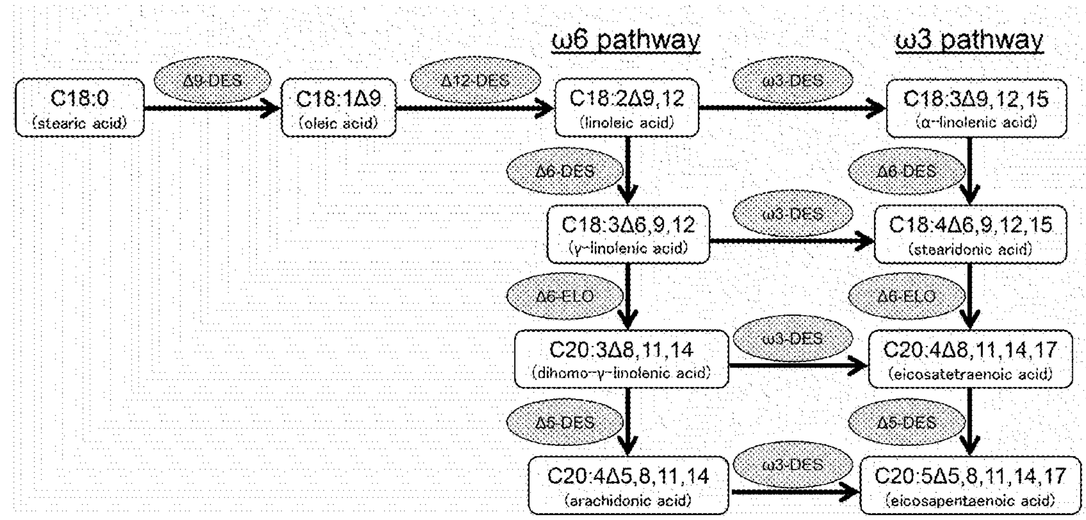
FIG. 2 is a diagram showing a general pathway of PUFA synthesis in algae or plants.

As stated above, the present inventor identified the main pathway of PUFA synthesis in algae belonging to the genus *Nannochloropsis*. The principal pathway of PUFA synthesis identified in this study, and the rate-limiting step in the synthesis of PUFA, are shown in FIG. 1. In addition, for reference, a general pathway of PUFA synthesis in algae or plants is shown in FIG. 2.

As shown in Examples described later, in wild type algae belonging to the genus *Nannochloropsis*, C20:4 is detected, but stearidonic acid (hereinafter, also denoted as "C18:4Δ6,9,12,15") is hardly detected. From these results, main pathway of EPA synthesis in the algae belonging to the genus *Nannochloropsis* was identified as pathway through arachidonic acid (hereinafter, also denoted as "C20:4Δ5,8,11,14") as shown in FIG. 1.

Moreover, the present inventor identified various desaturases derived from the algae belonging to the genus *Nannochloropsis*. In addition, the present inventor enhanced the expression of each of the desaturases and measured production amount of PUFA such as EPA. The result was that no significant change in amount of PUFA was observed even if expression of each desaturase was enhanced individually.

Accordingly, the present inventor conducted a further study on the pathway of PUFA synthesis in algae belonging to the genus *Nannochloropsis*. As a result, the present inventor found that the series of steps in which a reaction is catalyzed by Δ12-desaturase (hereinafter, also referred to as "Δ12-DES") and Δ6-desaturase (hereinafter, also referred to as "Δ6-DES") (the reactions in which linoleic acid is formed from oleic acid, and γ-linolenic acid is formed from the formed linoleic acid) are the rate-limiting step of the pathway of PUFA synthesis in algae belonging to the genus *Nannochloropsis*. So the PUFA productivity of algae belonging to the genus *Nannochloropsis* is improved by enhancing the expression of the enzyme that catalyzes the reaction in the rate-limiting step. Further, with elapse of algae culture time, ratio of amount of PUFA to amount of total fatty acids is significantly improved in comparison with that in a wild type strain.

The term "rate-limiting step" in the present specification means a step which, when a dynamic process such as a chemical reaction or a complicated metabolic pathway is formed of several steps, progresses more slowly than other steps among the steps so as to substantially dominate progress of the entire process.

In the present specification, the term "Δ12-DES" means a protein (enzyme) that catalyzes a reaction of introducing an unsaturated bond into a 012-position of 018:1θ9 to produce C18:2Δ,9,12 being ω-6 fatty acid. Then, in the present specification, the term "Δ12-desaturase activity" (hereinafter, also referred to as "Δ12-DES activity") means activity for introducing the unsaturated bond into the Δ12-position of C18:1Δ9.

It can be confirmed that the protein has the Δ12-DES activity by a system using a Δ12-DES gene deletion strain, for example. Alternatively, it can also be confirmed by examining formation of linoleic acid by introducing the DNA of which a gene encoding the above-described protein was ligated downstream of a promoter functioning inside a host cell, into the Δ12-DES gene deletion strain. Alternatively, it can also be confirmed by measuring a decrease of oleic acid amount or an increase of linoleic acid amount according to an ordinary method by preparing the Δ12-DES or cell lysate containing the same to react the resultant material with the reaction solution containing oleic acid, oleoyl-CoA, or the like.

Preferred examples of the Δ12-DES in the present invention include the following proteins (A) to (D):

(A) a protein consisting of the amino acid sequence set forth in SEQ ID NO: 1;

(B) a protein consisting of an amino acid sequence having 60% or more identity with the amino acid sequence of the protein (A), and having Δ12-desaturase activity;

(C) a protein consisting of the amino acid sequence set forth in SEQ ID NO: 45; and (D) a protein consisting of an amino acid sequence having 60% or more identity with the amino acid sequence of the protein (C), and having Δ12-desaturase activity.

The protein consisting of the amino acid sequence set forth in SEQ ID NO: 1 is a Δ12-DES derived from *Nannochloropsis oculata* strain NIES-2145 being algae belonging to the genus *Nannochloropsis* (hereinafter, also referred to as "NoΔ12-DES"). Further, the protein consisting of the amino acid sequence set forth in SEQ ID NO: 45 is a Δ12-DES derived from *Nannochloropsis gaditana* B-31 strain being algae belonging to the genus *Nannochloropsis* (hereinafter, also referred to as "NgΔ12-DES").

Note that, identity of the amino acid sequence of the protein (A) with the amino acid sequence of the protein (C) is 86%.

All of the proteins (A) to (D) have Δ12-DES activity.

In the protein (B), the identity with the amino acid sequence of the protein (A) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ12-DES activity. Further, specific examples of the protein (B) include a protein in which 1 or several (for example 1 or more and 176 or less, preferably 1 or more and 154 or less, more preferably 1 or more and 132 or less, further preferably 1 or more and 110 or less, furthermore preferably 1 or more and 88 or less, furthermore preferably 1 or more and 66 or less, furthermore preferably 1 or more and 44 or less, furthermore preferably 1 or more and 36 or less, furthermore preferably 1 or more and 22 or less, furthermore preferably 1 or more and 9 or less, and furthermore preferably 1 or more and 5 or less) amino acids are deleted, substituted, inserted or added to the amino acid sequence of the protein (A).

In the protein (D), the identity with the amino acid sequence of the protein (C) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ12-DES activity. Further, specific examples of the protein (D) include a protein in which 1 or several (for example 1 or more and 181 or less, preferably 1 or more and 159 or less, more preferably 1 or more and 136 or less, further preferably 1 or more and 113 or less, furthermore preferably 1 or more and 91 or less, furthermore preferably 1 or more and 68 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less) amino acids are deleted, substituted, inserted or added to the amino acid sequence of the protein (C).

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the desired activity is kept and a part of the amino acid sequence is subjected to mutation.

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR reaction, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, an objective gene can also be obtained by introducing a genetic mutation at random, and then performing an evaluation of the enzyme activities and a gene analysis thereof by an appropriate method.

The proteins (A) to (D) can be obtained by chemical techniques, genetic engineering techniques or the like that are ordinarily carried out. For example, a natural product-derived protein can be obtained through isolation, purification and the like from *Nannochloropsis oculata* or *Nannochloropsis gaditana*. In addition, the proteins (A) to (D) can be obtained by artificial chemical synthesis based on the amino acid sequence set forth in SEQ ID NO: 1 or 45. Alternatively, as recombinant proteins, proteins (A) to (D) may also be prepared by gene recombination technologies. In the case of preparing a recombinant protein, a gene encoding the Δ12-DES described below can be used.

Note that the algae such as *Nannochloropsis oculata* can be obtained from culture collection such as private or public research institutes or the like. For example, *Nannochloropsis oculata* strain NIES-2145 can be obtained from National Institute for Environmental Studies (NIES).

An example of the gene encoding the Δ12-DES (preferably, any one of the proteins (A) to (D)) (hereinafter, also referred to as "Δ12-DES gene") includes a gene consisting of any one of the following DNAs (a) to (d).

(a) a DNA consisting of the nucleotide sequence set forth in SEQ ID NO: 2;

(b) a DNA consisting of a nucleotide sequence having 60% or more identity with the nucleotide sequence of the DNA (a), and encoding a protein having Δ12-DES activity;

(c) a DNA consisting of the nucleotide sequence set forth in SEQ ID NO: 6; and (d) a DNA consisting of a nucleotide sequence having 60% or more identity with the nucleotide sequence of the DNA (c), and encoding a protein having Δ12-DES activity.

The nucleotide sequence set forth in SEQ ID NO: 2 is a nucleotide sequence of a gene encoding the protein (NoΔ12-DES) consisting of the amino acid sequence set forth in SEQ ID NO: 1 (hereinafter, also referred to as "NoΔ12-DES gene").

The nucleotide sequence set forth in SEQ ID NO: 46 is a nucleotide sequence of a gene encoding the protein (NgΔ12-DES) consisting of the amino acid sequence set forth in SEQ ID NO: 45 (hereinafter, also referred to as "NgΔ12-DES gene").

In the DNA (b), the identity with the nucleotide sequence of the DNA (a) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ12-DES activity.

Further, the DNA (b) is also preferably a DNA in which 1 or several (for example 1 or more and 527 or less, preferably 1 or more and 461 or less, more preferably 1 or more and 396 or less, further preferably 1 or more and 330 or less, further preferably 1 or more and 264 or less, further preferably 1 or more and 198 or less, further preferably 1 or more and 132 or less, further preferably 1 or more and 106 or less, further preferably 1 or more and 66 or less, further preferably 1 or more and 27 or less, and furthermore preferably 1 or more and 14 or less) nucleotides are deleted, substituted, inserted or added to the nucleotide sequence of the DNA (a), and encoding a protein having Δ12-DES activity.

Furthermore, the DNA (b) is also preferably a DNA capable of hybridizing with a DNA consisting of the nucleotide sequence complementary with the DNA (a) under a stringent condition, and encoding a protein having Δ12-DES activity.

In the DNA (d), the identity with the nucleotide sequence of the DNA (c) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ12-DES activity.

Further, the DNA (d) is also preferably a DNA in which 1 or several (for example 1 or more and 544 or less, preferably 1 or more and 476 or less, more preferably 1 or more and 408 or less, further preferably 1 or more and 340 or less, further preferably 1 or more and 272 or less, further preferably 1 or more and 204 or less, further preferably 1 or more and 136 or less, further preferably 1 or more and 109 or less, further preferably 1 or more and 68 or less, further preferably 1 or more and 28 or less, and furthermore preferably 1 or more and 14 or less) nucleotides are deleted, substituted, inserted or added to the nucleotide sequence of the DNA (c), and encoding a protein having Δ12-DES activity.

Furthermore, the DNA (d) is also preferably a DNA capable of hybridizing with a DNA consisting of the nucleotide sequence complementary with the DNA (c) under a stringent condition, and encoding a protein having Δ12-DES activity.

In the present specification, the term "Δ6-DES" means a protein (enzyme) that catalyzes a reaction of introducing an unsaturated bond into a Δ6-position of C18:2Δ9,12 to produce C18:3Δ6,9,12. Then, in the present specification, the term "Δ6-desaturase activity" (hereinafter, also referred to as "Δ6-DES activity") means activity for introducing the unsaturated bond into the Δ6-position of C18:2Δ9,12.

It can be confirmed that the protein has the Δ6-DES activity by a system using a Δ6-DES gene deletion strain, for example. Alternatively, it can also be confirmed by examining formation of γ-linolenic acid by introducing the DNA of which a gene encoding the above-described protein was ligated downstream of a promoter functioning inside a host cell, into the Δ6-DES gene deletion strain. Alternatively, it can also be confirmed by measuring a decrease of linoleic acid amount or an increase of γ-linolenic acid amount according to an ordinary method by preparing the Δ6-DES or cell lysate containing the same to react the resultant material with the reaction solution containing linoleic acid, linoleoyl-CoA, or the like.

Preferred examples of the Δ6-DES in the present invention include the following proteins (E) to (H):

(E) a protein consisting of the amino acid sequence set forth in SEQ ID NO: 3;

(F) a protein consisting of an amino acid sequence having 60% or more identity with the amino acid sequence of the protein (E), and having Δ6-desaturase activity;

(G) a protein consisting of the amino acid sequence set forth in SEQ ID NO: 47; and (H) a protein consisting of an amino acid sequence having 60% or more identity with the amino acid sequence of the protein (G), and having Δ6-desaturase activity.

The protein consisting of the amino acid sequence set forth in SEQ ID NO: 3 is a Δ6-DES derived from *Nannochloropsis oculata* strain NIES-2145 (hereinafter, also referred to as "NoΔ6-DES"). Further, the protein consisting of the amino acid sequence set forth in SEQ ID NO: 47 is a Δ6-DES derived from *Nannochloropsis gaditana* B-31 strain (hereinafter, also referred to as "NgΔ6-DES").

Note that, identity of the amino acid sequence of the protein (E) with the amino acid sequence of the protein (G) is 89%.

All of the proteins (E) to (H) have Δ6-DES activity.

In the protein (F), the identity with the amino acid sequence of the protein (E) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-DES activity. Further, specific examples of the protein (F) include a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence of the protein (E).

In the protein (H), the identity with the amino acid sequence of the protein (G) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-DES activity. Further, specific examples of the protein (H) include a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence of the protein (G).

Specific examples of a method for introducing the mutation into the amino acid sequence include the above-mentioned method with regard to the Δ12-DES.

The proteins (E) to (H) can be obtained by chemical techniques, genetic engineering techniques or the like that are ordinarily carried out. For example, a natural product-derived protein can be obtained through isolation, purification and the like from *Nannochloropsis oculata* or *Nannochloropsis gaditana*. In addition, the proteins (E) to (H) can be obtained by artificial chemical synthesis based on the amino acid sequence set forth in SEQ ID NO: 3 or 47. Alternatively, as recombinant proteins, proteins (E) to (H) may also be prepared by gene recombination technologies. In the case of preparing a recombinant protein, a gene encoding the Δ6-DES described below can be used.

An example of the gene encoding the Δ6-DES (preferably, any one of the proteins (E) to (H)) (hereinafter, also referred to as "Δ6-DES gene") includes a gene consisting of any one of the following DNAs (e) to (h).

(e) a DNA consisting of the nucleotide sequence set forth in SEQ ID NO: 4;

(f) a DNA consisting of a nucleotide sequence having 60% or more identity with the nucleotide sequence of the DNA (e), and encoding a protein having Δ6-DES activity;

(g) a DNA consisting of the nucleotide sequence set forth in SEQ ID NO: 48; and (h) a DNA consisting of a nucleotide sequence having 60% or more identity with the nucleotide sequence of the DNA (g), and encoding a protein having Δ6-DES activity.

The nucleotide sequence set forth in SEQ ID NO: 4 is a nucleotide sequence of a gene encoding the protein (NoΔ6-DES) consisting of the amino acid sequence set forth in SEQ ID NO: 3 (hereinafter, also referred to as "NoΔ6-DES gene").

The nucleotide sequence set forth in SEQ ID NO: 48 is a nucleotide sequence of a gene encoding the protein (NgΔ6-DES) consisting of the amino acid sequence set forth in SEQ ID NO: 47 (hereinafter, also referred to as "NgΔ6-DES gene").

In the DNA (f), the identity with the nucleotide sequence of the DNA (e) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-DES activity.

Further, the DNA (f) is also preferably a DNA in which 1 or several (for example 1 or more and 570 or less, preferably 1 or more and 499 or less, more preferably 1 or more and 428 or less, further preferably 1 or more and 357 or less, further preferably 1 or more and 285 or less, further preferably 1 or more and 214 or less, further preferably 1 or more and 143 or less, further preferably 1 or more and 114 or less, further preferably 1 or more and 72 or less, further preferably 1 or more and 29 or less, and furthermore preferably 1 or more and 15 or less) nucleotides are deleted, substituted, inserted or added to the nucleotide sequence of the DNA (e), and encoding a protein having Δ6-DES activity.

Furthermore, the DNA (f) is also preferably a DNA capable of hybridizing with a DNA consisting of the nucleotide sequence complementary with the DNA (e) under a stringent condition, and encoding a protein having Δ6-DES activity.

In the DNA (h), the identity with the nucleotide sequence of the DNA (g) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-DES activity.

Further, the DNA (h) is also preferably a DNA in which 1 or several (for example 1 or more and 572 or less, preferably 1 or more and 500 or less, more preferably 1 or more and 429 or less, further preferably 1 or more and 357 or less, further preferably 1 or more and 286 or less, further preferably 1 or more and 215 or less, further preferably 1 or more and 143 or less, further preferably 1 or more and 115 or less, further preferably 1 or more and 72 or less, further preferably 1 or more and 29 or less, and furthermore preferably 1 or more and 15 or less) nucleotides are deleted, substituted, inserted or added to the nucleotide sequence of the DNA (g), and encoding a protein having Δ6-DES activity.

Furthermore, the DNA (h) is also preferably a DNA capable of hybridizing with a DNA consisting of the nucleotide sequence complementary with the DNA (g) under a stringent condition, and encoding the protein having Δ6-DES activity.

In the present invention, it is preferred to also enhance expression of an ω3-desaturase (hereinafter, also referred to as "ω3-DES"), in addition to the Δ12-DES and the Δ6-DES.

In the present specification, the term "ω3-DES" means a protein (enzyme) that catalyzes a reaction of introducing an unsaturated bond into an ω3-position of C20:4Δ5,8,11,14 to form EPA (hereinafter, also denoted as "C20:5Δ5,8,11,14, 17") being ω-3 fatty acid, as shown in FIG. 1. Then, in the present specification, the term "ω3-desaturase activity" (hereinafter, also referred to as "ω3-DES activity") means activity for introducing the unsaturated bond into the ω3-position of C20:4Δ5,8,11,14.

As shown in Examples described later, in the algae belonging to the genus *Nannochloropsis*, in which expressions of the Δ12-DES and the Δ6-DES are enhanced, introduction of an unsaturated bond into the ω3-position of C20:4Δ5,8,11,14 is accelerated by enhancing expression of the ω3-DES also, and production amount of C20:5Δ5,8,11, 14,17 is further increased.

It can be confirmed that the protein has the ω3-DES activity by a system using an ω3-DES gene deletion strain, for example. Alternatively, it can also be confirmed by examining formation of EPA by introducing the DNA of which a gene encoding the above-described protein was ligated downstream of a promoter functioning inside a host cell, into the ω3-DES gene deletion strain. Alternatively, it can also be confirmed by measuring a decrease of arachidonic acid amount or an increase of EPA amount according to an ordinary method by preparing the ω3-DES or cell lysate containing the same to react the resultant material with the reaction solution containing arachidonic acid derivatives (the thioester compound with CoA, the ester compound with glycerol, or the like).

Preferred examples of the ω3-DES in the present invention include the following proteins (I) to (L):

(I) a protein consisting of the amino acid sequence set forth in SEQ ID NO: 5;

(J) a protein consisting of an amino acid sequence having 60% or more identity with the amino acid sequence of the protein (I), and having ω3-desaturase activity;

(K) a protein consisting of the amino acid sequence set forth in SEQ ID NO: 49; and (L) a protein consisting of an amino acid sequence having 60% or more identity with the amino acid sequence of the protein (K), and having ω3-desaturase activity.

The protein consisting of the amino acid sequence set forth in SEQ ID NO: 5 is an ω3-DES derived from *Nannochloropsis oculata* strain NIES-2145 (hereinafter, also referred to as "Noω3-DES"). Further, the protein consisting of the amino acid sequence set forth in SEQ ID NO: 49 is an ω3-DES derived from *Nannochloropsis gaditana* CCMP526 strain (hereinafter, also referred to as "Ngω3-DES").

Note that, identity of the amino acid sequence of the protein (I) with the amino acid sequence of the protein (K) is 82%.

All of the proteins (I) to (L) have ω3-DES activity.

In the protein (J), the identity with the amino acid sequence of the protein (I) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of ω3-DES activity. Further, specific examples of the protein (J) include a protein in which 1 or several (for example 1 or more and 164 or less, preferably 1 or more and 144 or less, more preferably 1 or more and 123 or less, further preferably 1 or more and 103 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence of the protein (I).

In the protein (L), the identity with the amino acid sequence of the protein (K) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of ω3-DES activity. Further, specific examples of the protein (L) include a protein in which 1 or several (for example 1 or more and 163 or less, preferably 1 or more and 143 or less, more preferably 1 or more and 123 or less, further preferably 1 or more and 102 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence of the protein (K).

Specific examples of a method for introducing the mutation into the amino acid sequence include the above-mentioned method with regard to the Δ12-DES.

The proteins (I) to (L) can be obtained by chemical techniques, genetic engineering techniques or the like that are ordinarily carried out. For example, a natural product-derived protein can be obtained through isolation, purification and the like from *Nannochloropsis oculata* or *Nannochloropsis gaditana*. In addition, the proteins (I) to (L) can be obtained by artificial chemical synthesis based on the amino acid sequence set forth in SEQ ID NO: 5 or 49. Alternatively, as recombinant proteins, proteins (I) to (L) may also be prepared by gene recombination technologies. In the case of preparing a recombinant protein, a gene encoding the ω3-DES described below can be used.

An example of the gene encoding the ω3-DES (preferably, any one of the proteins (I) to (L)) (hereinafter, also referred to as "ω3-DES gene") includes a gene consisting of any one of the following DNAs (i) to (l).

(i) a DNA consisting of the nucleotide sequence set forth in SEQ ID NO: 6;

(j) a DNA consisting of a nucleotide sequence having 60% or more identity with the nucleotide sequence of the DNA (i), and encoding a protein having ω3-DES activity;

(k) a DNA consisting of the nucleotide sequence set forth in SEQ ID NO: 50; and (l) a DNA consisting of a nucleotide sequence having 60% or more identity with the nucleotide sequence of the DNA (k), and encoding a protein having ω3-DES activity.

The nucleotide sequence set forth in SEQ ID NO: 6 is a nucleotide sequence of a gene encoding the protein (Noω3-DES) consisting of the amino acid sequence set forth in SEQ ID NO: 5 (hereinafter, also referred to as "Noω3-DES gene").

The nucleotide sequence set forth in SEQ ID NO: 50 is a nucleotide sequence of a gene encoding the protein (Ngω3-DES) consisting of the amino acid sequence set forth in SEQ ID NO: 49.

In the DNA (j), the identity with the nucleotide sequence of the DNA (i) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of ω3-DES activity.

Further, the DNA (j) is also preferably a DNA in which 1 or several (for example 1 or more and 494 or less, preferably 1 or more and 432 or less, more preferably 1 or more and 370 or less, further preferably 1 or more and 309 or less, further preferably 1 or more and 247 or less, further preferably 1 or more and 185 or less, further preferably 1 or more and 124 or less, further preferably 1 or more and 99 or less, further preferably 1 or more and 62 or less, further preferably 1 or more and 25 or less, and furthermore preferably 1 or more and 13 or less) nucleotides are deleted, substituted, inserted or added to the nucleotide sequence of the DNA (i), and encoding a protein having ω3-DES activity.

Furthermore, the DNA (j) is also preferably a DNA capable of hybridizing with a DNA consisting of the nucleotide sequence complementary with the DNA (i) under a stringent condition, and encoding a protein having ω3-DES activity.

In the DNA (l), the identity with the nucleotide sequence of the DNA (k) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99 or more, in view of ω3-DES activity.

Further, the DNA (l) is also preferably a DNA in which 1 or several (for example 1 or more and 490 or less, preferably 1 or more and 429 or less, more preferably 1 or more and 368 or less, further preferably 1 or more and 306 or less, further preferably 1 or more and 245 or less, further preferably 1 or more and 184 or less, further preferably 1 or more and 123 or less, further preferably 1 or more and 98 or less, further preferably 1 or more and 62 or less, further preferably 1 or more and 25 or less, and furthermore preferably 1 or more and 13 or less) nucleotides are deleted, substituted, inserted or added to the nucleotide sequence of the DNA (k), and encoding a protein having ω3-DES activity.

Furthermore, the DNA (l) is also preferably a DNA capable of hybridizing with a DNA consisting of the nucleotide sequence complementary with the DNA (k) under a stringent condition, and encoding a protein having ω3-DES activity.

In the present invention, it is preferred to also enhance expression of a Δ5-desaturase (hereinafter, also referred to as "Δ5-DES"), in addition to the Δ12-DES and the Δ6-DES, as with the ω3-DES.

In the present specification, the term "Δ5-DES" means a protein (enzyme) that catalyzes a reaction of introducing an unsaturated bond into a Δ5-position of dihomo-γ-linolenic acid (hereinafter, also denoted as "C20:3Δ8,11,14") to form C20:4Δ5,8,11,14, as shown in FIG. 1. Then, in the present specification, the term "Δ5-desaturase activity" (hereinafter, also referred to as "Δ5-DES activity") means activity for introducing the unsaturated bond into the Δ5-position of C20:3Δ8,11,14.

In the algae belonging to the genus *Nannochloropsis*, in which the expressions of the Δ12-DES and the Δ6-DES are enhanced, production amount of C18:3Δ6,9,12 and C20:3Δ8,11,14 synthesized by elongating a carbon chain in C18:3Δ6,9,12 by two chains is increased by a sequential reaction catalyzed by the Δ12-DES and the Δ6-DES. Accordingly, in the algae belonging to the genus *Nannochloropsis*, in which the expressions of the Δ12-DES and the Δ6-DES are enhanced, introduction of an unsaturated bond into the Δ5-position of C20:308,11,14 is accelerated by also enhancing expression of the Δ5-DES, and production amount of C20:4Δ5,8,11,14 serving as a substrate of synthesis of C20:5Δ5,8,11,14,17 is further increased.

It can be confirmed that the protein has the Δ5-DES activity by a system using a Δ5-DES gene deletion strain, for example. Alternatively, it can also be confirmed by examining formation of arachidonic acid by introducing the DNA of which a gene encoding the above-described protein was ligated downstream of a promoter functioning inside a host cell, into the Δ5-DES gene deletion strain. Alternatively, it can also be confirmed by measuring a decrease of dihomo-γ-linolenic acid amount or an increase of arachidonic acid amount according to an ordinary method by preparing the Δ5-DES or cell lysate containing the same to react the resultant material with the reaction solution containing dihomo-γ-linolenic acid derivatives (the thioester compound with CoA, the ester compound with glycerol, or the like).

Preferred examples of the Δ5-DES in the present invention include the following proteins (M) to (P):

(M) a protein consisting of the amino acid sequence set forth in SEQ ID NO: 7;

(N) a protein consisting of an amino acid sequence having 60% or more identity with the amino acid sequence of the protein (M), and having Δ5-desaturase activity;

(O) a protein consisting of the amino acid sequence set forth in SEQ ID NO: 51; and (P) a protein consisting of an amino acid sequence having 60% or more identity with the amino acid sequence of the protein (O), and having Δ5-desaturase activity.

The protein consisting of the amino acid sequence set forth in SEQ ID NO: 7 is a Δ5-DES derived from *Nannochloropsis oculata* strain NIES-2145 (hereinafter, also referred to as "NoΔ5-DES"). Further, the protein consisting of the amino acid sequence set forth in SEQ ID NO: 51 is a Δ5-DES derived from *Nannochloropsis gaditana* B-31 strain (hereinafter, also referred to as "NgΔ5-DES").

Note that, identity of the amino acid sequence of the protein (M) with the amino acid sequence of the protein (O) is 81%.

All of the proteins (M) to (P) have Δ5-DES activity.

In the protein (N), the identity with the amino acid sequence of the protein (M) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ5-DES activity. Further, specific examples of the protein (N) include a protein in which 1 or several (for example 1 or more and 211 or less, preferably 1 or more and 185 or less, more preferably 1 or more and 158 or less, further preferably 1 or more and 132 or less, furthermore preferably 1 or more and 106 or less, furthermore preferably 1 or more and 79 or less, furthermore preferably 1 or more and 53 or less, furthermore preferably 1 or more and 43 or less, furthermore preferably 1 or more and 27 or less, furthermore preferably 1 or more and 11 or less, and furthermore preferably 1 or more and 6 or less) amino acids are deleted, substituted, inserted or added to the amino acid sequence of the protein (M).

In the protein (P), the identity with the amino acid sequence of the protein (0) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ5-DES activity. Further, specific examples of the protein (P) include a protein in which 1 or several (for example 1 or more and 206 or less, preferably 1 or more and 181 or less, more preferably 1 or more and 155 or less, further preferably 1 or more and 129 or less, furthermore preferably 1 or more and 103 or less, furthermore preferably 1 or more and 78 or less, furthermore preferably 1 or more and 52 or less, furthermore preferably 1 or more and 42 or less, furthermore preferably 1 or more and 26 or less, furthermore preferably 1 or more and 11 or less, and furthermore preferably 1 or more and 6 or less) amino acids are deleted, substituted, inserted or added to the amino acid sequence of the protein (O).

Specific examples of a method for introducing the mutation into the amino acid sequence include the above-mentioned method with regard to the Δ12-DES.

The proteins (M) to (P) can be obtained by chemical techniques, genetic engineering techniques or the like that are ordinarily carried out. For example, a natural product-derived protein can be obtained through isolation, purification and the like from *Nannochloropsis oculata* or *Nannochloropsis gaditana*. In addition, the proteins (M) to (P) can be obtained by artificial chemical synthesis based on the amino acid sequence set forth in SEQ ID NO: 7 or 51. Alternatively, as recombinant proteins, proteins (M) to (P) may also be prepared by gene recombination technologies. In the case of preparing a recombinant protein, a gene encoding the Δ5-DES described below can be used.

An example of the gene encoding the Δ5-DES (preferably, any one of the proteins (M) to (P)) (hereinafter, also referred to as "Δ5-DES gene") includes a gene consisting of any one of the following DNAs (m) to (p).

(m) a DNA consisting of the nucleotide sequence set forth in SEQ ID NO: 8;

(n) a DNA consisting of a nucleotide sequence having 60% or more identity with the nucleotide sequence of the DNA (m), and encoding a protein having Δ5-DES activity;

(o) a DNA consisting of the nucleotide sequence set forth in SEQ ID NO: 52; and (p) a DNA consisting of a nucleotide sequence having 60% or more identity with the nucleotide sequence of the DNA (o), and encoding a protein having Δ5-DES activity.

The nucleotide sequence set forth in SEQ ID NO: 8 is a nucleotide sequence of a gene encoding the protein (NoΔ5-DES) consisting of the amino acid sequence set forth in SEQ ID NO: 7 (hereinafter, also referred to as "NoΔ5-DES gene").

The nucleotide sequence set forth in SEQ ID NO: 52 is a nucleotide sequence of a gene encoding the protein (NgΔ5-DES) consisting of the amino acid sequence set forth in SEQ ID NO: 51 (hereinafter, also referred to as "NgΔ5-DES gene").

In the DNA (n), the identity with the nucleotide sequence of the DNA (m) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ5-DES activity.

Further, the DNA (n) is also preferably a DNA in which 1 or several (for example 1 or more and 633 or less, preferably 1 or more and 554 or less, more preferably 1 or more and 475 or less, further preferably 1 or more and 396 or less, further preferably 1 or more and 317 or less, further preferably 1 or more and 238 or less, further preferably 1 or more and 159 or less, further preferably 1 or more and 127 or less, further preferably 1 or more and 80 or less, further preferably 1 or more and 32 or less, and furthermore preferably 1 or more and 16 or less) nucleotides are deleted, substituted, inserted or added to the nucleotide sequence of the DNA (m), and encoding a protein having Δ5-DES activity.

Furthermore, the DNA (n) is also preferably a DNA capable of hybridizing with a DNA consisting of the nucleotide sequence complementary with the DNA (m) under a stringent condition, and encoding a protein having Δ5-DES activity.

In the DNA (p), the identity with the nucleotide sequence of the DNA (o) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99 or more, in view of Δ5-DES activity.

Further, the DNA (p) is also preferably a DNA in which 1 or several (for example 1 or more and 620 or less, preferably 1 or more and 542 or less, more preferably 1 or more and 465 or less, further preferably 1 or more and 387 or less, further preferably 1 or more and 310 or less, further preferably 1 or more and 233 or less, further preferably 1 or more and 155 or less, further preferably 1 or more and 124 or less, further preferably 1 or more and 78 or less, further preferably 1 or more and 31 or less, and furthermore preferably 1 or more and 16 or less) nucleotides are deleted, substituted, inserted or added to the nucleotide sequence of the DNA (o), and encoding a protein having Δ5-DES activity.

Furthermore, the DNA (p) is also preferably a DNA capable of hybridizing with a DNA consisting of the nucleotide sequence complementary with the DNA (o) under a stringent condition, and encoding a protein having Δ5-DES activity.

In the present invention, it is preferred to also enhance expression of a Δ9-desaturase (hereinafter, also referred to as "Δ9-DES"), in addition to the 012-DES and the Δ6-DES, as with the ω3-DES and the Δ5-DES.

In the present specification, the term "Δ9-DES" means a protein (enzyme) that catalyzes a reaction of introducing an unsaturated bond into a Δ9-position of stearic acid (hereinafter, also denoted as "C18:0") to form C18:1Δ9, as shown in FIG. 1. Then, in the present specification, the term "Δ9-desaturase activity" (hereinafter, also referred to as "Δ9-DES activity") means activity for introducing the unsaturated bond into the Δ9-position of C18:0.

Production amount of C18:1Δ9 being a starting material of the sequential reaction catalyzed by the Δ12-DES and the Δ6-DES is increased by enhancing expression of the Δ9-DES, and the productivity of PUFA can be further improved.

It can be confirmed that the protein has the Δ9-DES activity by a system using a Δ9-DES gene deletion strain, for example. Alternatively, it can also be confirmed by examining formation of oleic acid by introducing the DNA of which a gene encoding the above-described protein was ligated downstream of a promoter functioning inside a host cell, into the Δ9-DES gene deletion strain. Alternatively, it can also be confirmed by measuring a decrease of stearic acid amount or an increase of oleic acid amount according to an ordinary method by preparing the Δ9-DES or cell lysate containing the same to react the resultant material with the reaction solution containing stearic acid, stearoyl-CoA, or the like.

Preferred examples of the Δ9-DES in the present invention include the following proteins (Q) to (T):

(Q) a protein consisting of the amino acid sequence set forth in SEQ ID NO: 9;

(R) a protein consisting of an amino acid sequence having 60% or more identity with the amino acid sequence of the protein (Q), and having Δ9-desaturase activity;

(S) a protein consisting of the amino acid sequence set forth in SEQ ID NO: 53; and (T) a protein consisting of an amino acid sequence having 60% or more identity with the amino acid sequence of the protein (S), and having Δ9-desaturase activity.

The protein consisting of the amino acid sequence set forth in SEQ ID NO: 9 is a Δ9-DES derived from *Nannochloropsis oculata* strain NIES-2145 (hereinafter, also referred to as "NoΔ9-DES"). Further, the protein consisting of the amino acid sequence set forth in SEQ ID NO: 53 is a Δ9-DES derived from *Nannochloropsis gaditana* B-31 strain (hereinafter, also referred to as "NgΔ9-DES").

Note that, identity of the amino acid sequence of the protein (Q) with the amino acid sequence of the protein (S) is 93%.

All of the proteins (Q) to (T) have Δ9-DES activity.

In the protein (R), the identity with the amino acid sequence of the protein (Q) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ9-DES activity. Further, specific examples of the protein (R) include a protein in which 1 or several (for example 1 or more and 144 or less, preferably 1 or more and 126 or less, more preferably 1 or more and 108 or less, further preferably 1 or more and 90 or less, furthermore preferably 1 or more and 72 or less, furthermore preferably 1 or more and 54 or less, furthermore preferably 1 or more and 36 or less, furthermore preferably 1 or more and 29 or less, furthermore preferably 1 or more and 18 or less, furthermore preferably 1 or more and 8 or less, and furthermore preferably 1 or more and 4 or less) amino acids are deleted, substituted, inserted or added to the amino acid sequence of the protein (Q).

In the protein (T), the identity with the amino acid sequence of the protein (S) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ9-DES activity. Further, specific examples of the protein (T) include a protein in which 1 or several (for example 1 or more and 136 or less, preferably 1 or more and 119 or less, more preferably 1 or more and 102 or less, further preferably 1 or more and 85 or less, furthermore preferably 1 or more and 68 or less, furthermore preferably 1 or more and 51 or less, furthermore preferably 1 or more and 34 or less, furthermore preferably 1 or more and 28 or less, furthermore preferably 1 or more and 17 or less, furthermore preferably 1 or more and 7 or less, and furthermore preferably 1 or more and 4 or less) amino acids are deleted, substituted, inserted or added to the amino acid sequence of the protein (S).

Specific examples of a method for introducing the mutation into the amino acid sequence include the above-mentioned method with regard to the Δ12-DES.

The proteins (Q) to (T) can be obtained by chemical techniques, genetic engineering techniques or the like that are ordinarily carried out. For example, a natural product-derived protein can be obtained through isolation, purification and the like from *Nannochloropsis oculata* or *Nannochloropsis gaditana*. In addition, the proteins (Q) to (T) can be obtained by artificial chemical synthesis based on the amino acid sequence set forth in SEQ ID NO: 9 or 53. Alternatively, as recombinant proteins, proteins (Q) to (T) may also be prepared by gene recombination technologies. In the case of preparing a recombinant protein, a gene encoding the Δ9-DES described below can be used.

An example of the gene encoding the Δ9-DES (preferably, any one of the proteins (Q) to (T)) (hereinafter, also referred to as "Δ9-DES gene") includes a gene consisting of any one of the following DNAs (q) to (t).

(q) a DNA consisting of the nucleotide sequence set forth in SEQ ID NO: 10;

(r) a DNA consisting of a nucleotide sequence having 60% or more identity with the nucleotide sequence of the DNA (q), and encoding a protein having Δ9-DES activity;

(s) a DNA consisting of the nucleotide sequence set forth in SEQ ID NO: 54; and (t) a DNA consisting of a nucleotide sequence having 60% or more identity with the nucleotide sequence of the DNA (s), and encoding a protein having Δ9-DES activity.

The nucleotide sequence set forth in SEQ ID NO: 10 is a nucleotide sequence of a gene encoding the protein (NoΔ9-DES) consisting of the amino acid sequence set forth in SEQ ID NO: 9 (hereinafter, also referred to as "NoΔ9-DES gene").

The nucleotide sequence set forth in SEQ ID NO: 54 is a nucleotide sequence of a gene encoding the protein (NgΔ9-DES) consisting of the amino acid sequence set forth in SEQ ID NO: 53 (hereinafter, also referred to as "NgΔ9-DES gene").

In the DNA (r), the identity with the nucleotide sequence of the DNA (q) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ9-DES activity.

Further, the DNA (r) is also preferably a DNA in which 1 or several (for example 1 or more and 432 or less, preferably 1 or more and 378 or less, more preferably 1 or more and 324 or less, further preferably 1 or more and 270 or less, further preferably 1 or more and 216 or less, further preferably 1 or more and 162 or less, further preferably 1 or more and 108 or less, further preferably 1 or more and 87 or less, further preferably 1 or more and 54 or less, further preferably 1 or more and 22 or less, and furthermore preferably 1 or more and 11 or less) nucleotides are deleted, substituted, inserted or added to the nucleotide sequence of the DNA (q), and encoding a protein having Δ9-DES activity.

Furthermore, the DNA (r) is also preferably a DNA capable of hybridizing with a DNA consisting of the nucleotide sequence complementary with the DNA (q) under a stringent condition, and encoding a protein having Δ9-DES activity.

In the DNA (t), the identity with the nucleotide sequence of the DNA (s) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99 or more, in view of Δ9-DES activity.

Further, the DNA (t) is also preferably a DNA in which 1 or several (for example 1 or more and 410 or less, preferably 1 or more and 359 or less, more preferably 1 or more and 307 or less, further preferably 1 or more and 256 or less, further preferably 1 or more and 205 or less, further preferably 1 or more and 154 or less, further preferably 1 or more and 103 or less, further preferably 1 or more and 82 or less, further preferably 1 or more and 52 or less, further preferably 1 or more and 21 or less, and furthermore preferably 1 or more and 11 or less) nucleotides are deleted, substituted, inserted or added to the nucleotide sequence of the DNA (s), and encoding a protein having Δ9-DES activity.

Furthermore, the DNA (t) is also preferably a DNA capable of hybridizing with a DNA consisting of the nucleotide sequence complementary with the DNA (s) under a stringent condition, and encoding a protein having Δ9-DES activity.

In the present invention, it is preferred to also enhance expression of a Δ6-elongase (hereinafter, also referred to as "Δ6-FLO"), in addition to the Δ12-DES and the Δ6-DES, as with the ω3-DES, the Δ5-DES and the Δ9-DES.

A term "Δ6-FLO" in the present specification means a protein (enzyme) that catalyzes a reaction of elongating a carbon chain in γ-linolenic acid (C18:3Δ6,9,12) by two carbon atoms to form dihomo-γ-linolenic acid (C20:3Δ8,11,14) as shown in FIG. 1. Then, a term "Δ6-elongase activity (hereinafter, also referred to as "Δ6-ELO activity") in the present specification means activity of elongating the carbon chain of C18:3Δ6,9,12 by two carbon atoms.

In the algae belonging to the genus *Nannochloropsis*, in which the expressions of the Δ12-DES and the Δ6-DES are enhanced, production amount of C18:3Δ6,9,12 is increased by a sequential reaction catalyzed by the Δ12-DES and the Δ6-DES. Accordingly, in the algae belonging to the genus *Nannochloropsis*, in which the expressions of the Δ12-DES and the Δ6-DES are enhanced, introduction (elongation) of the carbon chain into 018:3Δ6,9,12 by two carbon atoms is accelerated by also enhancing expression of the Δ6-ELO, and production amount of C20:3Δ8,11,14, C20:4Δ5,8,11,14 and 20:5Δ5,8,11,14,17 is further increased.

It can be confirmed that the protein has the Δ6-ELO activity by a system using a Δ6-ELO gene deletion strain, for example. Alternatively, it can also be confirmed by examining formation of dihomo-γ-linolenic acid by introducing the DNA of which a gene encoding the above-described protein was ligated downstream of a promoter functioning inside a host cell, into the Δ6-ELO gene deletion strain. Alternatively, it can also be confirmed by measuring a decrease of γ-linolenic acid amount or an increase of dihomo-γ-linolenic acid amount according to an ordinary method by preparing the Δ6-ELO or cell lysate containing the same to react the resultant material with the reaction solution containing γ-linolenic acid derivatives (the thioester compound with CoA, the ester compound with glycerol, or the like).

Preferred examples of the Δ6-ELO in the present invention include the following proteins (U) and (V):

(U) a protein consisting of the amino acid sequence set forth in SEQ ID NO: 74; and (V) a protein consisting of an amino acid sequence having 60% or more identity with the amino acid sequence of the protein (U), and having Δ6-ELO activity.

The protein consisting of the amino acid sequence set forth in SEQ ID NO: 74 is a Δ6-ELO derived from *Nannochloropsis oculata* strain NIES-2145 (hereinafter, also referred to as "NoΔ6-ELO").

Both of the proteins (U) and (V) have Δ6-ELO activity.

In the protein (V), the identity with the amino acid sequence of the protein (U) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-ELO activity. Further, specific examples of the protein (V) include a protein in which 1 or several (for example 1 or more and 111 or less, preferably 1 or more and 97 or less, more preferably 1 or more and 83 or less, further preferably 1 or more and 69 or less, furthermore preferably 1 or more and 56 or less, furthermore preferably 1 or more and 42 or less, furthermore preferably 1 or more and 28 or less, furthermore preferably 1 or more and 23 or less, furthermore preferably 1 or more and 14 or less, furthermore preferably 1 or more and 6 or less, and furthermore preferably 1 or more and 3 or less) amino acids are deleted, substituted, inserted or added to the amino acid sequence of the protein (U).

Specific examples of a method for introducing the mutation into the amino acid sequence include the above-mentioned method with regard to the Δ12-DES.

The proteins (U) and (V) can be obtained by chemical techniques, genetic engineering techniques or the like that are ordinarily carried out. For example, a natural product-derived protein can be obtained through isolation, purification and the like from *Nannochloropsis oculata*. In addition, the proteins (U) and (V) can be obtained by artificial chemical synthesis based on the amino acid sequence set forth in SEQ ID NO: 74. Alternatively, as recombinant proteins, proteins (U) and (V) may also be prepared by gene recombination technologies. In the case of preparing a recombinant protein, a gene encoding the Δ6-ELO described below can be used.

An example of the gene encoding the Δ6-ELO (preferably, any one of the proteins (U) and (V)) (hereinafter, also referred to as "Δ6-ELO gene") includes a gene consisting of any one of the following DNAs (u) and (v).

(u) a DNA consisting of the nucleotide sequence set forth in SEQ ID NO: 73; and (v) a DNA consisting of a nucleotide sequence having 60% or more identity with the nucleotide sequence of the DNA (u), and encoding a protein having Δ6-ELO activity.

The nucleotide sequence set forth in SEQ ID NO: 73 is a nucleotide sequence of a gene encoding the protein (NoΔ6-ELO) consisting of the amino acid sequence set forth in SEQ ID NO: 74 (hereinafter, also referred to as "NoΔ6-ELO gene").

In the DNA (v), the identity with the nucleotide sequence of the DNA (u) is preferably 65% or more, more preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of Δ6-ELO activity.

Further, the DNA (v) is also preferably a DNA in which 1 or several (for example 1 or more and 333 or less, preferably 1 or more and 291 or less, more preferably 1 or more and 250 or less, further preferably 1 or more and 208 or less, further preferably 1 or more and 167 or less, further preferably 1 or more and 125 or less, further preferably 1 or more and 84 or less, further preferably 1 or more and 67 or less, further preferably 1 or more and 42 or less, further preferably 1 or more and 17 or less, and furthermore preferably 1 or more and 9 or less) nucleotides are deleted, substituted, inserted or added to the nucleotide sequence of the DNA (u), and encoding a protein having Δ6-ELO activity.

Furthermore, the DNA (v) is also preferably a DNA capable of hybridizing with a DNA consisting of the nucleotide sequence complementary with the DNA (u) under a stringent condition, and encoding a protein having Δ6-ELO activity.

As mentioned above, in the pathway of PUFA synthesis in the algae belonging to the genus *Nannochloropsis*, the reaction of forming linoleic acid from oleic acid, and forming γ-linolenic acid from the linoleic acid formed is the rate-limiting step. Accordingly, in the present invention, the expressions of only the Δ12-DES and the Δ6-DES that catalyzes the reaction in the rate-limiting step may be enhanced.

Alternatively, from a viewpoint of more improving the productivity of PUFA, in addition to the Δ12-DES and the Δ6-DES, at least any one kind of enzymes selected from the group consisting of the ω3-DES, the Δ5-DES, the Δ9-DES and the Δ6-ELO is preferably enhanced, and two or more kinds of enzymes selected from the group consisting of the ω3-DES, the Δ5-DES, the Δ9-DES and the Δ6-ELO are more preferably enhanced.

A method of enhancing the expression of the each enzyme can be appropriately selected from an ordinarily method, and a method of enhancing the expression of the gene encoding the each enzyme is preferred. Specific examples include a method of introducing the each gene into a host to enhance the expression of the gene, a method of modifying expression regulation regions (promoter, terminator, or the like) of the gene in a host having the each gene on a genome, and the like. Among them, the method of introducing the each gene into a host to enhance the expression of the each gene is preferred.

Hereinafter, in the present specification, a cell in which expression of target protein, such as each enzyme, is enhanced is also referred to as the "transformant", and a cell in which the expression of the target protein is not enhanced is also referred to as the "host" or "wild type strain".

In the transformant used in the present invention, the productivity of PUFA and lipids containing the same as components (production amount of PUFA and lipids containing the same as components, and the proportion of PUFA and lipids containing the same as components in the whole fatty acids or lipids to be produced) is tend to increase, in comparison with that in a host. Moreover, as a result, in the transformant, the fatty acid composition in the lipid is modified. Therefore, the present invention using the transformant can be preferably applied to production of fatty acids or lipids having specific number of carbon atoms, particularly PUFA or lipids containing the same as components, preferably PUFA having 18 or more carbon atoms or lipids containing the same as components, more preferably PUFA having 18 or 20 carbon atoms or lipids containing the same as components, further preferably PUFA having 20 carbon atoms or lipids containing the same as components, further preferably C20:3, C20:4 or C20:5, or lipids containing the same as components, further preferably dihomo-γ-linolenic acid, arachidonic acid, or eicosapentaenoic acid or lipids containing the same as components, further preferably arachidonic acid, eicosapentaenoic acid or lipids containing the same as components, or eicosapentaenoic acid or lipids containing the same as components.

The productivity of fatty acids and lipids of the host and the transformant can be measured by the method used in Examples described below.

The method of introducing the each gene into a host to enhance the expression of the gene is described.

The each gene can be obtained by genetic engineering techniques that are ordinarily carried out. For example, the each gene can be artificially synthesized based on the amino acid sequence set forth in SEQ ID NO: 1, 3, 5, 7, 9, 45, 47, 49, 51, 53 or 74, or the nucleotide sequence set forth in SEQ ID NO: 2, 4, 6, 8, 10, 46, 48, 50, 52, 54 or 73. The synthesis of the each gene can be achieved by utilizing, for example, the services of Invitrogen. Further, the gene can also be obtained by cloning from algae belonging to the genus *Nannochloropsis* such as *Nannochloropsis oculata* and *Nannochloropsis gaditana*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the each gene into a host according to an ordinarily method. Specifically, the transformant can be produced by preparing a recombinant vector or a gene expression cassette which is capable of expressing the each gene in a host cell, introducing this vector or cassette into the host cell, and thereby transforming the host cell.

The alga used in the present invention is an alga belonging to the genus *Nannochloropsis*. The algae of the genus *Nannochloropsis* are small algae (microalgae) having a globular shape or an elliptical shape and a size of about 2 to 5 μm.

Specific examples of the algae belonging to the genus *Nannochloropsis* used in the present invention include, from a viewpoint of establishment of a gene recombination technique, *Nannochloropsis oculata, Nannochloropsis gaditana, Nannochloropsis salina, Nannochloropsis oceanica, Nannochloropsis atomus, Nannochloropsis maculata, Nannochloropsis granulate, Nannochloropsis* sp., and the like. Among these, from a viewpoint of the lipid productivity, *Nannochloropsis oculata* or *Nannochloropsis gaditana* is preferable, and *Nannochloropsis oculata* is more preferable.

A plasmid for gene expression or a vector (plasmid) containing the gene expression cassette may be any vector capable of introducing the gene encoding the target protein into a host, and expressing the target gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, pUC19 (manufactured by Takara Bio), P66 (*Chlamydomonas* Center), P-322 (*Chlamydomonas* Center), pPha-T1 (see Yangmin Gong, et al., Journal of Basic Microbiology, 2011, vol. 51, p. 666-672) and pJET1 (manufactured by COSMO BIO). In particular, pUC19, pPha-T1 or pJET1 is preferably used. Moreover, the host can be transformed, with referring to the method described in Proceedings of the National Academy of Sciences of the United States of America, 2011, vol. 108(52), by using the DNA fragment consisting of the target gene, a promoter and a terminator (gene expression cassette). Specific examples of this DNA fragment include a DNA fragment amplified by PCR method, and a restriction enzyme-cut DNA fragment.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), c-phycocyanin β subunit (cpcB), cauliflower mosaic virus 35S RNA promoter, promoters for housekeeping genes (e.g., tubulin promoter, actin promoter and ubiquitin promoter), *Brassica napus* or *Brassica rapa*-derived *Napin* gene promoter, plant-derived Rubisco promoter, a promoter of a violaxanthin/(chlorophyll a)-binding protein gene derived from the genus *Nannochloropsis* (VCP1 promoter, VCP2 promoter) (Proceedings of the National Academy of Sciences of the United States of America, 2011, vol. 108(52)), and a promoter of an oleosin-like protein LDSP (lipid droplet surface protein) gene derived from the genus *Nannochloropsis* (PLOS Genetics, 2012, vol. 8(11): e1003064. DOI: 10.1371). In the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, a gentamicin resistance gene, and a hygromycin resistance gene. Further, it is also possible to use a deletion of an auxotrophy-related gene or the like as the selection marker gene.

Introduction of the gene encoding a target protein to the vector can be conducted by an ordinary technique such as restriction enzyme treatment and ligation.

Furthermore, the method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. In the present invention, transformation can also be performed by using the electroporation method described in Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In a host having the each gene on a genome, a method of modifying expression regulation regions of the gene and enhancing the expression of the gene is described.

The "expression regulation region" indicates the promoter or the terminator, in which these sequences are generally involved in regulation of the expression amount (transcription amount, translation amount) of the gene adjacent thereto. In a host having the each gene on a genome, productivity of PUFA or lipids containing the same as components can be improved by modifying expression regulation regions of the gene and enhancing the expression of the each gene.

Specific examples of the method of modifying the expression regulation regions include interchange of promoters. In the host having the above-mentioned each desaturase gene or elongase gene on the genome, the expression of the each gene can be enhanced by interchanging the promoter of the gene (hereinafter, also referred to as "desaturase promoter" or "elongase promoter") with a promoter having higher transcriptional activity.

For example, in *Nannochloropsis oculata* strain NIES-2145 being one of the hosts having the each desaturase gene on the genome, the NoΔ12-DES gene exists at the downstream of a DNA sequence consisting of the nucleotide sequence set forth in SEQ ID NO: 55, and a NoΔ12-DES gene promoter region exists in the DNA sequence consisting of the nucleotide sequence set forth in SEQ ID NO: 55.

Further, the NoΔ6-DES gene exists at the downstream of a DNA sequence consisting of the nucleotide sequence set forth in SEQ ID NO: 56, and a NoΔ6-DES gene promoter region exists in the DNA sequence consisting of the nucleotide sequence set forth in SEQ ID NO: 56.

Furthermore, the Noω3-DES gene exists at the downstream of a DNA sequence consisting of the nucleotide sequence set forth in SEQ ID NO: 57, and a Noω3-DES gene promoter region exists in the DNA sequence consisting of the nucleotide sequence set forth in SEQ ID NO: 57.

Furthermore, the NoΔ5-DES gene exists at the downstream of a DNA sequence consisting of the nucleotide sequence set forth in SEQ ID NO: 58, and a NoΔ5-DES gene promoter region exists in the DNA sequence consisting of the nucleotide sequence set forth in SEQ ID NO: 58.

Furthermore, the NoΔ9-DES gene exists at the downstream of a DNA sequence consisting of the nucleotide sequence set forth in SEQ ID NO: 59, and a NoΔ9-DES gene promoter region exists in the DNA sequence consisting of the nucleotide sequence set forth in SEQ ID NO: 59.

Furthermore, the NoΔ6-ELO gene exists at the downstream of a DNA sequence consisting of the nucleotide sequence set forth in SEQ ID NO: 75, and a NoΔ6-ELO gene promoter region exists in the DNA sequence consisting of the nucleotide sequence set forth in SEQ ID NO: 75.

Therefore, the expression of each of the above-described gene can be enhanced by partially or wholly interchanging the DNA sequences consisting of any one of the nucleotide sequences set forth in SEQ ID NO: 55 to 59 and 75 with the promoter having higher transcriptional activity.

The promoter used for interchanging the desaturase promoter or elongase promoter is not particularly limited, and can be appropriately selected from the promoters that are higher in the transcriptional activity than the desaturase promoter or elongase promoter and suitable for production of PUFA or lipids containing the same as the components.

Specific examples of the promoter which can be preferably used in the present invention include a tubulin promoter, a heat shock protein promoter, the above-described promoter of a violaxanthin/(chlorophyll a)-binding protein gene (VCP1 promoter, VCP2 promoter), and a promoter of an oleosin-like protein LDSP gene derived from the genus *Nannochloropsis*. From a viewpoint of improvement in the productivity of PUFA or lipids containing the same as components, the promoter of a violaxanthin/(chlorophyll a)-binding protein gene or the promoter of LDSP gene is more preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified.

The method of modifying a target promoter according to such homologous recombination can be conducted with, for example, referring to literature such as Methods in molecular biology, 1995, vol. 47, p. 291-302. In particular, in the case where the host is the algae belonging to the genus *Nannochloropsis*, specific region in a genome can be modified, with referring to literature such as Proceedings of the National Academy of Sciences of the United States of America, 2011, vol. 108(52), by homologous recombination method.

Furthermore, in the transformant of the present invention, expression of KAS is preferably enhanced, and expression of a gene encoding a KAS (hereinafter, also merely referred to as "KAS gene") is more preferably enhanced.

The KAS is one kind of fatty acid synthesis enzymes which catalyze the condensation reaction of the acyl-ACP with the malonyl-ACP, and is involved in the synthesis of acyl-ACP. In the chloroplast, the elongation reaction of the carbon chain is repeated starting from an acetyl-ACP (or acetyl-CoA), and finally an acyl-ACP having 16 or 18 carbon atoms is synthesized.

In the first stage of the fatty acid synthesis, an acetoacetyl-ACP is formed by a condensation reaction between the acetyl-ACP (or acetyl-CoA) and a malonyl-ACP. The KAS catalyzes this reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

Therefore, the productivity of the lipids in the algae used for producing the lipids, particularly, the productivity of the fatty acids can be further improved by enhancing expression of the KAS, preferably, enhancing expression of the KAS gene.

The KAS that can be preferably used in the present invention needs to be the protein having β-ketoacyl-ACP synthase activity (hereinafter, also referred to as "KAS activity"). Herein, the term "KAS activity" means the activity to catalyze the condensation reaction of the acetyl-ACP or the acyl-ACP with the malonyl-ACP.

The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses acyl-ACPs, as substrates.

KAS is categorized into KAS I, KAS II, KAS III or KAS IV according to their substrate specificity. For example, KAS III uses an acetyl-ACP (or acetyl-CoA) having 2 carbon atoms as the substrate to catalyze the elongation reaction that the number of carbon atoms is increased from 2 to 4. KAS I mainly catalyzes the elongation reaction that the number of carbon atoms is increased from 4 to 16, to synthesize the palmitoyl-ACP having 16 carbon atoms. KAS II mainly catalyzes the elongation reaction to the long-chain acyl group having 18 carbon atoms or more, to synthesize a long-chain acyl-ACP. KAS IV mainly catalyzes the elongation reaction that the acyl-ACP having 6 carbon atoms is converted to the acyl-ACP having 14 carbon atoms, to synthesize a medium-chain acyl-ACP.

Therefore, the productivity of the long-chain fatty acids can be further improved by enhancing expression of the KAS II, preferably, enhancing expression of a gene encoding the KAS II.

The KAS, which can be preferably used in the present invention, can be appropriately selected from the normal KAS or proteins functionally equivalent to the KAS, according to a kind of host or the like. Specific examples thereof include a KAS II derived from *Nannochloropsis oculata* (hereinafter, also referred to as "NoKASII") (SEQ ID NO: 60). Moreover, as the proteins functionally equivalent to the KAS II, a protein consisting of an amino acid sequence having 50% or more (preferably 70% or more, more preferably 80% or more, and further preferably 90% or more) identity with the amino acid sequence of the NoKASII, and having KAS activity, can be also used. Examples of the gene encoding the NoKASII include a gene consisting of a DNA consisting of the nucleotide sequence set forth in SEQ ID NO: 61; and a gene consisting of a DNA consisting of a nucleotide sequence having 50% or more (preferably 70% or more, more preferably 80% or more, and further preferably 90% or more) identity with the nucleotide sequence set forth in SEQ ID NO: 61, and encoding a protein having KAS activity.

Further, the transformants in which the expression of the KAS is enhanced (for example, the transformants in which the expression of a gene encoding the KAS is enhanced) can be prepared by an ordinary method. For example, the transformants can be prepared by a method similar to the above-described method for enhancing the expression of the each desaturase gene, such as a method for introducing a gene encoding the KAS into a host, a method, in the host having a gene encoding the KAS on a genome, for modifying expression regulation regions of the gene, or the like.

Furthermore, in the transformant of the present invention, expression of an ACP is preferably enhanced, and expression of a gene encoding an ACP (hereinafter, also merely referred to as "ACP gene") is more preferably enhanced.

The ACP functions as a scaffold (carrier) of a biosynthetic reaction of the fatty acids (elongation reaction of the fatty acids). The acyl group of the fatty acids forms a thioester bond with a phosphopantetheine group bonded to a serine residue of the ACP. The fatty acids are elongated in this state.

Therefore, the productivity of the lipids in the algae used for producing the lipids, particularly, the productivity of the fatty acids can be further improved by enhancing expression of the ACP, preferably, enhancing expression of the ACP gene.

The ACP that can be preferably used in the present invention needs to be the protein having acyl-carrier-protein activity (hereinafter, also referred to as "ACP activity"). A term "ACP activity" herein means activity that functions as the scaffold of the elongation reaction of the fatty acids by forming the thioester bond with the acyl group of the fatty acids.

The ACP activity of the protein can be confirmed by, for example, introducing a DNA produced by linking a gene encoding the protein to the downstream of a promoter which functions in a host cell, into an ACP gene deletion strain to complement the productivity of fatty acids. Alternatively, the ACP activity can be confirmed by introducing a DNA produced by linking a gene encoding the protein to the downstream of a promoter which functions in a host cell, into a host cell, culturing the thus-obtained cell under the conditions suitable for the expression of the introduced gene, and analyzing any change caused thereby in the fatty acid composition of the host cell or in the cultured liquid by an ordinary technique. Alternatively, the ACP activity can be confirmed by allowing the above-described protein to react with a coenzyme A (CoA) and suitable ACP synthase (phosphopantetheinyl transferase) to form holo-ACP in which the phosphopantetheine group is bonded therewith with reference to literature such as Biochemistry, 2011, vol. 50(25), p. 5704-5717. Alternatively, the ACP activity can be confirmed by allowing the above-described holo-ACP to react with the fatty acids and suitable acyl-ACP synthetase to form acyl-ACP in which the acyl group is bonded therewith with reference to literature such as The Journal of Biological Chemistry, 1979, vol. 254(15), p. 7123-7128.

The ACP, which can be preferably used in the present invention, can be appropriately selected from the normal ACP or proteins functionally equivalent to the ACP, according to a kind of host or the like. Specific examples thereof include an ACP derived from *Nannochloropsis oculata* (hereinafter, also referred to as "NoACP") (SEQ ID NO: 62). Moreover, as the proteins functionally equivalent to the ACP, a protein consisting of an amino acid sequence having 50% or more (preferably 70% or more, more preferably 80% or more, and further preferably 90% or more) identity with the amino acid sequence of the NoACP, and having ACP activity, can be also used. Examples of a gene encoding the NoACP include a gene consisting of a DNA consisting of the nucleotide sequence set forth in SEQ ID NO: 63; and a gene consisting of a DNA consisting of a nucleotide sequence having 50% or more (preferably 70% or more, more preferably 80% or more, and further preferably 90% or more) identity with the nucleotide sequence set forth in SEQ ID NO: 63, and encoding a protein having ACP activity.

Further, the transformants in which the expression of the ACP is enhanced (for example, the transformants in which the expression of the ACP gene is enhanced) can be prepared by an ordinary method. For example, the transformants can be prepared by a method similar to the above-described method for enhancing the expression of the desaturase gene, such as a method for introducing a gene encoding the ACP into a host, a method, in the host having a gene encoding the ACP on a genome, for modifying expression regulation regions of the gene, or the like.

Further, in the algae belonging to the genus *Nannochloropsis*, the ACP is preferably localized in the chloroplast. For example, it is more preferred to enhance expression of a gene in which a nucleotide sequence encoding a chloroplast transport signal functioning in the cell of the algae belonging to the genus *Nannochloropsis* is added to a nucleotide sequence of the ACP gene derived from the algae belonging to the genus *Nannochloropsis*. Alternatively, it is more preferred to introduce a gene encoding the ACP derived from the algae belonging to the genus *Nannochloropsis* into a chloroplast genome to enhance the expression of the gene introduced.

Moreover, in the transformant of the present invention, expression of a TE is preferably enhanced, and expression of a gene encoding a TE (hereinafter, also merely referred to as "TE gene") is more preferably enhanced.

As described above, TE is an enzyme that hydrolyzes the thioester bond of the acyl-ACP synthesized by a fatty acid synthase such as the KAS to produce a free fatty acid. The function of the TE terminates the fatty acid synthesis on the ACP, and then the thus-hydrolyzed fatty acid is supplied to the synthesis of PUFA or triacylglycerol or the like. Therefore, lipid productivity of the transformant to be used for the lipid production, particularly productivity of the fatty acids can be further improved by enhancing the expression of the TE, preferably by enhancing the expression of the TE gene.

The TE that can be used in the present invention needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE is considered to be an important factor in determining the fatty acid composition of an organism. In particular, when a host originally having no gene encoding a TE is used in the transformation, introduction of a gene encoding a TE, preferably a gene encoding a TE having substrate specificity to the long-chain acyl-ACP is effective. The productivity of PUFA is further improved by introducing such a gene.

The TE that can be used in the present invention can be appropriately selected from ordinary TEs and proteins functionally equivalent to the TEs, according to a kind of host or the like. Specific examples thereof include TE derived from *Nannochloropsis gaditana* (SEQ ID NO: 64); TE derived from *Nannochloropsis oculata* (SEQ ID NO: 65 or 67); and TE derived from *Nannochloropsis* granulate (SEQ ID NO: 66). Moreover, as the proteins functionally equivalent to them, a protein consisting of an amino acid sequence having 50% or more (preferably 70% or more, more preferably 80% or more, and further preferably 90% or more) identity with the amino acid sequence of any one of the TEs described above, and having TE activity, can be also used.

The transformants in which expression of the TE gene is enhanced can be prepared by an ordinary method. For example, the transformants can be prepared by a method similar to the above-mentioned method for enhancing expression of the each desaturase gene, such as a method of introducing the TE gene into a host, or a method, in a host having a TE gene on a genome, of modifying expression regulation regions of the gene.

In the transformant of the present invention, productivity of PUFA or lipids containing the same as components is improved in comparison with that in the host in which the expression of neither the Δ12-desaturase nor Δ6-desaturase is enhanced. Accordingly, if the transformant of the present invention is cultured under suitable conditions and then the PUFA or the lipids containing the same as components are collected from an obtained cultured product or an obtained growth product, the PUFA or the lipids containing the same as components can be efficiently produced. Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture conditions for the host can be employed. Further, from a viewpoint of the production efficiency of fatty acids, for example, precursor substances involved in the fatty acid biosynthesis system, such as glycerol, acetic acid, or glucose, may be added to the medium.

A medium based on natural seawater or artificial seawater, or a commercially available culture medium may be used for the medium used in the present invention. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the amount is preferably 1% (vol/vol) or more, per culture medium. The upper limit thereof is preferably 50% (vol/vol) or less, and more preferably 10% (vol/vol) or less. The range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10° C. or more, and more preferably 15° C. or more. The upper limit thereof is preferably 35° C. or less, and more preferably 30° C. or less. The range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably 100 lx or more, more preferably 300 lx or more, and further preferably 1,000 lx or more. The upper limit thereof is preferably 50,000 lx or less, more preferably 10,000 lx or less, and further preferably 6,000 lx or less. The range of irradiance during the lite irradiation is preferably 100 to 50,000 lx, more preferably 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 hours or more, and 10 hours or more. The upper limit thereof is preferably 24 hours or less, and 18 hours or less. The range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably 0.03% (which is the same degree as the concentration under atmospheric conditions) or more, more preferably 0.05% or more, further preferably 0.1% or more, and furthermore preferably 0.3% or more. The upper limit thereof is preferably 10% or less, more preferably 5% or less, further preferably 3% or less, and furthermore preferably 1% or less. The range of the concentration of carbon dioxide is preferably from 0.03 to 10%, more preferably from 0.05 to 5%, further preferably from 0.1 to 3%, and furthermore preferably from 0.3 to 1%. A concentration of carbonate is not particularly limited. When sodium hydrogen carbonate is used, for example, from viewpoints of the growth promotion and the improvement in the productivity of fatty acids, the concentration is preferably 0.01% by mass or more, more preferably 0.05% by mass or more, and further preferably 0.1% by mass or more. The upper limit thereof is preferably 5% by mass or less, more preferably 2% by mass or less, and further preferably 1% by mass or less. The range of the concentration of sodium hydrogen carbonate is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. The culture time is preferably 3 days or more, and more preferably 7 days or more. The upper limit thereof is preferably 90 days or less, and more preferably 30 days or less. The range of the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture is preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds, in view of usability thereof. The fatty acids ester compounds is preferably one kind selected from the group consisting of MAG, DAG and TAG, and more preferably TAG.

In view of usability for a surfactant or the like, and from a nutritional viewpoint, the fatty acid or the ester compound thereof contained in the lipid is preferably a PUFA having 18 or more carbon atoms or an ester compound thereof, more preferably a PUFA having 18 or 20 carbon atoms or an ester compound thereof, more preferably a PUFA having 20 carbon atoms or an ester compound thereof, more preferably a C20:3, a C20:4 or a C20:5, or an ester compound thereof, more preferably a dihomo-γ-linolenic acid, an arachidonic acid, or an eicosapentaenoic acid or an ester thereof, more preferably an arachidonic acid or an eicosapentaenoic acid or an ester thereof, and further preferably an eicosapentaenoic acid or an ester thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

The present invention also provides a kit for preparing the transformant of the algae belonging to the genus *Nannochloropsis*, the kit including a recombinant vector containing the Δ12-DES gene and a recombinant vector containing the Δ6-DES gene. The kit of the present invention can be used for preparing the transformant which is enhanced in the expression of the enzyme that catalyzes the reaction in the rate-limiting step in the synthetic pathway of PUFA, and is excellent in the productivity of PUFA or lipids containing the same as components. The kit of the present invention may also contain at least any one kind of recombinant vectors selected from the group consisting of the recombinant vectors containing the ω3-DES gene, the recombinant vector containing the Δ5-DES gene, the recombinant vector containing the Δ9-DES gene, or the recombinant vector containing the Δ6-ELO gene, preferably two or more kinds of recombinant vectors selected from the group consisting of the recombinant vector containing the ω3-DES gene, the recombinant vector containing the Δ5-DES gene, the recombinant vector containing the Δ9-DES gene.

In addition, the kit of the present invention may include, in addition to the above-described recombinant vector, a host, a reagent ordinarily used for transforming the host by the above-described vector, a buffer solution for transformation, and other elements necessary for detection in preparing the transformant, such as a reagent serving as an indicator for selecting the transformant.

With regard to the embodiments described above, the present invention also discloses methods of producing lipids, methods of modifying composition of fatty acids to be produced, transformants, methods of preparing transformants, and kits for preparing transformants, described below.

<1> A method of producing lipids, containing the steps of:
  culturing an alga belonging to the genus *Nannochloropsis*; and
  producing fatty acids or lipids containing the same as components;
wherein expressions of a Δ12-DES and a Δ6-DES, or expressions of a Δ12-DES gene and Δ6-DES gene are enhanced in the alga.

<2> A method of producing lipids, containing the steps of:
  enhancing expressions of a Δ12-DES and a Δ6-DES, or expressions of a Δ12-DES gene and a Δ6-DES gene in an alga belonging to the genus *Nannochloropsis*, and
  producing PUFA or lipids containing the same as components.

<3> A method of modifying the composition of fatty acids, containing the steps of:
  enhancing expressions of a Δ12-DES and a Δ6-DES, or expressions of a Δ12-DES gene and a Δ6-DES gene in an alga belonging to the genus *Nannochloropsis*, and
  increasing the proportion of PUFA in the whole fatty acids to be produced in a cell of the alga.

<4> A method of modifying the composition of fatty acids, containing the steps of:
  enhancing expressions of a Δ12-DES and a Δ6-DES, or expressions of a Δ12-DES gene and a Δ6-DES gene in an alga belonging to the genus *Nannochloropsis*, and
  increasing the proportion of PUFA residues in the whole fatty acid residues of fatty acid ester compounds, preferably at least any one kind selected from the group consisting of MAG, DAG and TAG, or more preferably TAG, to be produced in a cell of the alga.

<5> The method described in any one of the above items <1> to <4>, wherein the expressions of the Δ12-DES gene and the Δ6-DES gene are enhanced in a cell of the alga, to enhance the expressions of the Δ12-DES and the Δ6-DES.

<6> The method described in any one of the above items <1> to <5>, wherein the Δ12-DES gene and the Δ6-DES gene are introduced into the alga, to enhance the expressions of the Δ12-DES gene and the Δ6-DES gene introduced.

<7> The method described in any one of the above items <1> to <6>, wherein the Δ12-DES is any one of the following proteins (A) to (D), or preferably the following protein (A) or (B):

(A) a protein consisting of the amino acid sequence set forth in SEQ ID NO: 1;

(B) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (A), and having Δ12-DES activity;

(C) a protein consisting of the amino acid sequence set forth in SEQ ID NO: 45; and (D) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (C), and having Δ12-DES activity.

<8> The method described in the above item <7>, wherein the protein (B) consists of an amino acid sequence in which 1 or several, preferably 1 or more and 176 or less, more preferably 1 or more and 154 or less, further preferably 1 or more and 132 or less, furthermore preferably 1 or more and 110 or less, furthermore preferably 1 or more and 88 or less, furthermore preferably 1 or more and 66 or less, furthermore preferably 1 or more and 44 or less, furthermore preferably 1 or more and 36 or less, furthermore preferably 1 or more and 22 or less, furthermore preferably 1 or more and 9 or less, and furthermore preferably 1 or more and 5 or less amino acids, are deleted, substituted, inserted or added to the amino acid sequence of the protein (A).

<9> The method described in the above item <7>, wherein the protein (D) consists of an amino acid sequence in which 1 or several, preferably 1 or more and 181 or less, more preferably 1 or more and 159 or less, further preferably 1 or more and 136 or less, furthermore preferably 1 or more and 113 or less, furthermore preferably 1 or more and 91 or less, furthermore preferably 1 or more and 68 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less amino acids, are deleted, substituted, inserted or added to the amino acid sequence of the protein (C).

<10> The method described in any one of the above items <1> to <9>, wherein the gene encoding the Δ12-DES, or preferably encoding any one of the proteins (A) to (D) is a gene consisting of any one of the following DNAs (a) to (d), or preferably a gene consisting of the following DNA (a) or (b):

(a) a DNA consisting of the nucleotide sequence set forth in SEQ ID NO: 2;

(b) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (a), and encoding the protein having Δ12-DES activity;

(c) a DNA consisting of the nucleotide sequence set forth in SEQ ID NO: 46; and (d) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (c), and encoding the protein having Δ12-DES activity.

<11> The method described in the above item <10>, wherein the DNA (b) is a DNA consisting of a nucleotide sequence in which 1 or several, preferably 1 or more and 527 or less, more preferably 1 or more and 461 or less, further preferably 1 or more and 396 or less, furthermore preferably 1 or more and 330 or less, furthermore preferably 1 or more and 264 or less, furthermore preferably 1 or more and 198 or less, furthermore preferably 1 or more and 132 or less, furthermore preferably 1 or more and 106 or less, furthermore preferably 1 or more and 66 or less, furthermore preferably 1 or more and 27 or less, and furthermore preferably 1 or more and 14 or less nucleotides, are deleted, substituted, inserted or added to the nucleotide sequence of the DNA (a), and encoding the protein having Δ12-DES activity, or a DNA capable of hybridizing with a DNA consisting of the nucleotide sequence complementary with the DNA (a) under a stringent condition, and encoding the protein having Δ12-DES activity.

<12> The method described in the above item <10>, wherein the DNA (d) is a DNA consisting of a nucleotide sequence in which 1 or several, preferably 1 or more and 544 or less, more preferably 1 or more and 476 or less, further preferably 1 or more and 408 or less, furthermore preferably 1 or more and 340 or less, furthermore preferably 1 or more and 272 or less, furthermore preferably 1 or more and 204 or less, furthermore preferably 1 or more and 136 or less, furthermore preferably 1 or more and 109 or less, furthermore preferably 1 or more and 68 or less, furthermore preferably 1 or more and 28 or less, and furthermore preferably 1 or more and 14 or less nucleotides, are deleted, substituted, inserted or added to the nucleotide sequence of the DNA (c), and encoding the protein having Δ12-DES activity, or a DNA capable of hybridizing with a DNA consisting of the nucleotide sequence complementary with the DNA (c) under a stringent condition, and encoding the protein having Δ12-DES activity.

<13> The method described in any one of the above items <1> to <12>, wherein the Δ6-DES is any one of the following proteins (E) to (H), or preferably the following protein (E) or (F):

(E) a protein consisting of the amino acid sequence set forth in SEQ ID NO: 3;

(F) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (E), and having Δ6-DES activity;

(G) a protein consisting of the amino acid sequence set forth in SEQ ID NO: 47; and (H) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (G), and having Δ6-DES activity.

<14> The method described in the above item <13>, wherein the protein (F) consists of an amino acid sequence in which 1 or several, preferably 1 or more and 190 or less, more preferably 1 or more and 166 or less, further preferably 1 or more and 143 or less, furthermore preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less amino acids, are deleted, substituted, inserted or added to the amino acid sequence of the protein (E).

<15> The method described in the above item <13>, wherein the protein (H) consists of an amino acid sequence in which 1 or several, preferably 1 or more and 190 or less, more preferably 1 or more and 166 or less, further preferably 1 or more and 143 or less, furthermore preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less amino acids, are deleted, substituted, inserted or added to the amino acid sequence of the protein (G).

<16> The method described in any one of the above items <1> to <15>, wherein the gene encoding the Δ6-DES, or preferably encoding any one of the proteins (E) to (H) is a gene consisting of any one of the following DNAs (e) to (h), or preferably a gene consisting of the following DNA (e) or (f):

(e) a DNA consisting of the nucleotide sequence set forth in SEQ ID NO: 4;

(f) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (e), and encoding the protein having Δ6-DES activity;

(g) a DNA consisting of the nucleotide sequence set forth in SEQ ID NO: 48; and (h) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (g), and encoding the protein having Δ6-DES activity.

<17> The method described in the above item <16>, wherein the DNA (f) is a DNA consisting of a nucleotide sequence in which 1 or several, preferably 1 or more and 570 or less, more preferably 1 or more and 499 or less, further preferably 1 or more and 428 or less, furthermore preferably 1 or more and 357 or less, furthermore preferably 1 or more and 285 or less, furthermore preferably 1 or more and 214 or less, furthermore preferably 1 or more and 143 or less, furthermore preferably 1 or more and 114 or less, furthermore preferably 1 or more and 72 or less, furthermore preferably 1 or more and 29 or less, and furthermore preferably 1 or more and 15 or less nucleotides, are deleted, substituted, inserted or added to the nucleotide sequence of the DNA (e), and encoding the protein having Δ6-DES activity, or a DNA capable of hybridizing with a DNA consisting of the nucleotide sequence complementary with the DNA (e) under a stringent condition, and encoding the protein having Δ6-DES activity.

<18> The method described in the above item <16>, wherein the DNA (h) is a DNA consisting of a nucleotide sequence in which 1 or several, preferably 1 or more and 572 or less, more preferably 1 or more and 500 or less, further preferably 1 or more and 429 or less, furthermore preferably 1 or more and 357 or less, furthermore preferably 1 or more and 286 or less, furthermore preferably 1 or more and 215 or less, furthermore preferably 1 or more and 143 or less, furthermore preferably 1 or more and 115 or less, furthermore preferably 1 or more and 72 or less, furthermore preferably 1 or more and 29 or less, and furthermore preferably 1 or more and 15 or less nucleotides, are deleted, substituted, inserted or added to the nucleotide sequence of the DNA (g), and encoding the protein having Δ6-DES activity, or a DNA capable of hybridizing with a DNA consisting of the nucleotide sequence complementary with the DNA (g) under a stringent condition, and encoding the protein having Δ6-DES activity.

<19> The method described in any one of the above items <1> to <18>, wherein expression of an ω3-DES or expression of an ω3-DES gene is enhanced in the alga.

<20> The method described in the above item <19>, wherein the expression of the ω3-DES gene is enhanced in a cell of the alga, to enhance the expression of the ω3-DES.

<21> The method described in the above item <19> or <20>, wherein the ω3-DES gene is introduced into the alga, to enhance the expression of the ω3-DES gene introduced.

<22> The method described in any one of the above items <19> to <21>, wherein the ω3-DES is any one of the following proteins (I) to (L), or preferably the following protein (I) or (J):

(I) a protein consisting of the amino acid sequence set forth in SEQ ID NO: 5;

(J) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (I), and having ω3-DES activity;

(K) a protein consisting of the amino acid sequence set forth in SEQ ID NO: 49; and (L) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (K), and having ω3-DES activity.

<23> The method described in the above item <22>, wherein the protein (J) consists of an amino acid sequence in which 1 or several, preferably 1 or more and 164 or less, more preferably 1 or more and 144 or less, further preferably 1 or more and 123 or less, furthermore preferably 1 or more and 103 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less amino acids, are deleted, substituted, inserted or added to the amino acid sequence of the protein (I).

<24> The method described in the above item <22>, wherein the protein (L) consists of an amino acid sequence in which 1 or several, preferably 1 or more and 163 or less, more preferably 1 or more and 143 or less, further preferably 1 or more and 123 or less, furthermore preferably 1 or more and 102 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less amino acids, are deleted, substituted, inserted or added to the amino acid sequence of the protein (K).

<25> The method described in any one of the above items <19> to <24>, wherein the gene encoding the ω3-DES, or preferably encoding any one of the proteins (I) to (L) is a gene consisting of any one of the following DNAs (i) to (l), or preferably a gene consisting of the following DNA (i) or (j):

(i) a DNA consisting of the nucleotide sequence set forth in SEQ ID NO: 6;

(j) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (i), and encoding the protein having ω3-DES activity;

(k) a DNA consisting of the nucleotide sequence set forth in SEQ ID NO: 50; and (l) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (k), and encoding the protein having ω3-DES activity.

<26> The method described in the above item <25>, wherein the DNA (j) is a DNA consisting of a nucleotide sequence in which 1 or several, preferably 1 or more and 494 or less, more preferably 1 or more and 432 or less, further preferably 1 or more and 370 or less, furthermore preferably 1 or more and 309 or less, furthermore preferably 1 or more and 247 or less, furthermore preferably 1 or more and 185 or less, furthermore preferably 1 or more and 124 or less, furthermore preferably 1 or more and 99 or less, furthermore preferably 1 or more and 62 or less, furthermore preferably 1 or more and 25 or less, and furthermore preferably 1 or more and 13 or less nucleotides, are deleted, substituted, inserted or added to the nucleotide sequence of the DNA (i), and encoding the protein having ω3-DES activity, or a DNA capable of hybridizing with a DNA consisting of the nucleotide sequence complementary with the DNA (i) under a stringent condition, and encoding the protein having ω3-DES activity.

<27> The method described in the above item <25>, wherein the DNA (l) is a DNA consisting of a nucleotide sequence in which 1 or several, preferably 1 or more and 490 or less, more preferably 1 or more and 429 or less, further preferably 1 or more and 368 or less, furthermore preferably 1 or more and 306 or less, furthermore preferably 1 or more and 245 or less, furthermore preferably 1 or more and 184 or less, furthermore preferably 1 or more and 123 or less, furthermore preferably 1 or more and 98 or less, furthermore preferably 1 or more and 62 or less, furthermore preferably 1 or more and 25 or less, and furthermore preferably 1 or more and 13 or less nucleotides, are deleted, substituted, inserted or added to the nucleotide sequence of the DNA (k), and encoding the protein having ω3-DES activity, or a DNA capable of hybridizing with a DNA consisting of the nucleotide sequence complementary with the DNA (k) under a stringent condition, and encoding the protein having ω3-DES activity.

<28> The method described in any one of the above items <1> to <27>, wherein expression of a Δ5-DES or expression of a Δ5-DES gene is enhanced in the alga.

<29> The method described in the above item <28>, wherein the expression of the Δ5-DES gene is enhanced in a cell of the alga, to enhance the expression of the Δ5-DES.

<30> The method described in the above item <28> or <29>, wherein the Δ5-DES gene is introduced into the alga, to enhance the expression of the Δ5-DES gene introduced.

<31> The method described in any one of the above items <28> to <30>, wherein the Δ5-DES is any one of the following proteins (M) to (P), or preferably the following protein (M) or (N):

(M) a protein consisting of the amino acid sequence set forth in SEQ ID NO: 7;

(N) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (M), and having Δ5-DES activity;

(O) a protein consisting of the amino acid sequence set forth in SEQ ID NO: 51; and (P) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (O), and having Δ5-DES activity.

<32> The method described in the above item <31>, wherein the protein (N) consists of an amino acid sequence in which 1 or several, preferably 1 or more and 211 or less, more preferably 1 or more and 185 or less, further preferably 1 or more and 158 or less, furthermore preferably 1 or more and 132 or less, furthermore preferably 1 or more and 106 or less, furthermore preferably 1 or more and 79 or less, furthermore preferably 1 or more and 53 or less, furthermore preferably 1 or more and 43 or less, furthermore preferably 1 or more and 27 or less, furthermore preferably 1 or more and 11 or less, and furthermore preferably 1 or more and 6 or less amino acids, are deleted, substituted, inserted or added to the amino acid sequence of the protein (M).

<33> The method described in the above item <31>, wherein the protein (P) consists of an amino acid sequence in which 1 or several, preferably 1 or more and 206 or less, more preferably 1 or more and 181 or less, further preferably 1 or more and 155 or less, furthermore preferably 1 or more and 129 or less, furthermore preferably 1 or more and 103 or less, furthermore preferably 1 or more and 78 or less, furthermore preferably 1 or more and 52 or less, furthermore preferably 1 or more and 42 or less, furthermore preferably 1 or more and 26 or less, furthermore preferably 1 or more and 11 or less, and furthermore preferably 1 or more and 6 or less amino acids, are deleted, substituted, inserted or added to the amino acid sequence of the protein (O).

<34> The method described in any one of the above items <28> to <33>, wherein the gene encoding the Δ5-DES, or preferably encoding any one of the proteins (M) to (P) is a gene consisting of any one of the following DNAs (m) to (p), or preferably a gene consisting of the following DNA (m) or (n):

(m) a DNA consisting of the nucleotide sequence set forth in SEQ ID NO: 8;

(n) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (m), and encoding the protein having Δ5-DES activity;

(o) a DNA consisting of the nucleotide sequence set forth in SEQ ID NO: 52; and (p) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (o), and encoding the protein having Δ5-DES activity.

<35> The method described in the above item <34>, wherein the DNA (n) is a DNA consisting of a nucleotide sequence in which 1 or several, preferably 1 or more and 633 or less, more preferably 1 or more and 554 or less, further preferably 1 or more and 475 or less, furthermore preferably 1 or more and 396 or less, furthermore preferably 1 or more and 317 or less, furthermore preferably 1 or more and 238 or less, furthermore preferably 1 or more and 159 or less, furthermore preferably 1 or more and 127 or less, furthermore preferably 1 or more and 80 or less, furthermore preferably 1 or more and 32 or less, and furthermore preferably 1 or more and 16 or less nucleotides, are deleted, substituted, inserted or added to the nucleotide sequence of the DNA (m), and encoding the protein having Δ5-DES activity, or a DNA capable of hybridizing with a DNA consisting of the nucleotide sequence complementary with the DNA (m) under a stringent condition, and encoding the protein having Δ5-DES activity.

<36> The method described in the above item <34>, wherein the DNA (p) is a DNA consisting of a nucleotide sequence in which 1 or several, preferably 1 or more and 620 or less, more preferably 1 or more and 542 or less, further preferably 1 or more and 465 or less, furthermore preferably 1 or more and 387 or less, furthermore preferably 1 or more and 310 or less, furthermore preferably 1 or more and 233 or less, furthermore preferably 1 or more and 155 or less, furthermore preferably 1 or more and 124 or less, furthermore preferably 1 or more and 78 or less, furthermore preferably 1 or more and 31 or less, and furthermore preferably 1 or more and 16 or less nucleotides, are deleted, substituted, inserted or added to the nucleotide sequence of the DNA (o), and encoding the protein having Δ5-DES activity, or a DNA capable of hybridizing with a DNA consisting of the nucleotide sequence complementary with the DNA (o) under a stringent condition, and encoding the protein having Δ5-DES activity.

<37> The method described in any one of the above items <1> to <36>, wherein expression of a Δ9-DES or expression of a Δ9-DES gene is enhanced in the alga.

<38> The method described in the above item <37>, wherein the expression of the Δ9-DES gene is enhanced in a cell of the alga, to enhance the expression of the Δ9-DES.

<39> The method described in the above item <37> or <38>, wherein the Δ9-DES gene is introduced into the alga, to enhance the expression of the Δ9-DES gene introduced.

<40> The method described in any one of the above items <37> to <39>, wherein the Δ9-DES is any one of the following proteins (Q) to (T), or preferably the following protein (Q) or (R):

(Q) a protein consisting of the amino acid sequence set forth in SEQ ID NO: 9;

(R) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (Q), and having Δ9-DES activity;

(S) a protein consisting of the amino acid sequence set forth in SEQ ID NO: 53; and (T) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (S), and having Δ9-DES activity.

<41> The method described in the above item <40>, wherein the protein (R) consists of an amino acid sequence in which 1 or several, preferably 1 or more and 144 or less, more preferably 1 or more and 126 or less, further preferably 1 or more and 108 or less, furthermore preferably 1 or more and 90 or less, furthermore preferably 1 or more and 72 or less, furthermore preferably 1 or more and 54 or less, furthermore preferably 1 or more and 36 or less, furthermore preferably 1 or more and 29 or less, furthermore preferably 1 or more and 18 or less, furthermore preferably 1 or more and 8 or less, and furthermore preferably 1 or more and 4 or less amino acids, are deleted, substituted, inserted or added to the amino acid sequence of the protein (Q).

<42> The method described in the above item <40>, wherein the protein (T) consists of an amino acid sequence in which 1 or several, preferably 1 or more and 136 or less, more preferably 1 or more and 119 or less, further preferably 1 or more and 102 or less, furthermore preferably 1 or more and 85 or less, furthermore preferably 1 or more and 68 or less, furthermore preferably 1 or more and 51 or less, furthermore preferably 1 or more and 34 or less, furthermore preferably 1 or more and 28 or less, furthermore preferably 1 or more and 17 or less, furthermore preferably 1 or more and 7 or less, and furthermore preferably 1 or more and 4 or less amino acids, are deleted, substituted, inserted or added to the amino acid sequence of the protein (S).

<43> The method described in any one of the above items <37> to <42>, wherein the gene encoding the Δ9-DES, or preferably encoding any one of the proteins (Q) to (T) is a gene consisting of any one of the following DNAs (q) to (t), or preferably a gene consisting of the following DNA (q) or (r):

(q) a DNA consisting of the nucleotide sequence set forth in SEQ ID NO: 10;

(r) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (q), and encoding the protein having Δ9-DES activity;

(s) a DNA consisting of the nucleotide sequence set forth in SEQ ID NO: 54; and (t) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (s), and encoding the protein having Δ9-DES activity.

<44> The method described in the above item <43>, wherein the DNA (r) is a DNA consisting of a nucleotide sequence in which 1 or several, preferably 1 or more and 432 or less, more preferably 1 or more and 378 or less, further preferably 1 or more and 324 or less, furthermore preferably 1 or more and 270 or less, furthermore preferably 1 or more and 216 or less, furthermore preferably 1 or more and 162 or less, furthermore preferably 1 or more and 108 or less, furthermore preferably 1 or more and 87 or less, furthermore preferably 1 or more and 54 or less, furthermore preferably 1 or more and 22 or less, and furthermore preferably 1 or more and 11 or less nucleotides, are deleted, substituted, inserted or added to the nucleotide sequence of the DNA (q), and encoding the protein having Δ9-DES activity, or a DNA capable of hybridizing with a DNA consisting of the nucleotide sequence complementary with the DNA (q) under a stringent condition, and encoding the protein having Δ9-DES activity.

<45> The method described in the above item <43>, wherein the DNA (t) is a DNA consisting of a nucleotide sequence in which 1 or several, preferably 1 or more and 410 or less, more preferably 1 or more and 359 or less, further preferably 1 or more and 307 or less, furthermore preferably 1 or more and 256 or less, furthermore preferably 1 or more and 205 or less, furthermore preferably 1 or more and 154 or less, furthermore preferably 1 or more and 103 or less, furthermore preferably 1 or more and 82 or less, furthermore preferably 1 or more and 52 or less, furthermore preferably 1 or more and 21 or less, and furthermore preferably 1 or more and 11 or less nucleotides, are deleted, substituted, inserted or added to the nucleotide sequence of the DNA (s), and encoding the protein having Δ9-DES activity, or a DNA capable of hybridizing with a DNA consisting of the nucleotide sequence complementary with the DNA (s) under a stringent condition, and encoding the protein having Δ9-DES activity.

<46> The method described in any one of the above items <1> to <45>, wherein expression of a Δ6-ELO or expression of a Δ6-ELO gene is enhanced in the alga.

<47> The method described in the above item <46>, wherein the expression of the Δ6-ELO gene is enhanced in a cell of the alga, to enhance the expression of the Δ6-ELO.

<48> The method described in the above item <46> or <47>, wherein the Δ6-ELO gene is introduced into the alga, to enhance the expression of the Δ6-ELO gene introduced.

<49> The method described in any one of the above items <46> to <48>, wherein the Δ6-ELO is the following protein (U) or (V):

(U) a protein consisting of the amino acid sequence set forth in SEQ ID NO: 74; and (V) a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (U), and having Δ6-ELO activity.

<50> The method described in the above item <49>, wherein the protein (V) consists of an amino acid sequence in which 1 or several, preferably 1 or more and 111 or less, more preferably 1 or more and 97 or less, further preferably 1 or more and 83 or less, furthermore preferably 1 or more and 69 or less, furthermore preferably 1 or more and 56 or less, furthermore preferably 1 or more and 42 or less, furthermore preferably 1 or more and 28 or less, furthermore preferably 1 or more and 23 or less, furthermore preferably 1 or more and 14 or less, furthermore preferably 1 or more and 6 or less, and furthermore preferably 1 or more and 3 or less amino acids, are deleted, substituted, inserted or added to the amino acid sequence of the protein (U).

<51> The method described in any one of the above items <46> to <50>, wherein the gene encoding the Δ6-ELO, or preferably any one of the proteins (U) and (V) is a gene consisting of any one of the following DNAs (u) and (v):

(u) a DNA consisting of the nucleotide sequence set forth in SEQ ID NO: 73;

(v) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (u), and encoding the protein having Δ6-ELO activity.

<52> The method described in the above item <51>, wherein the DNA (v) is a DNA consisting of a nucleotide sequence in which 1 or several, preferably 1 or more and 333 or less, more preferably 1 or more and 291 or less, further preferably 1 or more and 250 or less, furthermore preferably 1 or more and 208 or less, furthermore preferably 1 or more and 167 or less, furthermore preferably 1 or more and 125 or less, furthermore preferably 1 or more and 84 or less, furthermore preferably 1 or more and 67 or less, furthermore preferably 1 or more and 42 or less, furthermore preferably 1 or more and 17 or less, and furthermore preferably 1 or more and 9 or less nucleotides, are deleted, substituted, inserted or added to the nucleotide sequence of the DNA (u), and encoding the protein having Δ6-ELO activity, or a DNA capable of hybridizing with a DNA consisting of the nucleotide sequence complementary with the DNA (u) under a stringent condition, and encoding the protein having Δ6-ELO activity.

<53> The method described in any one of the above items <1> to <52>, wherein, in the alga, expression of at least any one kind of enzymes selected from the group consisting of an ω3-DES, a Δ5-DES, a Δ9-DES and a Δ6-ELO, preferably any two or more kinds of enzymes selected from the group consisting of an ω3-DES, a Δ5-DES, a Δ9-DES and a Δ6-ELO, or genes encoding the same is enhanced.

<54> The method described in any one of the above items <1> to <53>, wherein, in the alga, at least any one of the proteins selected from the group consisting of a KAS II, an ACP and a TE, preferably a gene encoding at least any one of the proteins selected from the group consisting of a KAS II, an ACP and a TE is enhanced.

<55> The method described in the above item <54>, wherein the gene encoding at least any one of the proteins selected from the group consisting of the KAS II, the ACP and the TE is introduced into the alga, to enhance the expression of the gene introduced.

<56> The method described in the above item <54> or <55>, wherein the KAS II is a protein consisting of the amino acid sequence set forth in SEQ ID NO: 60, or a protein consisting of an amino acid sequence having 50% or more, preferably 70% or more, more preferably 80% or more, or more preferably 90% or more identity with the amino acid sequence set forth in SEQ ID NO: 60, and having KAS activity.

<57> The method described in any one of the above items <54> to <56>, wherein the gene encoding the KAS II is a gene consisting of a DNA consisting of the nucleotide sequence set forth in SEQ ID NO: 61, or a gene consisting of a nucleotide sequence having 50% or more, preferably 70% or more, more preferably 80% or more, or more preferably 90% or more identity with the nucleotide sequence set forth in SEQ ID NO: 61, and encoding a protein having KAS activity.

<58> The method described in the above item <54> or <55>, wherein the ACP is a protein consisting of the amino acid sequence set forth in SEQ ID NO: 62, or a protein consisting of an amino acid sequence having 50% or more, preferably 70% or more, more preferably 80% or more, or more preferably 90% or more identity with the amino acid sequence set forth in SEQ ID NO: 62, and having ACP activity.

<59> The method described in any one of the above items <54>, <55> and <58>, wherein the gene encoding the ACP is a gene consisting of a DNA consisting of the nucleotide sequence set forth in SEQ ID NO: 63, or a gene consisting of a nucleotide sequence having 50% or more, preferably 70% or more, more preferably 80% or more, or more preferably 90% or more identity with the nucleotide sequence set forth in SEQ ID NO: 63, and encoding a protein having ACP activity.

<60> The method described in any one of the above items <54>, <55>, <58> and <59>, wherein the gene encoding the ACP is a gene to which a nucleotide sequence encoding a chloroplast transit signal sequence functioning in the cell of the algae is added.

<61> The method described in any one of the above items <54>, <55>, <58> and <59>, wherein the gene encoding the ACP is introduced into a chloroplast genome to enhance the expression of the gene introduced.

<62> The method described in the above item <54> or <55>, wherein the TE is a protein consisting of any one of the amino acid sequences set forth in SEQ ID NO: 64 to 67, of a protein functionally equivalent thereto.

<63> The method described in any one of the above items <54>, <55> and <62>, wherein the TE is a protein consisting of any one of the amino acid sequences set forth in SEQ ID NO: 64 to 67, or a protein consisting of an amino acid sequence having 50% or more, preferably 70% or more, more preferably 80% or more, or more preferably 90% or more identity with any one of the amino acid sequences set forth in SEQ ID NO: 64 to 67, and having TE activity.

<64> The method described in any one of the above items <1> to <63>, wherein the alga is *Nannochloropsis oculata, Nannochloropsis gaditana, Nannochloropsis salina, Nannochloropsis oceanica, Nannochloropsis atomus, Nannochloropsis maculata, Nannochloropsis granulata*, or *Nannochloropsis* sp., preferably *Nannochloropsis oculata* or *Nannochloropsis gaditana*, or more preferably *Nannochloropsis oculata*.

<65> The method described in any one of the above items <1> to <64>, wherein the fatty acids or lipids contain a PUFA having 18 or more carbon atoms or an ester compound thereof, preferably a PUFA having 18 or 20 carbon atoms or an ester compound thereof, more preferably a PUFA having 20 carbon atoms or an ester compound thereof, more preferably a C20:3, a C20:4 or a C20:5, or an ester compound thereof, more preferably a dihomo-γ-linolenic acid, an arachidonic acid, or an eicosapentaenoic acid or an ester thereof, more preferably an arachidonic acid or an eicosapentaenoic acid or an ester thereof, or further preferably an eicosapentaenoic acid or an ester thereof.

<66> The method described in any one of the above items <1> to <65>, wherein the alga is cultured by using f/2 media.

<67> A transformant of an alga belonging to the genus *Nannochloropsis*, wherein expressions of a Δ12-DES and a Δ6-DES, or expressions of a Δ12-DES gene and a Δ6-DES gene are enhanced in a host cell.

<68> The transformant described in the above item <67>, wherein the expressions of the Δ12-DES gene and the Δ6-DES gene are enhanced in a cell of the alga, and the expressions of the Δ12-DES and the Δ6-DES are enhanced.

<69> The transformant described in the above item <68>, containing the Δ12-DES gene and the Δ6-DES gene, or a recombinant vector containing the Δ12-DES gene and a recombinant vector containing the Δ6-DES gene.

<70> A method of preparing a transformant, containing the step of introducing a Δ12-DES gene and a Δ6-DES gene, or a recombinant vector containing a Δ12-DES gene and a recombinant vector containing a Δ6-DES gene into an alga belonging to the genus *Nannochloropsis*.

<71> A kit for preparing a transformant of alga belonging to the genus *Nannochloropsis*, containing a recombinant vector containing a Δ12-DES gene and a recombinant vector containing a Δ6-DES gene.

<72> The transformant, the method of preparing the same, or the kit for preparing the transformant described in any one of the above items <67> to <71>, wherein the Δ12-DES is any one of the proteins (A) to (D), or preferably the protein (A) or (B).

<73> The transformant, the method of preparing the same, or the kit for preparing the transformant described in the above item <72>, wherein the protein (B) or (D) is a protein specified in any one of the above items <7> to <9>.

<74> The transformant, the method of preparing the same, or the kit for preparing the transformant described in any one of the above items <67> to <73>, wherein a gene encoding the Δ12-DES, or preferably encoding any one of the proteins (A) to (D) is a gene specified in any one of the above items <10> to <12>.

<75> The transformant, the method of preparing the same, or the kit for preparing the transformant described in any one of the above items <67> to <74>, wherein the Δ6-DES is any one of the proteins (E) to (H), or preferably the protein (E) or (F).

<76> The transformant, the method of preparing the same, or the kit for preparing the transformant described in the above item <75>, wherein the protein (F) or (H) is a protein specified in any one of the above items <13> to <15>.

<77> The transformant, the method of preparing the same, or the kit for preparing the transformant described in any one of the above items <67> to <76>, wherein a gene encoding the Δ6-DES, or preferably encoding any one of the proteins (E) to (H) is a gene specified in any one of the above items <16> to <18>.

<78> The transformant described in any one of the above items <67> to <69> and <72> to <77>, wherein expression of an ω3-DES or expression of an ω3-DES gene is enhanced in the transformant.

<79> The transformant described in the above item <78>, wherein the expression of the ω3-DES gene is enhanced in a cell of the alga, and the expression of the ω3-DES is enhanced.

<80> The transformant described in the above item <79>, containing the ω3-DES gene, or a recombinant vector containing the ω3-DES gene.

<81> The method of preparing a transformant described in any one of the above items <70> and <72> to <77>, wherein an ω3-DES gene, or a recombinant vector containing an ω3-DES gene is introduced into the alga.

<82> The kit for preparing a transformant described in any one of the above items <71> to <77>, containing a recombinant vector containing an ω3-DES gene.

<83> The transformant, the method of preparing the same, or the kit for preparing the transformant described in any one of the above items <78> to <82>, wherein the ω3-DES is any one of the proteins (I) to (L), or preferably the protein (I) or (J).

<84> The transformant, the method of preparing the same, or the kit for preparing the transformant described in the above item <83>, wherein the protein (J) or (L) is a protein specified in any one of the above items <22> to <24>.

<85> The transformant, the method of preparing the same, or the kit for preparing the transformant described in any one of the above items <78> to <84>, wherein a gene encoding the ω3-DES, or preferably encoding any one of the proteins (I) to (L) is a gene specified in any one of the above items <25> to <27>.

<86> The transformant described in any one of the above items <67> to <69>, <72> to <80> and <83> to <85>, wherein expression of a Δ5-DES or expression of a Δ5-DES gene is enhanced in the transformant.

<87> The transformant described in the above item <86>, wherein the expression of the Δ5-DES gene is enhanced in a cell of the alga, and the expression of the Δ5-DES is enhanced.

<88> The transformant described in the above item <87>, containing the Δ5-DES gene, or a recombinant vector containing the Δ5-DES gene.

<89> The method of preparing a transformant described in any one of the above items <70>, <72> to <77>, <81> and <83> to <85>, wherein a Δ5-DES gene, or a recombinant vector containing a Δ5-DES gene is introduced into the alga.

<90> The kit for preparing a transformant described in any one of the above items <71> to <77> and <82> to <85>, containing a recombinant vector containing a Δ5-DES gene.

<91> The transformant, the method of preparing the same, or the kit for preparing the transformant described in any one of the above items <86> to <90>, wherein the Δ5-DES is any one of the proteins (M) to (P), or preferably the protein (M) or (N).

<92> The transformant, the method of preparing the same, or the kit for preparing the transformant described in the above item <91>, wherein the protein (N) or (P) is a protein specified in any one of the above items <31> to <33>.

<93> The transformant, the method of preparing the same, or the kit for preparing the transformant described in any one of the above items <86> to <92>, wherein a gene encoding the Δ5-DES, or preferably encoding any one of the proteins (M) to (P) is a gene specified in any one of the above items <34> to <36>.

<94> The transformant described in any one of the above items <67> to <69>, <72> to <80>, <83> to <88> and <91> to <93>, wherein expression of a Δ9-DES or expression of a Δ9-DES gene is enhanced in the transformant.

<95> The transformant described in the above item <94>, wherein the expression of the Δ9-DES gene is enhanced in a cell of the alga, and the expression of the Δ9-DES is enhanced.

<96> The transformant described in the above item <95>, containing the Δ9-DES gene, or a recombinant vector containing the Δ9-DES gene.

<97> The method of preparing a transformant described in any one of the above items <70>, <72> to <77>, <81>, <83> to <85>, <89> and <91> to <93>, wherein a Δ9-DES gene, or a recombinant vector containing a Δ9-DES gene is introduced into the alga.

<98> The kit for preparing a transformant described in any one of the above items <71> to <77>, <82> to <85> and <90> to <93>, containing a recombinant vector containing a Δ9-DES gene.

<99> The transformant, the method of preparing the same, or the kit for preparing the transformant described in any one of the above items <94> to <98>, wherein the Δ9-DES is any one of the proteins (Q) to (T), or preferably the protein (Q) or (R).

<100> The transformant, the method of preparing the same, or the kit for preparing the transformant described in the above item <99>, wherein the protein (R) or (T) is a protein specified in any one of the above items <40> to <42>.

<101> The transformant, the method of preparing the same, or the kit for preparing the transformant described in any one of the above items <94> to <100>, wherein a gene encoding the Δ9-DES, or preferably encoding any one of the proteins (Q) to (T) is a gene specified in any one of the above items <43> to <45>.

<102> The transformant described in any one of the above items <67> to <69>, <72> to <80>, <83> to <88>, <91> to <96> and <99> to <101>, wherein expression of a Δ6-ELO or expression of a Δ6-ELO gene is enhanced in the transformant.

<103> The transformant described in the above item <102>, wherein the expression of the Δ6-ELO gene is enhanced in a cell of the alga, and the expression of the Δ6-ELO is enhanced.

<104> The transformant described in the above item <103>, containing the Δ6-ELO gene, or a recombinant vector containing the Δ6-ELO gene.

<105> The method of preparing a transformant described in any one of the above items <70>, <72> to <77>, <81>, <83> to <85>, <89>, <91> to <93>, <97> and <99> to <101>, wherein a Δ6-ELO gene, or a recombinant vector containing a Δ6-ELO gene is introduced into the alga.

<106> The kit for preparing a transformant described in any one of the above items <71> to <77>, <82> to <85>, <90> to <93> and <98> to <101>, containing a recombinant vector containing a Δ6-ELO gene.

<107> The transformant, the method of preparing the same, or the kit for preparing the transformant described in any one of the above items <102> to <106>, wherein the Δ6-ELO is any one of the proteins (U) and (V).

<108> The transformant, the method of preparing the same, or the kit for preparing the transformant described in the above item <107>, wherein the protein (V) is a protein specified in the above item <49> or <50>.

<109> The transformant, the method of preparing the same, or the kit for preparing the transformant described in any one of the above items <102> to <108>, wherein a gene encoding the 6-ELO, or preferably encoding any one of the proteins (U) and (V) is a gene specified in the above item <51> or <52>.

<110> The transformant described in any one of the above items <67> to <69>, <72> to <80>, <83> to <88>, <91> to <96>, <99> to <104> and <107> to <109>, wherein expression of at least any one kind of enzymes selected from the group consisting of an ω3-DES, a Δ5-DES, a Δ9-DES and a Δ6-ELO, or preferably any two or more kinds of enzymes selected from the group consisting of an ω3-DES, a Δ5-DES, a Δ9-DES and a Δ6-ELO, or genes encoding the same is enhanced.

<111> The method of preparing a transformant described in any one of the above items <70>, <72> to <77>, <81>, <83> to <85>, <89>, <91> to <93>, <97>, <99> to <101>, <105> and <107> to <109>, wherein at least any one kind of the genes selected from the group consisting of an ω3-DES gene, a Δ5-DES gene, a Δ9-DES gene and a Δ6-ELO gene, or preferably any two or more kinds of genes selected from the group consisting of an ω3-DES gene, a Δ5-DES gene, a Δ9-DES gene and a Δ6-ELO gene or a recombinant vector containing the gene is introduced.

<112> The kit for preparing a transformant described in any one of the above items <71> to <77>, <82> to <85>, <90> to <93>, <98> to <101> and <106> to <109>, containing at least any one kind of recombinant vectors selected from the group consisting of a recombinant vector containing an ω3-DES gene, a recombinant vector containing a Δ5-DES gene, a recombinant vector containing a Δ9-DES gene and a recombinant vector containing a Δ6-ELO gene, or preferably any two or more kinds of recombinant vectors selected from the group consisting of a recombinant vector containing an ω3-DES gene, a recombinant vector containing a Δ5-DES gene, a recombinant vector containing a Δ9-DES gene and a recombinant vector containing a Δ6-ELO gene.

<113> The transformant or the method of preparing the same described in any one of the above items <67> to <70>, <72> to <81>, <83> to <89>, <91> to <97>, <99> to <105> and <107> to <112>, wherein expression of at least any one of the proteins selected from the group consisting of a KAS II, an ACP and a TE, or preferably expression of a gene encoding at least any one selected from the group consisting of a KAS II, an ACP and a TE is enhanced in the transformant.

<114> The transformant or the method of preparing the same described in the above item <113>, wherein the gene is introduced into the alga, and the expression of the gene introduced is enhanced in a cell of the alga.

<115> The kit for preparing a transformant described in any one of the above items <71> to <77>, <82> to <85>, <90> to <93>, <98> to <101>, <106> to <109> and <112>, containing at least any one of the recombinant vectors selected from the group consisting of a recombinant vector containing a gene encoding a KAS II, a recombinant vector containing a gene encoding an ACP and a recombinant vector containing a gene encoding a TE.

<116> The transformant, the method of preparing the same, or the kit for preparing the transformant described in any one of the above items <113> to <115>, wherein the KAS II is a protein specified in the above item <56>.

<117> The transformant, the method of preparing the same, or the kit for preparing the transformant described in any one of the above items <113> to <116>, wherein a gene encoding the KAS II is a gene specified in the above item <57>.

<118> The transformant, the method of preparing the same, or the kit for preparing the transformant described in any one of the above items <113> to <117>, wherein the ACP is a protein specified in the above item <58>.

<119> The transformant, the method of preparing the same, or the kit for preparing the transformant described in any one of the above items <113> to <118>, wherein a gene encoding the ACP is a gene specified in the above item <59>.

<120> The transformant, the method of preparing the same, or the kit for preparing the transformant described in any one of the above items <113> to <119>, wherein a gene encoding the ACP is a gene to which a nucleotide sequence encoding a chloroplast transit signal functioning in the cell of the algae is added.

<121> The transformant, the method of preparing the same, or the kit for preparing the transformant described in any one of the above items <113> to <119>, wherein a gene encoding the ACP is introduced into a chloroplast genome to enhance the expression of the introduced gene.

<122> The transformant, the method of preparing the same, or the kit for preparing the transformant described in any one of the above items <113> to <121>, wherein the TE is a protein specified in the above item <62> or <63>.

<123> The transformant, the method of preparing the same, or the kit for preparing the transformant described in any one of the above items <67> to <122>, wherein the alga is *Nannochloropsis oculata, Nannochloropsis gaditana, Nannochloropsis salina, Nannochloropsis oceanica, Nannochloropsis atomus, Nannochloropsis maculata, Nannochloropsis granulata*, or *Nannochloropsis* sp., preferably *Nannochloropsis oculata* or *Nannochloropsis gaditana*, or more preferably *Nannochloropsis oculata.*

<124> Use of the transformant, the transformant prepared by the method of producing the same, or the kit for preparing the transformant described in any one of the above items <67> to <123>, for producing lipids.

<125> The use described in the above item <124>, wherein the lipids contain a PUFA having 18 or more carbon atoms or an ester compound thereof, preferably a PUFA 18 or 20 carbon atoms or an ester compound thereof, more preferably a PUFA having 20 carbon atoms or an ester compound thereof, further preferably a C20:3, a C20:4 or a C20:5 or an ester compound thereof, furthermore preferably a dihomo-γ-linolenic acid, an arachidonic acid, or an eicosapentaenoic acid or an ester compound thereof, furthermore preferably an arachidonic acid, an eicosapentaenoic acid or an ester compound thereof, or an eicosapentaenoic acid or an ester compound thereof.

<126> The method described in the above item <65> or the use described in the above item <125>, wherein the fatty acid ester compound is at least any one kind selected from the group consisting of MAG, DAG and TAG, or preferably TAG.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| Primer No | Sequence (5' → 3') | SEQ ID NO |
| --- | --- | --- |
| 13 | CTTTTTTGTGAAGCAATGGCCAAGTTGACCAGTGCCG | SEQ ID NO: 13 |
| 14 | TTTCCCCCATCCCGATTAGTCCTGCTCCTCGGCCAC | SEQ ID NO: 14 |
| 15 | CGAGCTCGGTACCCGACTGCGCATGGATTGACCGA | SEQ ID NO: 15 |
| 16 | TGCTTCACAAAAAAGACAGCTTCTTGAT | SEQ ID NO: 16 |
| 17 | TCGGGATGGGGGAAAAAAACCTCTG | SEQ ID NO: 17 |
| 18 | ACTCTAGAGGATCCCCTTTCGTAAATAAATCAGCTC | SEQ ID NO: 18 |
| 20 | GGGATCCTCTAGAGTCGACC | SEQ ID NO: 20 |
| 21 | CGGGTACCGAGCTCGAATTC | SEQ ID NO: 21 |
| 22 | CAGCCCGCATCAACAATGGTCTTCCAGCTCGCCCG | SEQ ID NO: 22 |
| 23 | CTCTTCCACAGAAGCTTAGTTGTACTTGGGGTGATTGC | SEQ ID NO: 23 |
| 24 | CAGCCCGCATCAACAATGGGACGCGGCGGTGAGAA | SEQ ID NO: 24 |
| 25 | CTCTTCCACAGAAGCCTATGCCCGCTGCTTGTAGA | SEQ ID NO: 25 |
| 26 | CAGCCCGCATCAACAATGGGACGCGGTGGCGAGCG | SEQ ID NO: 26 |
| 27 | CTCTTCCACAGAAGCTTACATGGCGGGGAAATCGG | SEQ ID NO: 27 |
| 28 | CAGCCCGCATCAACAATGCCTCCCCAGAACGACGC | SEQ ID NO: 28 |
| 29 | CTCTTCCACAGAAGCCTAACCCATGTGCACCTCCG | SEQ ID NO: 29 |
| 30 | CAGCCCGCATCAACAATGGTTGAGCAAACGTTACC | SEQ ID NO: 30 |
| 31 | CTCTTCCACAGAAGCTTACGGAGGGGAGGATGAAC | SEQ ID NO: 31 |
| 32 | CGAGCTCGGTACCCGTTCTTCCGCTTGTTGCTGCC | SEQ ID NO: 32 |
| 33 | TGTTGATGCGGGCTGAGATTGGTGG | SEQ ID NO: 33 |
| 34 | GCTTCTGTGGAAGAGCCAGTG | SEQ ID NO: 34 |
| 35 | GGCAAGAAAAGCTGGGGGAAAAGACAGG | SEQ ID NO: 35 |
| 38 | CCAGCTTTTCTTGCCACTGCGCATGGATTGACCGA | SEQ ID NO: 38 |

TABLE 2

| Primer No | Sequence (5' → 3') | SEQ ID NO |
| --- | --- | --- |
| 40 | CTTTTTTGTGAAGCAATGGTCGAGATTCGAAGCAT | SEQ ID NO: 40 |
| 41 | TTTCCCCCATCCCGATCAGAAGAACTCGTCCAACA | SEQ ID NO: 41 |
| 43 | CTTTTTTGTGAAGCAATGACACAAGAATCCCTGTTAC | SEQ ID NO: 43 |
| 44 | TTTCCCCCATCCCGATCAGGCGCCGGGGGCGGTGTC | SEQ ID NO: 44 |
| 69 | CTTTTTTGTGAAGCAATGAGCCCAGAACGACGCCC | SEQ ID NO: 69 |

TABLE 2-continued

| Primer No | Sequence (5' → 3') | SEQ ID NO |
|---|---|---|
| 70 | TTTCCCCCATCCCGATCAGATCTCGGTGACGGGCAGG | SEQ ID NO: 70 |
| 71 | CAGCCCGCATCAACAATGGCCGCCGCCCTTCTTGCAG | SEQ ID NO: 71 |
| 72 | CTCTTCCACAGAAGCTTAAGCCTTCTTGGAAACCGG | SEQ ID NO: 72 |

Example 1 Preparation of a Plasmid for Expression of Desaturase Gene Derived from *Nannochloropsis oculata*, Transformation of *Nannochloropsis oculata*, and Production of Lipids by the Transformant (1) Construction of Plasmid for Zeocin Resistance Gene Expression A zeocin resistance gene (SEQ ID NO: 11), and a tubulin promoter sequence (SEQ ID NO: 12) derived from *Nannochloropsis gaditana* strain CCMP 526 described in a literature (Nature Communications, DOI:10.1038/ncomms1688, 2012) were artificially synthesized. Using the thus-synthesized DNA fragments as a template, and a pair of the primer Nos. 13 and 14 shown in Table 1, and a pair of the primer Nos. 15 and 16 shown in Table 1, PCR were carried out, to amplify the zeocin resistance gene and the tubulin promoter sequence, respectively.

Further, using a genome of *Nannochloropsis oculata* strain NIES-2145 as a template, and a pair of the primer Nos. 17 and 18 shown in Table 1, PCR was carried out to amplify the heat shock protein terminator sequence (SEQ ID NO: 19).

Furthermore, using a plasmid vector pUC19 (manufactured by Takara Bio) as a template, and a pair of the primer Nos. 20 and 21 shown in Table 1, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression.

Herein, the expression plasmid consisted of the pUC19 vector sequence and an insert sequence in which the tubulin promoter sequence, the zeocin resistance gene and the heat shock protein terminator sequence were linked in this order.

(2) Obtaining Desaturase Gene, and Construction of Plasmid for Desaturase Gene Expression Total RNA of *Nannochloropsis oculata* strain NIES-2145 was extracted. The cDNA was obtained by reverse transcription using the total RNA, and SuperScript (trademark) III First-Strand Synthesis SuperMix for qRT-PCR (manufactured by invitrogen).

Using the above cDNA as a template, and a pair of the primer Nos. 22 and 23 shown in Table 1, PCR was carried out to obtain a gene (NoΔ9-DES gene) fragment consisting of the nucleotide sequence set forth in SEQ ID NO: 10.

In a similar manner, using the above cDNA as a template, and a pair of the primer Nos. 24 and 25 shown in Table 1, PCR was carried out to obtain a gene (NoΔ12-DES gene) fragment consisting of the nucleotide sequence set forth in SEQ ID NO: 2.

In a similar manner, using the above cDNA as a template, and a pair of the primer Nos. 26 and 27 shown in Table 1, PCR was carried out to obtain a gene (NoΔ6-DES gene) fragment consisting of the nucleotide sequence set forth in SEQ ID NO: 4.

In a similar manner, using the above cDNA as a template, and a pair of the primer Nos. 28 and 29 shown in Table 1, PCR was carried out to obtain a gene (NoΔ5-DES gene) fragment consisting of the nucleotide sequence set forth in SEQ ID NO: 8.

Further, using the above cDNA as a template, and a pair of the primer Nos. 30 and 31 shown in Table 1, PCR was carried out to obtain a gene (Noω3-DES gene) fragment consisting of the nucleotide sequence set forth in SEQ ID NO: 6.

Further, using a genome of *Nannochloropsis oculata* strain NIES-2145 as a template, and a pair of the primer Nos. 32 and 33, and a pair of the primer Nos. 34 and 35 shown in Table 1, PCR were carried out to obtain the LDSP promoter fragment (SEQ ID NO: 36), and the VCP1 terminator fragment (SEQ ID NO: 37).

Furthermore, using the plasmid for zeocin resistance gene expression as a template, and a pair of the primer Nos. 38 and 21 shown in Table 1, PCR was carried out to amplify a fragment containing the cassette for zeocin resistance gene expression (the tubulin promoter sequence, the zeocin resistance gene, and the heat shock protein terminator sequence) and the pUC19 sequence.

The fragments containing each desaturase gene fragment, LDSP promoter fragment, VCP1 terminator fragment, and zeocin resistance gene expression cassette, and pUC19 sequence were fused by a method in a manner similar to described above, to construct a plasmid for NoΔ9-DES gene expression, a plasmid for NoΔ12-DES gene expression, a plasmid for NoΔ6-DES gene expression, a plasmid for NoΔ5-DES gene expression, and a plasmid for Noω3-DES gene expression, respectively.

Herein, the expression plasmid consisted of the pUC19 vector sequence and an insert sequence in which the LDSP promoter sequence, the each desaturase gene, the VCP1 terminator sequence, the tubulin promoter sequence, the zeocin resistance gene and the heat shock protein terminator sequence were linked in this order.

(3) Introduction of a Cassette for Desaturase Gene Expression into *Nannochloropsis oculata*, and Culturing the Transformant Using the above-described plasmid for the each desaturase gene expression prepared as a template respectively, and a pair of the primer Nos. 32 and 18 shown in Table 1, PCR were carried out to amplify the cassette for each desaturase gene expression (a DNA fragment containing the LDSP promoter sequence, the each desaturase gene, the VCP1 terminator sequence, the tubulin promoter sequence, the zeocin resistance gene, and the heat shock protein terminator sequence) respectively.

The amplified each DNA fragment was purified using High Pure PCR Product Purification Kit (manufactured by Roche Applied Science). Herein, sterilized water was used for elution upon purification without using an elution buffer included in the kit.

About $1\times10^9$ cells of *Nannochloropsis oculata* strain NIES-2145 were washed with 384 mM sorbitol solution to completely remove a salt, and the resultant was used as a host cell for transformation. The cassette for each desaturase gene expression as amplified above was mixed by about 500 ng with the host cell respectively, and electroporation was carried out under the conditions of 50 ρF, 500Ω and 2,200 v/2 mm.

After twenty four hours recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant was inoculated in f/2 agar medium containing 2 μg/mL of zeocin, and cultured for two to three weeks under 12 h/12 h light-dark conditions at 25° C. under an atmosphere of 0.3% $CO_2$. Each *Nannochloropsis oculata* strain containing the cassette for each desaturase gene expression (NoΔ9-DES transgenic strain ((delta9 DES) strain), NoΔ12-DES transgenic strain ((delta12 DES) strain), NoΔ6-DES transgenic strain ((delta6 DES) strain), NoΔ5-DES transgenic strain ((delta5 DES) strain), and Noω3-DES transgenic strain ((omega3 DES) strain)) was selected from the resultant colonies by a PCR method (obtaining three independent lines, respectively). The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for two weeks under the 12 h/12 h light-dark conditions at 25° C. under the atmosphere of 0.3% $CO_2$, to prepare preculture fluid. Then, 2 mL of the preculture fluid was inoculated to 18 mL of medium in which a nitrogen concentration in the f/2 medium was reinforced 5 times, and a phosphorus concentration therein was reinforced 5 times (hereinafter, referred to as "N5P5 medium"), and subjected to shaking culture for two weeks under the 12 h/12 h light-dark conditions at 25° C. under the atmosphere of 0.3% $CO_2$. In addition, as a negative control, an experiment was also conducted on the wild type strain, *Nannochloropsis oculata* strain NIES-2145 (WT strain).

(4) Extraction of Lipid from Culture Fluid and Analysis of Fatty Acids Contained Therein To 1 mL of the culture fluid, 50 μL of 1 mg/mL glyceryl triheptadecanoate (manufacture by Sigma-Aldrich) solution in chloroform as an internal standard was added, and then 0.5 mL of chloroform and 1 mL of methanol were further added. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette.

A nitrogen gas was blown onto the resultant chloroform layer to be dried into solid, 0.7 mL of 0.5 N potassium hydroxide solution in methanol was added thereto, and the resultant material was kept warm at 80° C. 30 minutes. Then, 1 mL of 14% boron trifluoride solution (manufactured by Sigma-Aldrich) was added thereto, and the mixture was kept warm at 80° C. for 10 minutes. Thereafter, 0.5 mL of hexane and 1 mL of saturated saline were added thereto, and the mixture was vigorously stirred and then was left for 10 minutes at room temperature. Then, the hexane layer being upper layer was collected to obtain fatty acid methyl esters.

Under the measuring conditions as follows, the obtained fatty acid methyl esters were provided for gas chromatographic analysis.

<Gas Chromatography Conditions>

Analysis apparatus: 7890A (manufactured by Agilent Technologies)

Capillary column: DB-WAX (10 m×100 μm×0.10 μm, manufactured by J&W Scientific)

Mobile phase: high purity helium

Oven temperature: maintained for 0.5 minutes at 100° C.→100 to 250° C. (temperature increase at 20° C./minute)→maintained for 3 minutes at 250° C. (post run: 1 minute)

Injection port temperature: 300° C.

Injection method: split injection (split ratio: 50:1)

Amount of injection: 5 μL

Cleaning vial: methanol

Detection method: FID

Detector temperature: 350° C.

The fatty acid methyl esters were identified by providing the identical sample for gas chromatography-mass spectrometry analysis under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of fatty acid methyl esters having 17 carbon atoms derived from the internal standard, and carried out corrections between the samples, and then the amount of each of the fatty acids per liter of the culture fluid was calculated. Further, the amount of total fatty acids was calculated by summing the amounts of each of the fatty acids thus obtained, and weight proportion of each of the fatty acids in the amount of total fatty acids were calculated. Table 3 shows the results.

Herein, in Table below, "TFA" presents total fatty acid, and "Fatty Acid Composition (% TFA)" presents the proportion of a weight of each fatty acid relative to a weight of the total fatty acid. Further, "n" designates an integer of 3 to 5. "C20:n (% TFA)" presents a total of the proportion of weight of each of C20:3 fatty acids, C20:4 fatty acids and C20:5 fatty acids relative to the weight of the total fatty acids.

TABLE 3

| | TFA (mg/L) | Fatty acid composition (% TFA) | | | | | | | | |
|---|---|---|---|---|---|---|---|---|---|---|
| | | C12:0 | C14:0 | C16:0 | C16:1 (Δ9) | C18:0 | C18:1 (Δ9) | C18:2 (Δ6, 9) | C18:2 (Δ9, 12) | C18:3 (Δ6, 9, 12) |
| WT strain | 1499.5 | 0.3 | 5.5 | 37.5 | 25.4 | 1.0 | 11.3 | 0.2 | 1.4 | 0.4 |
| (comparative example) | 1396.8 | 0.3 | 5.4 | 37.1 | 25.4 | 1.0 | 11.4 | 0.2 | 1.4 | 0.4 |
| | 1293.7 | 0.3 | 5.4 | 36.8 | 25.4 | 1.0 | 11.3 | 0.2 | 1.3 | 0.4 |

TABLE 3-continued

| | | | | | | | | | | |
|---|---|---|---|---|---|---|---|---|---|---|
| (delta9 DES) strain | 1345.9 | 0.3 | 5.2 | 31.1 | 29.2 | 0.6 | 21.4 | 0.2 | 1.0 | 0.2 |
| (comparative example) | 1665.9 | 0.3 | 5.4 | 30.9 | 28.7 | 0.6 | 20.4 | 0.2 | 1.0 | 0.2 |
| | 1507.8 | 0.3 | 5.3 | 29.4 | 29.3 | 0.6 | 21.2 | 0.2 | 1.0 | 0.2 |
| (delta12 DES) strain | 1215.4 | 0.2 | 5.4 | 39.9 | 26.9 | 1.1 | 4.7 | 0.0 | 5.6 | 0.6 |
| (comparative example) | 1296.5 | 0.3 | 5.1 | 39.0 | 27.0 | 1.0 | 4.7 | 0.0 | 5.7 | 0.7 |
| | 1358.3 | 0.2 | 5.1 | 39.8 | 27.2 | 1.1 | 4.7 | 0.0 | 5.3 | 0.6 |
| (delta6 DES) strain | 1427.7 | 0.2 | 5.2 | 38.4 | 26.8 | 1.2 | 10.9 | 1.8 | 0.2 | 0.4 |
| (comparative example) | 1430.0 | 0.2 | 4.9 | 38.0 | 26.7 | 1.1 | 10.8 | 1.9 | 0.2 | 0.5 |
| | 1369.6 | 0.3 | 4.9 | 38.8 | 27.5 | 1.1 | 11.0 | 2.0 | 0.2 | 0.4 |
| (delta5 DES) strain | 1381.0 | 0.6 | 5.2 | 37.9 | 27.6 | 1.2 | 11.1 | 0.1 | 1.2 | 0.3 |
| (comparative example) | 1382.1 | 0.3 | 5.3 | 37.2 | 28.0 | 1.0 | 11.4 | 0.2 | 1.2 | 0.3 |
| | 1402.3 | 0.3 | 5.3 | 36.9 | 28.4 | 1.0 | 11.5 | 0.2 | 1.1 | 0.3 |
| (omega3 DES) strain | 1488.8 | 0.3 | 5.3 | 37.1 | 27.0 | 1.0 | 11.9 | 0.1 | 1.2 | 0.3 |
| (comparative example) | 1358.4 | 0.3 | 5.7 | 37.0 | 26.3 | 1.0 | 11.7 | 0.1 | 1.3 | 0.4 |
| | 1386.3 | 0.3 | 5.7 | 36.5 | 26.3 | 1.0 | 11.6 | 0.1 | 1.3 | 0.4 |

| | | Fatty acid composition (% TFA) | | | | |
|---|---|---|---|---|---|---|
| | TFA (mg/L) | C18:4 (Δ6, 9, 12, 15) | C20:3 (Δ8, 11, 14) | C20:4 (Δ5, 8, 11, 14) | C20:5 (Δ5, 8, 11, 14, 17) | C20:n (% TFA) |
| WT strain | 1499.5 | 0.0 | 0.0 | 3.2 | 13.9 | 17.1 |
| (comparative example) | 1396.8 | 0.0 | 0.0 | 2.9 | 14.7 | 17.6 |
| | 1293.7 | 0.0 | 0.0 | 3.1 | 15.0 | 18.1 |
| (delta9 DES) strain | 1345.9 | 0.0 | 0.0 | 2.2 | 8.6 | 10.8 |
| (comparative example) | 1665.9 | 0.0 | 0.0 | 2.7 | 9.6 | 12.3 |
| | 1507.8 | 0.0 | 0.0 | 2.4 | 10.1 | 12.5 |
| (delta12 DES) strain | 1215.4 | 0.0 | 0.6 | 4.1 | 10.9 | 15.6 |
| (comparative example) | 1296.5 | 0.0 | 0.6 | 4.4 | 11.5 | 16.5 |
| | 1358.3 | 0.0 | 0.7 | 4.3 | 10.9 | 15.9 |
| (delta6 DES) strain | 1427.7 | 0.0 | 0.3 | 3.3 | 11.3 | 14.8 |
| (comparative example) | 1430.0 | 0.0 | 0.2 | 3.4 | 12.0 | 15.7 |
| | 1369.6 | 0.0 | 0.2 | 2.8 | 10.9 | 13.9 |
| (delta5 DES) strain | 1381.0 | 0.0 | 0.0 | 3.3 | 11.5 | 14.8 |
| (comparative example) | 1382.1 | 0.0 | 0.0 | 2.8 | 12.2 | 15.0 |
| | 1402.3 | 0.0 | 0.0 | 2.6 | 12.4 | 15.0 |
| (omega3 DES) strain | 1488.8 | 0.2 | 0.0 | 0.5 | 15.2 | 15.6 |
| (comparative example) | 1358.4 | 0.2 | 0.0 | 0.5 | 15.5 | 16.0 |
| | 1386.3 | 0.2 | 0.0 | 0.5 | 16.1 | 16.6 |

As is apparent from the Table 3, in the transformant into which the NoΔ9-DES gene was introduced ((delta9 DES) strain), the proportion of the amount of C18:1Δ9 was significantly increased in comparison with that in the wild type strain (WT strain). However, the proportion of the amount of C20:5Δ5,8,11,14,17 was reduced. These results suggest that a reaction catalyzed by Δ9-DES is hard to be a rate-limiting step in synthesis of PUFA.

Further, in the transformant into which the NoΔ12-DES gene was introduced ((delta12 DES) strain), the proportion of the amount of C18:1Δ9 was reduced, and the proportion of the amount of C18:2Δ9,12 was significantly increased.

In the transformant into which the NoΔ6-DES gene was introduced ((delta6 DES) strain), the proportion of the amount of C18:2Δ9,12 was slightly reduced, and the proportion of the amount of C18:2Δ6,9 was slightly increased in comparison with that in the wild type strain.

Further, in the transformant into which the NoΔ5-DES gene was introduced ((delta5 DES) strain), no significant change of the fatty acid composition was observed.

Furthermore, in the transformant into which the Noω3-DES gene was introduced ((omega3 DES) strain), the proportion of the amount of C20:4Δ5,8,11,14 was reduced, and the proportion of the amount of C20:5Δ5,8,11,14,17 was slightly increased, in comparison with that in the wild type strain. From these results, it was suggested that, in the synthesis of PUFA of the genus *Nannochloropsis*, the pathway is not through C20:4Δ8,11,14,17, but through C20:4Δ5,8,11,14.

Thus, it became apparent that the fatty acid composition is changed by enhancing expression of the each desaturase gene. Then, a main synthetic pathway of EPA in the algae belonging to the genus *Nannochloropsis* was identified as a pathway through C20:4Δ5,8,11,14 as shown in FIG. 1.

However, amount of PUFA such as C20:3, C20:4 and C20:5 was unable to be highly increased only by enhancing expression of only one kind of desaturase gene.

Example 2 Transformation of *Nannochloropsis oculata* Using Two Kinds of Desaturase Genes Derived from *Nannochloropsis oculata*, and Production of Lipids by the Transformant (1) Construction of Plasmid for Desaturase Gene Expression (Paromomycin Resistance)

Using the each plasmid for NoΔ6-DES gene expression, plasmid for NoΔ5-DES gene expression, and plasmid for Noω3-DES gene expression constructed in Example 1 as a template respectively, and a pair of the primer Nos. 16 and 17 shown in Table 1, PCR were carried out to prepare each desaturase gene fragment (containing the vector sequence and the like).

Further, paromomycin resistance gene was amplified by carrying out PCR by using the paromomycin resistance gene (SEQ ID NO: 39) artificially synthesized as a template, and a pair of the primer Nos. 40 and 41 shown in Table 2.

The each desaturase gene fragment (containing the vector sequence and the like) and the paromomycin resistance gene fragment were fused by a method in a manner similar to that in Example 1, and a plasmid for NoΔ6-DES gene expression (paromomycin resistance), a plasmid for NoΔ5-DES gene expression (paromomycin resistance), and a plasmid for Noω3-DES gene expression (paromomycin resistance) were constructed respectively.

Herein, the expression plasmid consisted of the pUC19 vector sequence and an insert sequence in which the LDSP promoter sequence, each desaturase gene, the VCP1 terminator sequence, the tubulin promoter sequence, the paromomycin resistance gene and the heat shock protein terminator sequence were linked in this order.

Using the prepared plasmid for the each desaturase gene expression (paromomycin resistance) as a template, and a pair of the primer Nos. 32 and 18 shown in Table 1, PCR was carried out to amplify the cassette for each desaturase gene expression (a DNA fragment containing the LDSP promoter sequence, the each desaturase gene, the VCP1 terminator sequence, the tubulin promoter sequence, the paromomycin resistance gene, and the heat shock protein terminator sequence).

The amplified DNA fragments obtained were purified according to the same method as in Example 1, and the purified fragments were introduced into the NoΔ12-DES transgenic strain prepared in Example 1 by electroporation. Recovery cultivation was carried out according to the same method as in Example 1, and then the resultant was applied onto an f/2 agar medium containing 2 μg/mL of zeocin and 100 μg/mL of paromomycin, and cultured for two to three weeks under 12 h/12 h light-dark conditions at 25° C. under an atmosphere of 0.3% $CO_2$. *Nannochloropsis oculata* strains containing each cassette for desaturase gene expression (NoΔ12-DES and NoΔ6-DES transgenic strain ((delta12 DES+delta6 DES) strain), NoΔ12-DES and NoΔ5-DES transgenic strain ((delta12 DES+delta5 DES) strain), or NoΔ12-DES and Noω3-DES transgenic strain ((delta12 DES+omega3 DES) strain)) were selected by PCR from obtained colonies.

(2) Culture of Transformant, Extraction of Lipids and Analysis of Fatty Acids Contained Therein The selected strains (obtaining three independent lines, respectively) were inoculated to 20 mL of the N15P5 media, and subjected to shaking culture for three to four weeks under the 12 h/12 h light-dark conditions at 25° C. under the atmosphere of 0.3% $CO_2$, to prepare preculture fluid. Then, 2 mL of the preculture fluids were inoculated to 18 mL of the N5P5 media, and subjected to shaking culture for two weeks under the 12 h/12 h light-dark conditions at 25° C. under the atmosphere of 0.3% $CO_2$. In addition, as negative controls, the wild type strain and the NoΔ12-DES transgenic strain were also subjected to the same experiment.

Extraction of lipids from obtained culture liquids and analysis of fatty acids contained therein were carried out, according to the same method as in Example 1. Table 4 shows the results.

TABLE 4

| | TFA (mg/L) | Fatty acid composition (% TFA) C12:0 | C14:0 | C16:0 | C16:1 (Δ9) | C18:0 | C18:1 (Δ9) | C18:2 (Δ6, 9) | C18:2 (Δ9, 12) | C18:3 (Δ6, 9, 12) |
|---|---|---|---|---|---|---|---|---|---|---|
| WT strain | 1450.9 | 0.3 | 6.2 | 40.0 | 28.3 | 1.3 | 11.9 | 0.0 | 1.1 | 0.4 |
| (comparative example) | 1664.5 | 0.3 | 6.2 | 39.7 | 28.1 | 1.3 | 12.1 | 0.0 | 1.2 | 0.4 |
| | 1764.4 | 0.3 | 6.3 | 40.0 | 28.3 | 1.2 | 11.2 | 0.0 | 1.1 | 0.4 |
| (delta12 DES) strain | 1536.9 | 0.3 | 6.2 | 42.0 | 27.0 | 1.2 | 4.6 | 0.0 | 4.7 | 0.6 |
| (comparative example) | 1733.9 | 0.3 | 6.3 | 41.8 | 27.2 | 1.2 | 4.7 | 0.0 | 4.5 | 0.6 |
| | 1887.5 | 0.3 | 6.2 | 42.1 | 27.8 | 1.2 | 4.9 | 0.0 | 4.5 | 0.6 |
| (delta12 DES + | 1563.5 | 0.2 | 5.6 | 42.2 | 26.3 | 1.0 | 3.2 | 0.0 | 0.6 | 1.3 |
| delta6 DES) strain | 1678.4 | 0.2 | 6.1 | 43.5 | 25.4 | 1.2 | 3.3 | 0.0 | 0.5 | 1.3 |
| (present invention) | 1744.8 | 0.2 | 6.2 | 43.9 | 25.5 | 1.2 | 3.3 | 0.0 | 0.4 | 1.3 |
| (delta12 DES + | 1717.6 | 0.3 | 6.1 | 42.4 | 26.6 | 1.1 | 4.7 | 0.0 | 4.4 | 0.7 |
| delta5 DES) strain | 1814.2 | 0.2 | 6.3 | 43.0 | 26.9 | 1.1 | 4.9 | 0.0 | 4.3 | 0.7 |
| (comparative example) | 1907.4 | 0.3 | 6.2 | 43.0 | 27.4 | 1.1 | 5.0 | 0.0 | 4.2 | 0.7 |
| (delta12 DES + | 1567.4 | 0.3 | 7.1 | 42.2 | 22.6 | 1.2 | 7.3 | 0.0 | 5.0 | 0.5 |
| omega3 DES) strain | 1730.5 | 0.4 | 7.5 | 41.3 | 22.3 | 1.1 | 7.2 | 0.0 | 5.1 | 0.5 |
| (comparative example) | 1641.1 | 0.4 | 7.4 | 40.9 | 22.0 | 1.1 | 7.2 | 0.0 | 5.3 | 0.5 |

| | TFA (mg/L) | Fatty acid composition (% TFA) C18:4 (Δ6, 9, 12, 15) | C20:3 (Δ8, 11, 14) | C20:4 (Δ5, 8, 11, 14) | C20:5 (Δ5, 8, 11, 14, 17) | C20:n (% TFA) |
|---|---|---|---|---|---|---|
| WT strain | 1450.9 | 0.0 | 0.0 | 2.4 | 8.0 | 10.5 |
| (comparative example) | 1664.5 | 0.0 | 0.0 | 2.5 | 8.2 | 10.7 |
| | 1764.4 | 0.0 | 0.0 | 2.4 | 8.7 | 11.1 |
| (delta12 DES) strain | 1536.9 | 0.0 | 0.6 | 4.1 | 8.7 | 13.4 |
| (comparative example) | 1733.9 | 0.0 | 0.7 | 4.2 | 8.6 | 13.4 |
| | 1887.5 | 0.0 | 0.7 | 3.8 | 7.9 | 12.4 |
| (delta12 DES + | 1563.5 | 0.0 | 2.5 | 7.9 | 9.0 | 19.4 |
| delta6 DES) strain | 1678.4 | 0.0 | 2.6 | 7.3 | 8.4 | 18.4 |
| (present invention) | 1744.8 | 0.0 | 2.6 | 7.3 | 8.0 | 17.9 |
| (delta12 DES + | 1717.6 | 0.0 | 0.5 | 4.6 | 8.5 | 13.6 |
| delta5 DES) strain | 1814.2 | 0.0 | 0.5 | 4.2 | 7.8 | 12.6 |
| (comparative example) | 1907.4 | 0.0 | 0.5 | 4.0 | 7.7 | 12.2 |
| (delta12 DES + | 1567.4 | 0.4 | 0.0 | 0.6 | 12.7 | 13.3 |
| omega3 DES) strain | 1730.5 | 0.4 | 0.0 | 0.6 | 13.5 | 14.1 |
| (comparative example) | 1641.1 | 0.5 | 0.0 | 0.5 | 14.1 | 14.6 |

As shown in Example 1, even if a transcription amount of each of the NoΔ6-DES gene or the NoΔ12-DES gene was enhanced alone, an increase in the amount of PUFA was unable to be confirmed.

On the other hand, as is apparent from the Table 4, in the transformant into which the NoΔ12-DES gene and the No8,6-DES gene were introduced ((delta12 DES+delta6

DES) strain), the proportion of the amount of 018:1Δ9 was greatly reduced, and a proportion of the amount of C20:n was largely increased, in comparison with that in the wild type strain or (delta12 DES) strain. In particular, the proportion of the amount of C20:4Δ5,8,11,14 (arachidonic acid) was largely increased.

Moreover, as shown in Table 4, in the (delta12 DES+delta6 DES) strain, accumulation of C18:3Δ6,9,12 was hardly able to be detected. This result indicates that, in the synthetic pathway of PUFA, particularly, C20:4Δ5,8,11,14 and C20:5Δ5,8,11,14,17 in the algae belonging to the genus *Nannochloropsis*, a series of consecutive steps in which a reaction is catalyzed by the Δ12-DES and the Δ6-DES (the reaction in which C18:2,8,9,12 is formed from C18:1Δ9 and C18:3Δ6,9,12 is formed from C18:2Δ9,12 formed) are in the rate-limiting step.

Further, in the transformant into which the NoΔ12-DES gene and Noω3-DES gene were introduced ((delta12 DES+omega3 DES) strain), the proportion of the amount of C20:4Δ5,8,11,14 was reduced, and the proportion of the amount of C20:5Δ5,8,11,14,17 was increased, in comparison with that in (delta12 DES) strain. However, the proportion of the amount of C20:n was nearly unchanged Further, in the transformant into which the NoΔ12-DES gene and the NoΔ5-DES gene were introduced ((delta12 DES+delta5 DES) strain), the proportions of the amount of C20:4Δ5,8,11,14, the amount of C20:5Δ5,8,11,14,17, and the amount of C20:n were nearly unchanged in comparison with that in (delta12 DES) strain.

From these results also, it is found that it is important to enhance expressions of the Δ12-DES and the Δ6-DES to reinforce a sequential reaction catalyzed by the Δ12-DES and the Δ6-DES in order to improve the productivity of PUFA in the genus *Nannochloropsis.*

Example 3 Transformation of *Nannochloropsis oculata* Using Three Kinds of Desaturase Genes Derived from *Nannochloropsis oculata*, and Production of Lipids by the Transformant (1) Construction of Plasmid for Desaturase Gene Expression (Hygromycin Resistance)

Using the plasmid for Noω3-DES gene expression constructed in Example 1 as a template, and a pair of the primer Nos. 16 and 17 shown in Table 1, PCR was carried out to prepare the Noω3-DES gene fragment (containing the vector sequence and the like).

Further, hygromycin resistance gene was amplified by carrying out PCR by using the hygromycin resistance gene (SEQ ID NO: 42) artificially synthesized as a template, and a pair of the primer Nos. 43 and 44 shown in Table 2.

These two fragments were fused by a method in a manner similar to that in Example 1, and a plasmid for Noω3-DES gene expression (hygromycin resistance) was constructed.

Herein, the expression plasmid consisted of the pUC19 vector sequence and an insert sequence in which the LDSP promoter sequence, the Noω3-DES gene, the VCP1 terminator sequence, the tubulin promoter sequence, the hygromycin resistance gene and the heat shock protein terminator sequence were linked in this order.

Using the prepared plasmid for the Noω3-DES gene expression (hygromycin resistance) as a template, and a pair of the primer Nos. 32 and 18 shown in Table 1, PCR was carried out to amplify the cassette for Noω3-DES gene expression (a DNA fragment containing the LDSP promoter sequence, the Noω3-DES gene, the VCP1 terminator sequence, the tubulin promoter sequence, the hygromycin resistance gene, and the heat shock protein terminator sequence).

The amplified fragment was purified according to the same method as in Example 1, and the purified fragment was introduced into the NoΔ12-DES and NoΔ6-DES transgenic strain prepared in Example 2, by electroporation. Recovery cultivation was carried out according to the same method as in Example 1, and then the resultant was applied onto an f/2 agar medium containing 500 μg/mL of hygromycin, and cultured for two to three weeks under 12 h/12 h light-dark conditions at 25° C. under an atmosphere of 0.3% $CO_2$. *Nannochloropsis oculata* strain containing the cassette for Noω3-DES gene expression (NoΔ12-DES, NoΔ6-DES and Noω3-DES transgenic strain ((delta12 DES+delta6 DES+omega3 DES) strain)) was selected by PCR from obtained colonies.

(2) Culture of Transformant, Extraction of Lipids and Analysis of Fatty Acids Contained Therein The selected strain was inoculated to 20 mL of the N15P5 medium, and subjected to shaking culture for three to four weeks under the 12 h/12 h light-dark conditions at 25° C. under the atmosphere of 0.3% $CO_2$, to prepare preculture fluid. Then, 2 mL of the preculture fluid was inoculated to 18 mL of the N5P5 medium, and subjected to shaking culture for three weeks under the 12 h/12 h light-dark conditions at 25° C. under the atmosphere of 0.3% $CO_2$. In addition, as negative controls, the wild type strain, the NoΔ12-DES transgenic strain, the Δ12-DES and NoΔ6-DES transgenic strain, and the NoΔ12-DES and Noω3-DES transgenic strain were also subjected to the same experiment.

Extraction of lipids from obtained culture liquids and analysis of fatty acids contained therein were carried out, according to the same method as in Example 1. The results of production amount of total fatty acids and the fatty acid composition in the third week are shown in Table 5. The amount of total fatty acids, production amount of C20:5 fatty acid and production amount of C20:n fatty acids in the first week, the second week and the third week of culture are shown in Table 6. Then, the proportion of the amount of C20:5 fatty acid and the proportion of the amount of C20:n fatty acids in the first week, the second week and the third week of culture are shown in Table 7.

TABLE 5

| | | Fatty acid composition (% TFA) | | | | | | | | |
|---|---|---|---|---|---|---|---|---|---|---|
| | TFA (mg/L) | C12:0 | C14:0 | C16:0 | C16:1 (Δ9) | C18:0 | C18:1 (Δ9) | C18:2 (Δ6, 9) | C18:2 (Δ9, 12) | C18:3 (Δ6, 9, 12) |
| WT strain (comparative example) | 1309.2 | 0.0 | 4.8 | 38.0 | 31.4 | 1.4 | 14.6 | 0.2 | 0.9 | 0.2 |
| (delta12 DES) strain (comparative example) | 1566.5 | 0.0 | 5.5 | 42.7 | 29.1 | 1.7 | 6.7 | 0.0 | 4.6 | 0.5 |

TABLE 5-continued

| | | | | | | | | | | |
|---|---|---|---|---|---|---|---|---|---|---|
| (delta12 DES + omega3 DES) strain (comparative example) | 1586.4 | 0.0 | 6.0 | 43.0 | 23.1 | 1.6 | 11.0 | 0.0 | 5.3 | 0.6 |
| (delta12 DES + delta6 DES) strain (present invention) | 1764.0 | 0.0 | 5.4 | 45.5 | 27.8 | 1.7 | 4.3 | 0.0 | 0.4 | 1.1 |
| (delta12 DES + delta6 DES + omega3 DES) strain (present invention) | 1526.5 | 0.0 | 5.1 | 40.1 | 28.2 | 1.4 | 7.7 | 0.0 | 0.6 | 1.6 |

| | | Fatty acid composition (% TFA) | | | | |
|---|---|---|---|---|---|---|
| | TFA (mg/L) | C18:4 (Δ6, 9, 12, 15) | C20:3 (Δ8, 11, 14) | C20:4 (Δ5, 8, 11, 14) | C20:5 (Δ5, 8, 11, 14, 17) | C20:n (% TFA) |
| WT strain (comparative example) | 1309.2 | 0.0 | 0.0 | 1.6 | 6.9 | 8.5 |
| (delta12 DES) strain (comparative example) | 1566.5 | 0.0 | 0.7 | 3.3 | 5.2 | 9.2 |
| (delta12 DES + omega3 DES) strain (comparative example) | 1586.4 | 0.4 | 0.0 | 0.3 | 8.6 | 9.0 |
| (delta12 DES + delta6 DES) strain (present invention) | 1764.0 | 0.0 | 2.9 | 6.3 | 4.6 | 13.8 |
| (delta12 DES + delta6 DES + omega3 DES) strain (present invention) | 1526.5 | 0.0 | 1.5 | 0.8 | 12.9 | 15.3 |

TABLE 6

| | Type of fatty acid | Yield (mg/L) 1 w | 2 w | 3 w |
|---|---|---|---|---|
| WT strain (comparative example) | TFA | 272.2 | 855.2 | 1309.2 |
| | C20:5 | 46.9 | 70.6 | 90.0 |
| | C20:n | 55.3 | 85.0 | 110.7 |
| (delta12 DES) strain (comparative example) | TFA | 323.9 | 941.3 | 1566.5 |
| | C20:5 | 45.2 | 63.7 | 81.7 |
| | C20:n | 60.7 | 103.8 | 144.6 |
| (delta12 DES + omega3 DES) strain (comparative example) | TFA | 311.5 | 909.2 | 1586.4 |
| | C20:5 | 62.0 | 100.0 | 136.7 |
| | C20:n | 62.0 | 104.2 | 142.2 |
| (delta12 DES + delta6 DES) strain (present invention) | TFA | 486.3 | 1069.7 | 1764.0 |
| | C20:5 | 55.8 | 64.3 | 80.8 |
| | C20:n | 104.3 | 162.7 | 242.7 |
| (delta12 DES + delta6 DES + omega3 DES) strain (present invention) | TFA | 314.1 | 907.4 | 1504.2 |
| | C20:5 | 83.4 | 135.4 | 193.7 |
| | C20:n | 91.8 | 166.1 | 246.8 |

TABLE 7

| | Type of fatty acid | Proportion (% TFA) 1 w | 2 w | 3 w |
|---|---|---|---|---|
| WT strain (comparative example) | C20:5 | 17.2 | 8.3 | 6.9 |
| | C20:n | 20.3 | 9.9 | 8.5 |
| (delta12 DES) strain (comparative example) | C20:5 | 14.0 | 6.8 | 5.2 |
| | C20:n | 18.8 | 11.0 | 9.2 |
| (delta12 DES + omega3 DES) strain (comparative example) | C20:5 | 19.9 | 11.0 | 8.6 |
| | C20:n | 19.9 | 11.5 | 9.0 |
| (delta12 DES + delta6 DES) strain (present invention) | C20:5 | 11.5 | 6.0 | 4.6 |
| | C20:n | 21.5 | 15.2 | 13.8 |
| (delta12 DES + delta6 DES + omega3 DES) strain (present invention) | C20:5 | 26.6 | 14.9 | 12.9 |
| | C20:n | 29.2 | 18.3 | 16.4 |

As is apparent from the Table 5, in the transformant into which the NoΔ12-DES gene, the NoΔ6-DES gene and the Noω3-DES gene were introduced ((delta12 DES+delta6 DES+omega3 DES) strain), the proportion of the amount of C20:4Δ5,8,11,14 was greatly reduced, and the proportion of the amount of C20:5Δ5,8,11,14,17 was largely increased, in comparison with that in the (delta12 DES+delta6 DES) strain. Further, the proportion of the amount of C20:n was also increased. From these results, it was found that the productivity of PUFA, particularly, C20:5Δ5,8,11,14,17 is further improved by enhancing expression of the ω3-DES in addition to the Δ12-DES and the Δ6-DES.

Further, as is apparent from Table 6 and Table 7, in the wild type strain (WT strain), accordingly as a culture period becomes longer, the proportion of the amount of C20:n or C20:5 is reduced.

In contrast, in the (delta12 DES+delta6 DES) strain, the production amount of C20:n and the proportion of the amount of C20:n in the amount of whole fatty acids were increased in any culture period in comparison with that in the wild type strain (WT strain) and the (delta12 DES) strain.

Further, in the (delta12 DES+delta6 DES+omega3 DES) strain, the production amount of C20:n (particularly, C20:5Δ5,8,11,14,17), and the proportion of the amount of C20:n (particularly, C20:5Δ5,8,11,14,17) in the amount of whole fatty acids were further increased in comparison with that in the (delta12 DES+delta6 DES) strain.

Further, in the (delta12 DES+delta6 DES) strain or the (delta12 DES+delta6 DES+omega3 DES) strain, a reduction rate of the proportion of the amount of C20:n in association with prolongation of the culture period is suppressed in comparison with that in the wild stain (WT strain) or the like.

Example 4 Transformation of (Delta12 DES+Delta6 DES+Omega3 DES) Strain Using Δ9-DES Gene, Δ5-DES Gene and Δ6-ELO Gene, and Production of Lipids by the Transformant (1) Construction of Plasmid for Desaturase Gene or Elongase Gene Expression (Bialaphos Resistance)

Using the plasmid for NoΔ9-DES gene expression or the plasmid for NoΔ5-DES gene expression constructed in Example 1 as a template, and a pair of the primer Nos. 16 and 17 shown in Table 1, PCR were carried out to amplify the NoΔ9-DES gene fragment and the NoΔ5-DES gene fragment (containing the pUC19 vector sequence itself and the like), respectively.

Further, bialaphos resistance gene (SEQ ID NO: 68) was artificially synthesized. Using the synthesized DNA fragment as a template, and a pair of the primer Nos. 69 and 70 shown in Table 2, PCR was carried out to amplify the bialaphos resistance gene.

Each of NoΔ9-DES gene fragment and NoΔ5-DES gene fragment, and bialaphos resistance gene fragment were fused by a method in a manner similar to that in Example 1, and a plasmid for NoΔ9-DES gene expression (bialaphos resistance) and a plasmid for NoΔ5-DES gene expression (bialaphos resistance) were constructed, respectively.

Herein, the expression plasmid consisted of the pUC19 vector sequence and an insert sequence in which the LDSP promoter sequence, NoΔ9-DES gene or NoΔ5-DES gene, the VCP1 terminator sequence, the tubulin promoter sequence, the bialaphos resistance gene and the heat shock protein terminator sequence were linked in this order.

Using the cDNA of *Nannochloropsis oculata* strain NIES-2145 prepared in Example 1 as a template, and a pair of the primer Nos. 71 and 72 shown in Table 2, PCR was carried out to prepare the gene (NoΔ6-ELO gene) fragment consisting of the nucleotide sequence set forth in SEQ ID NO: 73.

The amplified fragment and the fragment containing LDSP promoter fragment, VCP1 terminator fragment, the cassette for zeocin resistance gene expression, and pUC19 sequence, were fused by a method in a manner similar to that in Example 1, and a plasmid for NoΔ6-ELO gene expression was constructed.

Using the plasmid for NoΔ6-ELO gene expression as a template, and a pair of the primer Nos. 16 and 17 shown in Table 1, PCR was carried out to amplify the NoΔ6-ELO gene fragment (containing pUC19 vector sequence itself and the like). A plasmid for NoΔ6-ELO gene expression (bialaphos resistance) was constructed by fusing the amplified fragment with the bialaphos resistance gene fragment, according to the same method as in Example 1

Herein, the expression plasmid consisted of the pUC19 vector sequence and an insert sequence in which the LDSP promoter sequence, the NoΔ6-ELO gene, the VCP1 terminator sequence, the tubulin promoter sequence, the bialaphos resistance gene and the heat shock protein terminator sequence were linked in this order.

Using the plasmid for NoΔ9-DES gene expression (bialaphos resistance), the plasmid for NoΔ5-DES gene expression (bialaphos resistance), or the plasmid for NoΔ6-ELO gene expression (bialaphos resistance) prepared as a template, and a pair of the primer Nos. 32 and 18 shown in Table 1, PCR was carried out, to amplify cassette for NoΔ9-DES gene expression, cassette for NoΔ5-DES gene expression, or cassette for NoΔ6-ELO gene expression (DNA fragment consisting of the LDSP promoter sequence, the desaturase gene or the elongase gene (NoΔ9-DES gene, NoΔ5-DES gene or NoΔ6-ELO gene), the VCP1 terminator sequence, the tubulin promoter sequence, the bialaphos resistance gene, and the heat shock protein terminator sequence).

The amplified fragments obtained were purified according to the same method as in Example 1, and the purified fragments were introduced respectively into the NoΔ12-DES transgenic, the NoΔ6-DES transgenic, and the Noω3-DES transgenic strain prepared in Example 3, by electroporation. Recovery cultivation was carried out according to the same method as in Example 1, and then the resultant was applied onto an f/2 agar medium containing 750 μg/mL of bialaphos, and cultured for two to three weeks under 12 h/12 h light-dark conditions at 25° C. under an atmosphere of 0.3% $CO_2$. *Nannochloropsis oculata* strain containing the cassette for NoΔ9-DES gene expression ((delta12 DES+delta6 DES+omega3 DES+delta9 DES) strain), *Nannochloropsis oculata* strain containing the cassette for NoΔ5-DES gene expression ((delta12 DES+delta6 DES+omega3 DES+delta5 DES) strain), and *Nannochloropsis oculata* strain containing the cassette for NoΔ6-ELO gene expression ((delta12 DES+delta6 DES+omega3 DES+delta6 ELO) straom) were selected by PCR from obtained colonies, respectively.

(2) Culture of Transformant, Extraction of Lipids and Analysis of Fatty Acids Contained Therein The selected strains were inoculated to 4 mL of the N15P5 media (Microplate for Tissue Culture, manufactured by IWAKI), and subjected to shaking culture for three to four weeks under the 12 h/12 h light-dark conditions at 25° C. under the atmosphere of 0.3% $CO_2$, to prepare preculture fluid. Then, 0.4 mL of the preculture fluids were inoculated to 4 mL of the N5P5 media (Microplate for Tissue Culture, manufactured by IWAKI), and subjected to shaking culture for three weeks under the 12 h/12 h light-dark conditions at 25° C. under the atmosphere of 0.3% $CO_2$. In addition, as negative controls, the wild type strain, and the NoΔ12-DES transgenic, the NoΔ6-DES transgenic and the Noω3-DES transgenic strain were also subjected to the same experiment.

Extraction of lipids from obtained culture liquids and analysis of fatty acids contained therein were carried out, according to the same method as in Example 1. The results of a production amount of total fatty acids and the fatty acid composition in the third week are shown in Table 8.

TABLE 8

| | | Fatty acid composition (% TFA) | | | | | | | | |
|---|---|---|---|---|---|---|---|---|---|---|
| | TFA (mg/L) | C12:0 | C14:0 | C16:0 | C16:1 (Δ9) | C18:0 | C18:1 (Δ9) | C18:1 (Δ11) | C18:2 (Δ6, 9) | C18:2 (Δ9, 12) |
| WT strain (comparative example) | 1755.0 | 0.0 | 5.2 | 38.0 | 30.9 | 1.2 | 14.4 | 0.0 | 0.2 | 0.9 |
| (delta12 DES + delta6 DES + omega3 DES) strain (present invention) | 1652.4 | 0.0 | 4.7 | 34.7 | 29.1 | 0.9 | 7.9 | 0.0 | 0.0 | 1.1 |

TABLE 8-continued

| | | | | | | | | | | |
|---|---|---|---|---|---|---|---|---|---|---|
| (delta12 DES + delta6 DES + omega3 DES + delta9 DES) strain (present invention) | 2026.1 | 0.0 | 3.9 | 27.8 | 28.9 | 0.5 | 12.8 | 0.0 | 0.1 | 1.7 |
| (delta12 DES + delta6 DES + omega3 DES + delta5 DES) strain (present invention) | 1610.2 | 0.0 | 4.8 | 32.7 | 28.3 | 0.9 | 7.0 | 0.0 | 0.0 | 1.1 |
| (delta12 DES + delta6 DES + omega3 DES + delta6 ELO) strain (present invention) | 1816.0 | 0.0 | 5.0 | 36.5 | 29.4 | 0.9 | 5.1 | 0.0 | 0.2 | 0.8 |

| | | Fatty acid composition (% TFA) | | | | | |
|---|---|---|---|---|---|---|---|
| | TFA (mg/L) | C18:3 (Δ6, 9, 12) | C18:4 (Δ6, 9, 12, 15) | C20:3 (Δ8, 11, 14) | C20:4 (Δ5, 8, 11, 14) | C20:5 (Δ5, 8, 11, 14, 17) | C20:n (% TFA) |
| WT strain (comparative example) | 1755.0 | 0.3 | 0.0 | 0.1 | 1.5 | 7.3 | 8.9 |
| (delta12 DES + delta6 DES + omega3 DES) strain (present invention) | 1652.4 | 2.0 | 0.0 | 1.3 | 1.4 | 16.9 | 19.6 |
| (delta12 DES + delta6 DES + omega3 DES + delta9 DES) strain (present invention) | 2026.1 | 1.9 | 0.0 | 1.8 | 1.6 | 18.9 | 22.3 |
| (delta12 DES + delta6 DES + omega3 DES + delta5 DES) strain (present invention) | 1610.2 | 2.1 | 0.0 | 0.7 | 2.0 | 20.4 | 23.1 |
| (delta12 DES + delta6 DES + omega3 DES + delta6 ELO) strain (present invention) | 1816.0 | 0.2 | 0.0 | 2.3 | 1.2 | 18.3 | 21.8 |

As is apparent from the Table 8, in the strain into which the NoΔ12-DES gene, the NoΔ6-DES gene, the Noω3-DES gene and the Nan-DES gene were introduced ((delta12 DES+delta6 DES+omega3 DES+delta9 DES) strain), the proportion of C16:0 was reduced, and the proportions of C18:1Δ9 and C20:n were increased, in comparison with that in the (delta12 DES+delta6 DES+omega3 DES) strain.

In addition, in the strain into which the NoΔ12-DES gene, the NoΔ6-DES, the Noω3-DES gene, and the NoΔ5-DES gene were introduced ((delta12 DES+delta6 DES+omega3 DES+delta5 DES) strain), the proportion of C20:3Δ8,11,14 was reduced, and the proportions of C20:4Δ5,8,11,14 and C20:5Δ5,8,11,14,17 were increased, in comparison with that in the (delta12 DES+delta6 DES+omega3 DES) strain.

Further, in the strain into which the NoΔ12-DES gene, the NoΔ6-DES gene, the Noω3-DES gene, and the NoΔ6-ELO gene were introduced ((delta12 DES+delta6 DES+omega3 DES+delta6 ELO) strain), the proportion of C18:3Δ6,9,12 was reduced, and the proportions of C20:3Δ8,11,14 and C20:n were improved, in comparison with that in the (delta12 DES+delta6 DES+omega3 DES) strain.

From these results, it was found that the productivity of PUFA, particularly, C20:5Δ5,8,11,14,17 is further improved by enhancing the expression of any one of the Δ9-DES, the Δ5-DES and the Δ6-ELO, in addition to the Δ12-DES, the Δ6-DES and the ω3-DES.

Example 5 Analysis of Fatty Acid Composition Contained in TAG in (Delta12 DES+Delta6 DES+Omega3 DES) Strain and (Delta12 DES+Delta6 DES+Omega3 DES+Delta6 ELO) Strain (1) Culture of Wild Type Strain and Transformant The (delta12 DES+delta6 DES+omega3 DES) strain, (delta12 DES+delta6 DES+omega3 DES+delta6 ELO) strain, and wild type strain as a negative control obtained in Example 3 and 4 were inoculated to 20 mL of the N5P5 media, and subjected to shaking culture for five days under the 12 h/12 h light-dark conditions at 25° C. under the atmosphere of 0.3% $CO_2$, to prepare preculture fluid 1. Then, 2 mL of the preculture fluids were inoculated to 18 mL of the N5P5 media, and subjected to shaking culture for five days, to prepare preculture fluid 2. Then, 2 mL of the preculture fluids 2 were inoculated to 18 mL of the N5P5 media, and subjected to shaking culture for three weeks under the same condition.

(2) Extraction of Lipid, Fractionation of TAG, and Analysis of Fatty Acids Contained in TAG To 0.25 mL of the culture fluid, 0.5 mL of chloroform and 1 mL of methanol were added. The mixture was vigorously stirred and then was left for 10 minutes or more. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette. A nitrogen gas was blown onto the resultant chloroform layer to be dried into solid, and the resultant material was dissolved into 20 μL of chloroform.

A total amount of the thus obtained lipids extract, and 3 μL of standard solutions {10 mg/mL of trimyristin (manufactured by Wako Pure Chemical Industries, Ltd.) in chloroform solution} each were spotted onto TLC silica gel 60$F_{254}$ (manufactured by Merck). The resultant material was developed for about 15 minutes by using TLC developing tank DT-150 (manufactured by Mitsubishi Chemical Medience Corporation) with a developing solvent (hexane:diethyl ether:formic acid=42:28:0.3 (volume ratio)). After development, the plate was dried, 0.1% primulin (manufactured by Wako Pure Chemical Industries, Ltd.) dissolved in methanol was sprayed thereon and dried, and then a TAG fraction was detected by handy type UV lamp UVL-21 (manufactured by SOGO LABORATORY GLASS WORKS CO., LTD.).

The TAG fraction was scratched and collected by using a toothpick and 0.1 mL of chloroform, and 0.5 mL of 14% boron trifluoride-methanol solution (manufactured by Sigma-Aldrich) were added thereto, and the temperature of the resultant material was kept constant at 80° C. for 30 minutes. Then, 0.5 mL of hexane and 1 mL of saturated saline were added thereto, and the resultant mixture was vigorously stirred and left to stand for 10 minutes at room temperature, and then, the hexane layer being an upper layer was collected to obtain fatty acid methyl esters.

The obtained fatty acid methyl esters were provided for gas chromatographic analysis according to the same method as in Example 1, and analysis of fatty acids contained therein was carried out thereon. Table 9 shows the results. In addition, in Table 9, "TAG-FA" presents total weight of fatty acid residues constituting TAG, and "fatty acid composition (% TAG-FA)" presents a proportion of weight of each fatty acid residue to the total weight of the fatty acid residues constituting TAG (composition ratio of the fatty acid residues constituting TAG).

TABLE 9

| | Fatty acid composition (% TAG-FA) | | | | | | | | | |
|---|---|---|---|---|---|---|---|---|---|---|
| | C12:0 | C14:0 | C16:0 | C16:1 (Δ9) | C18:0 | C18:1 (Δ9) | C18:1 (Δ11) | C18:2 (Δ6, 9) | C18:2 (Δ9, 12) | C18:3 (Δ6, 9, 12) |
| WT strain (comparative example) | 0.0 | 4.4 | 43.1 | 28.5 | 2.6 | 15.6 | 0.0 | 0.2 | 1.0 | 0.4 |
| (delta12 DES + delta6 DES + omega3 DES) strain (present invention) | 0.0 | 5.3 | 42.6 | 28.8 | 1.6 | 7.5 | 0.4 | 0.0 | 0.6 | 1.6 |
| (delta12 DES + delta6 DES + omega3 DES + delta6 ELO) strain (present invention) | 0.0 | 5.4 | 45.1 | 29.8 | 1.3 | 5.2 | 0.4 | 0.0 | 0.4 | 0.0 |

| | Fatty acid composition (% TAG-FA) | | | | C20:n |
|---|---|---|---|---|---|
| | C18:4 (Δ6, 9, 12, 15) | C20:3 (Δ8, 11, 14) | C20:4 (Δ5, 8, 11, 14) | C20:5 (Δ5, 8, 11, 14, 17) | (% TAG-FA) |
| WT strain (comparative example) | 0.0 | 0.0 | 1.0 | 3.2 | 4.3 |
| (delta12 DES + delta6 DES + omega3 DES) strain (present invention) | 0.0 | 1.4 | 0.7 | 9.4 | 11.5 |
| (delta12 DES + delta6 DES + omega3 DES + delta6 ELO) strain (present invention) | 0.0 | 2.7 | 0.5 | 9.2 | 12.4 |

As is apparent from the Table 9, in the strain into which the NoΔ12-DES gene, the NoΔ6-DES gene and the Noω3-DES gene were introduced ((delta12 DES+delta6 DES+omega3 DES) strain), the proportion of C20:n (especially, C20:5Δ5,8,11,14,17) in the TAG was improved, in comparison with that in the wild type strain.

Further, in the strain into which the NoΔ12-DES gene, the NoΔ6-DES gene, the Noω3-DES gene, and the NoΔ6-ELO gene were introduced ((delta12 DES+delta6 DES+omega3 DES+delta6 ELO) strain), the proportion of C20:n (especially, C20:3Δ8,11,14) was further increased, in comparison with that in the strain into which the NoΔ12-DES gene, the NoΔ6-DES gene, and the Noω3-DES gene were introduced ((delta12 DES+delta6 DES+omega3 DES) strain).

From these results, it was found that the productivity of PUFA is further improved by enhancing expression of the Δ6-ELO in addition to the Δ12-DES, the Δ6-DES and the ω3-DES.

As described above, in the synthetic pathway of PUFA in the algae belonging to the genus *Nannochloropsis*, the Δ12-DES and the Δ6-DES each are the enzyme that catalyzes the reaction in the rate-limiting step. Then, the production amount of PUFA can be significantly increased by enhancing the expression of the Δ12-DES and the Δ6-DES. Further, productivity of the PUFA can be improved by culturing the transformant of an alga belonging to the genus *Nannochloropsis*, in which the expressions of the Δ12-DES and the Δ6-DES are enhanced.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2016-174752 filed in Japan on Sep. 7, 2016, which is entirely herein incorporated by reference.

What is claimed is:

1. A method of producing fatty acids or lipids containing the same as components, comprising:

culturing a transformed alga belonging to the genus *Nannochloropsis*, wherein the alga has been transformed with a gene encoding a Δ12-desaturase and a gene encoding a Δ6 desaturase, and producing fatty acids or lipids containing the same as components during the culturing;

wherein expression of the gene encoding the Δ12-desaturase and expression of the gene encoding the Δ6-desaturase are both enhanced in the transformed alga during the culturing;

wherein the Δ12-desaturase is the following protein (A) or (B):

(A) a protein consisting of the amino acid sequence set forth in SEQ ID NO: 1; or (B) a protein consisting of an amino acid sequence having 90% or more identity with the amino acid sequence of the protein (A), and having Δ12-desaturase activity;

wherein the Δ6-desaturase is the following protein (E) or (F):

(E) a protein consisting of the amino acid sequence set forth in SEQ ID NO: 3; or (F) a protein consisting of an amino acid sequence having 90% or more identity with the amino acid sequence of the protein (E), and having Δ6-desaturase activity;

and wherein productivity of C20:n polyunsaturated fatty acids is improved as compared to that in a wild-type alga that is the same as the transformed alga except that it has not been transformed with the genes encoding the Δ12-desaturase and the Δ6-desaturase.

2. A method of modifying a composition of fatty acids or lipids containing the same as components comprising:

transforming an alga belonging to the genus *Nannochloropsis* with a gene encoding a Δ12-desaturase and a gene encoding a Δ6-desaturase to produce a transformed alga, and culturing the transformed alga, wherein expression of the gene encoding the Δ12-desaturase and the gene encoding the Δ6-desaturase is enhanced during the culturing;

wherein the Δ12-desaturase is the following protein (A) or (B):

(A) a protein consisting of the amino acid sequence set forth in SEQ ID NO: 1; or (B) a protein consisting of an amino acid sequence having 90% or more identity with the amino acid sequence of the protein (A), and having Δ12-desaturase activity;

wherein the Δ6-desaturase is the following protein (E) or (F):

(E) a protein consisting of the amino acid sequence set forth in SEQ ID NO: 3; or (F) a protein consisting of an amino acid sequence having 90% or more identity with the amino acid sequence of the protein (E), and having Δ6-desaturase activity, and wherein the proportion of C20:n polyunsaturated fatty acids that are produced by the culturing is greater than that produced by culturing a wild-type alga that is the same as the transformed alga except that it that has not been transformed with the genes encoding the Δ12-desaturase and the Δ6-desaturase.

3. The method according to claim 1, wherein the productivity of C20:n fatty acids is the productivity of the sum of fatty acids that are C20:3(Δ8,11,14), C20:4(Δ5,8,11,14) and C20:5(Δ45,8,11,14,17) fatty acids.

4. The method according to claim 1, wherein protein (B) is a protein consisting of an amino acid sequence having 95% or more identity with the amino acid sequence of the protein (A), and having Δ12-desaturase activity.

5. The method according to claim 1, wherein protein (F) is a protein consisting of an amino acid sequence having 95% or more identity with the amino acid sequence of the protein (E), and having Δ6-desaturase activity.

6. The method according to claim 1, wherein, in the transformed alga, expression of at least one gene encoding an enzyme selected from the group consisting of an ω3-desaturase, a Δ5-desaturase, a Δ9-desaturase and a Δ6-elongase is also enhanced.

7. The method according to claim 6, wherein the transformed alga has been transformed with the gene encoding the ω3-desaturase, Δ5-desaturase, Δ9-desaturase or Δ6-elongase.

8. The method according to claim 6, wherein the ω3-desaturase is the following protein (I) or (J):

(I) a protein consisting of the amino acid sequence set forth in SEQ ID NO: 5; or (J) a protein consisting of an amino acid sequence having 90% or more identity with the amino acid sequence of the protein (I), and having ω3-desaturase activity.

9. The method according to claim 6, wherein the Δ5-desaturase is the following protein (M) or (N):

(M) a protein consisting of the amino acid sequence set forth in SEQ ID NO: 7; or (N) a protein consisting of an amino acid sequence having 90% or more identity with the amino acid sequence of the protein (M), and having Δ5-desaturase activity.

10. The method according to claim 6, wherein the Δ9-desaturase is the following protein (Q) or (R):

(Q) a protein consisting of the amino acid sequence set forth in SEQ ID NO: 9; or (R) a protein consisting of an amino acid sequence having 90% or more identity with the amino acid sequence of the protein (Q), and having Δ9-desaturase activity.

11. The method according to claim 6, wherein the Δ6-elongase is the following protein (U) or (V):

(U) a protein consisting of the amino acid sequence set forth in SEQ ID NO: 74; or (V) a protein consisting of an amino acid sequence having 90% or more identity with the amino acid sequence of the protein (U), and having Δ6-elongase activity.

12. The method according to claim 1, wherein the fatty acids or lipids contain dihomo-γ-linolenic acid, arachidonic acid or eicosapentaenoic acid, or an ester thereof.

13. A transformant of an alga belonging to the genus *Nannochloropsis,* wherein the transformant has been transformed with a gene encoding a Δ12-desaturase and a gene encoding a Δ6-desaturase, and wherein expression of the gene encoding the Δ12-desaturease, and expression of the gene encoding the Δ6-desaturease, is enhanced in the transformant as compared to expression of those genes in the alga before being transformed, wherein the Δ12-desaturase is the following protein (A) or (B):

(A) a protein consisting of the amino acid sequence set forth in SEQ ID NO: 1; or (B) a protein consisting of an amino acid sequence having 90% or more identity with the amino acid sequence of the protein (A), and having Δ12-desaturase activity;

wherein the Δ6-desaturase is the following protein (E) or (F):

(E) a protein consisting of the amino acid sequence set forth in SEQ ID NO: 3; or (F) a protein consisting of an amino acid sequence having 90% or more identity with the amino acid sequence of the protein (E), and having Δ6-desaturase activity;

and wherein, when the transformant is cultured, productivity of C20:n polyunsaturated fatty acids is improved as compared to that in a wild-type alga that is the same except that has not been transformed with the gene encoding the Δ12-desaturase and with the gene encoding the Δ6-desaturase.

14. The transformant according to claim 13, wherein protein (B) is a protein consisting of an amino acid sequence having 95% or more identity with the amino acid sequence of the protein (A), and having Δ12-desaturase activity.

15. The transformant according to claim 13, wherein protein (F) is a protein consisting of an amino acid sequence having 95% or more identity with the amino acid sequence of the protein (E), and having Δ6-desaturase activity.

16. The transformant according to claim 13, wherein, in the transformant, expression of at least one gene encoding an enzyme selected from the group consisting of an ω3-desaturase, a Δ5-desaturase, a Δ9-desaturase and a Δ6-elongase is also enhanced.

17. The transformant according to claim 16, wherein the ω3-desaturase is the following protein (I) or (J):

(I) a protein consisting of the amino acid sequence set forth in SEQ ID NO: 5; or (J) a protein consisting of an amino acid sequence having 90% or more identity with the amino acid sequence of the protein (I), and having ω3-desaturase activity.

18. The transformant according to claim 16, wherein the Δ5-desaturase is the following protein (M) or (N):

(M) a protein consisting of the amino acid sequence set forth in SEQ ID NO: 7; or (N) a protein consisting of an amino acid sequence having 90% or more identity with the amino acid sequence of the protein (M), and having Δ5-desaturase activity.

19. The transformant according to claim 16, wherein the Δ9-desaturase is the following protein (Q) or (R):

(Q) a protein consisting of the amino acid sequence set forth in SEQ ID NO: 9; or (R) a protein consisting of an amino acid sequence having 90% or more identity with the amino acid sequence of the protein (Q), and having Δ9-desaturase activity.

20. The method according to claim 16, wherein the Δ6-elongase is the following protein (U) or (V):

(U) a protein consisting of the amino acid sequence set forth in SEQ ID NO: 74; or (V) a protein consisting of an amino acid sequence having 90% or more identity with the amino acid sequence of the protein (U), and having Δ6-elongase activity.

21. The method of claim 1, wherein productivity of lipids that comprise C20:5 polyunsaturated fatty acids as components is improved.

22. The method of claim 2, wherein the proportion of C20:5 polyunsaturated fatty acids is greater than that produced by culturing the wild-type alga.

23. The transformant of claim 13, wherein productivity of C20:5 polyunsaturated fatty acids or lipids containing the same is improved in the transformant as compared to the productivity of C20:5 polyunsaturated fatty acids before transformation.

* * * * *

SEQUENCE LISTING

```
<160> NUMBER OF SEQ ID NOS: 75

<210> SEQ ID NO 1
<211> LENGTH: 438
<212> TYPE: PRT
<213> ORGANISM: Nannochloropsis oculata

<400> SEQUENCE: 1

Met Gly Arg Gly Gly Glu Lys Thr Val Thr Pro Leu Arg Lys Lys Thr
1               5                   10                  15

Leu Leu Asp Ala Ala Ser Thr Ile Ser Gly Thr Val Arg Pro Ser Lys
            20                  25                  30

Ala Val Glu Ala Leu Pro Thr Glu Glu Leu Arg Lys Lys Ala Ala Gln
        35                  40                  45

Tyr Gly Ile Asn Thr Ser Val Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Pro Phe Thr Leu Ser Asp Ile Lys Asn Ala Val
                85                  90                  95

Pro Arg His Cys Phe Glu Arg Ser Leu Ser Thr Ser Leu Phe His Leu
            100                 105                 110

Thr Ile Asp Leu Ile Gln Val Ala Val Leu Gly Tyr Leu Ala Ser Leu
        115                 120                 125

Leu Gly His Ser Asp Val Pro Pro Met Ser Arg Tyr Ile Leu Trp Pro
    130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
                165                 170                 175

Asn Phe Phe Gly Trp Leu Leu His Ser Ala Leu Leu Val Pro Tyr His
            180                 185                 190

Ser Trp Arg Ile Ser His Gly Lys His His Asn Asn Thr Gly Ser Cys
        195                 200                 205

Glu Asn Asp Glu Val Phe Ala Pro Pro Ile Lys Glu Glu Leu Met Asp
    210                 215                 220

Glu Ile Leu Leu His Ser Pro Leu Ala Asn Leu Val Gln Ile Ile Ile
225                 230                 235                 240

Met Leu Thr Ile Gly Trp Met Pro Gly Tyr Leu Leu Leu Asn Ala Thr
                245                 250                 255

Gly Pro Arg Lys Tyr Lys Gly Leu Ser Asn Ser His Phe Asn Pro Asn
            260                 265                 270

Ser Ala Leu Phe Ser Pro Lys Asp Arg Leu Asp Ile Ile Trp Ser Asp
        275                 280                 285

Ile Gly Phe Phe Val Ala Leu Ala Cys Val Val Tyr Ala Cys Val Gln
    290                 295                 300
```

```
Phe Gly Phe Gln Thr Val Gly Lys Tyr Tyr Leu Leu Pro Tyr Met Val
305                 310                 315                 320

Val Asn Tyr His Leu Val Leu Ile Thr Tyr Leu Gln His Thr Asp Val
                325                 330                 335

Phe Ile Pro His Phe Arg Gly Ser Glu Trp Thr Trp Phe Arg Gly Ala
            340                 345                 350

Leu Cys Thr Val Asp Arg Ser Phe Gly Trp Leu Leu Asp His Thr Phe
        355                 360                 365

His His Ile Ser Asp Thr His Val Cys His His Ile Phe Ser Lys Met
    370                 375                 380

Pro Phe Tyr His Ala Gln Glu Ala Ser Glu His Ile Arg Lys Ala Leu
385                 390                 395                 400

Gly Asp Tyr Tyr Leu Lys Asp Asp Thr Pro Ile Trp Lys Ala Leu Trp
                405                 410                 415

Arg Ser Tyr Thr Leu Cys Lys Tyr Val Asp Ser Glu Glu Thr Thr Val
            420                 425                 430

Phe Tyr Lys Gln Arg Ala
        435


<210> SEQ ID NO 2
<211> LENGTH: 1317
<212> TYPE: DNA
<213> ORGANISM: Nannochloropsis oculata

<400> SEQUENCE: 2

atgggacgcg gcggtgagaa gacggtgacc cctcttcgca aaaaaaccct cctggatgcc      60

gcttccacga tcagcggcac agtcagacca agcaaggcag tagaggccct gcccacggag     120

gagctgcgta agaaggccgc acaatacggt atcaacactt cggtcgaccg cgaaacactg     180

ctgagggagc tggctcccta cggcgatatc ctcctccgca atgacgcccc taaatccctg     240

ccccttgccc ctcctccttt caccctctcc gacatcaaga acgctgttcc ccgtcactgc     300

tttgagcgtt ccctctccac ctccctcttc cacttgacca tcgacttgat ccaagtcgct     360

gtcctcgggt accttgcctc attactgggc cactccgacg tcccgcccat gtctcgttat     420

attctatggc cgttgtactg gtacgcgcaa ggctctgtgc tgacgggagt gtgggtcatt     480

gcccacgagt gcgggcacca atcgttttcg ccttacgaga gcgtgaacaa cttctttggg     540

tggctcttgc actcggcctt gcttgtgccc tatcactctt ggaggatttc ccatggaaag     600

caccacaaca acacggggag ctgcgagaat gacgaggtct ttgcgccgcc tattaaggag     660

gaactgatgg acgagatttt gcttcactcc cctttggcga atctggtgca gataatcata     720

atgttgacca tcggatggat gccggggtac ctgctcctga acgctacggg gcctaggaaa     780

tacaagggac tgagcaatag ccactttaac ccaaattcgg cgttgttttc tccgaaggac     840

cgtctggaca ttatttggtc cgacattggg tttttcgtgg ccttggcctg cgtggtatat     900

gcctgtgtgc agtttggatt tcaaacggtg ggaaagtatt acctgctgcc gtacatggtg     960

gtcaattatc acctggtcct catcacgtac ctgcagcaca cggacgtctt catcccccac    1020

tttcgggggga gcgagtggac gtggtttagg ggcgcccttt gcacggtcga ccgatccttc    1080

ggctggcttt tggaccatac gtttcaccat atcagtgaca ctcatgtgtg ccaccacatc    1140

ttcagcaaga tgccgttcta ccacgcgcag gaggcgagtg agcacattcg caaggcgttg    1200

ggcgactatt atttgaagga tgataccccg atttggaagg cattgtggcg aagttatacc    1260

ctgtgcaagt acgtggactc ggaggagacg acggtattct acaagcagcg ggcatag       1317
```

```
<210> SEQ ID NO 3
<211> LENGTH: 474
<212> TYPE: PRT
<213> ORGANISM: Nannochloropsis oculata

<400> SEQUENCE: 3

Met Gly Arg Gly Gly Glu Arg Val Glu Thr Thr Glu Ser Leu Ser Phe
1               5                   10                  15

Thr Ala Asp Lys Ala Gly Thr Ile Lys Gln Arg Gly Gly Lys Ile Thr
            20                  25                  30

Trp Asp Glu Val Arg Gln His Lys Thr Pro Gln Asp Ala Trp Leu Val
        35                  40                  45

Tyr Arg Asn Lys Val Tyr Asp Val Ser Gly Trp Gln Asp His Pro Gly
    50                  55                  60

Gly Asn Val Ile Phe Thr His Ala Gly Gly Asp Cys Thr Asp Ile Phe
65                  70                  75                  80

Ala Ala Phe His Pro Leu Gly Ala Thr Ser Tyr Leu Asp Pro Phe Tyr
                85                  90                  95

Ile Gly Glu Leu Glu Pro Gly Ser Asp Lys Lys Pro Ala Ala Gln Ala
            100                 105                 110

Asn Phe Glu Arg Ala Tyr Arg Asp Leu Arg Gly Lys Leu Ile Ala Gly
        115                 120                 125

Gly Phe Phe Lys Ala Asn Pro Leu Tyr Tyr Val Trp Lys Val Val Ser
    130                 135                 140

Thr Val Ala Leu Ala Val Gly Ala Trp Met Leu Val Ala Trp Ser Gln
145                 150                 155                 160

Asn Leu Gly Val Gln Met Leu Ser Ala Phe Leu Val Ala Leu Phe Trp
                165                 170                 175

Gln Gln Cys Gly Trp Leu Ala His Asp Phe Leu His His Gln Val Phe
            180                 185                 190

Lys Asn Arg Ala Leu Gly Asp Leu Ala Gly Ile Val Ile Gly Asn Val
        195                 200                 205

Phe Gln Gly Phe Ser Val Ala Trp Trp Lys Asn Lys His Asn Thr His
    210                 215                 220

His Ala Val Pro Asn Leu Val Glu Ser Ser Pro Asp Ala Gln Asp Gly
225                 230                 235                 240

Asp Pro Asp Ile Asp Thr Met Pro Ile Leu Ala Trp Ser Leu Lys Met
                245                 250                 255

Ala Asp Arg Ala Gln Gln Tyr Ser Trp Gly Pro Phe Phe Val Arg His
            260                 265                 270

Gln Ser Leu Leu Tyr Phe Pro Ile Leu Leu Val Ala Arg Ile Ser Trp
        275                 280                 285

Leu Met Gln Ser Phe Leu Phe Val Phe Asp Ser Val Pro Gly Ala Ser
    290                 295                 300

Leu Trp Ala Thr Lys Gly Ala Thr Ala Glu Arg Gln Ala Ile Lys Asn
305                 310                 315                 320

Val Gly Leu Glu Lys Val Gly Leu Val Ala His Tyr Leu Trp Tyr Gly
                325                 330                 335

Ala Leu Met Leu Cys His Met Ser Leu Ala Arg Ala Leu Leu Tyr Phe
            340                 345                 350

Leu Ala Ser Gln Met Met Cys Gly Phe Leu Leu Ala Leu Val Phe Gly
        355                 360                 365

Leu Gly His Asn Gly Met Ala Val Tyr Asp Ala Asp Ala Arg Pro Asp
```

```
    370                 375                 380

Phe Trp Lys Leu Gln Val Thr Thr Thr Arg Asn Val Thr Gly Ser Trp
385                 390                 395                 400

Leu Val Gln Trp Phe Cys Gly Gly Leu Gly Tyr Gln Val Asp His His
                405                 410                 415

Leu Phe Pro Met Ile Pro Arg His Arg Leu Gly Lys Leu His Gly Leu
            420                 425                 430

Val Glu Gly Phe Cys Lys Asp His Gly Val Lys Tyr His Glu Thr Asn
        435                 440                 445

Met Trp Glu Gly Thr Lys Glu Val Leu Ala His Leu Ser Ser Val Thr
    450                 455                 460

Lys Glu Phe Val Ala Asp Phe Pro Ala Met
465                 470
```

<210> SEQ ID NO 4
<211> LENGTH: 1425
<212> TYPE: DNA
<213> ORGANISM: Nannochloropsis oculata

<400> SEQUENCE: 4

```
atgggacgcg gtggcgagcg ggtcgagacg acggagtctt tgagcttcac ggccgacaag     60

gcggggacca tcaagcagcg tggggggaag atcacatggg atgaggtgcg tcagcacaag    120

acgcctcagg acgcttggct cgtgtatagg aataaggtct acgacgtgtc gggctggcaa    180

gatcaccccg gggggaacgt catcttcact cacgccggcg gggactgcac ggatattttc    240

gcggcgttcc accctcttgg cgccacctct tatcttgatc cattttacat tggcgagctg    300

gagccgggct cggacaagaa gcccgcagcg caggcgaact ttgagcgggc ctacagggat    360

ctcaggggga agcttatcgc gggtgggttt ttcaaggcga atcctttgta ctatgtctgg    420

aaggtagtat cgacagttgc ccttgctgta ggtgcgtgga tgctggtggc ttggtcgcag    480

aacctgggcg tgcagatgct gtctgcgttt ttggtggctc tgttctggca gcaatgtggc    540

tggttggccc atgacttcct gcaccaccag gtatttaaga accgtgcgtt gggtgacctg    600

gccggcatcg ttatcggcaa tgtcttccag ggtttctccg tggcatggtg gaagaacaag    660

cataacactc accacgcggt gcccaacctc gtcgagtcct ctccggacgc gcaagacgga    720

gaccctgaca ttgacaccat gcccatactg gcctggtcgc tcaagatggc cgacagggcg    780

cagcaatact catggggacc cttctttgtc aggcatcagt cgctgctata cttccccatc    840

ctgctcgtgg cgcggatttc atggttgatg cagtcgttct tgtttgtctt tgactccgtc    900

cctggagcga gtctgtgggc aaccaagggc gcgacggctg agagacaggc gatcaagaat    960

gtcgggttgg agaaggtggg gctggttgcg cactacctgt ggtacggtgc gctgatgctg   1020

tgccacatgt ccctggcccg cgccctgctg tacttcctgg cgagccagat gatgtgcggg   1080

ttcttgctcg cgcttgtttt cgggcttggg cacaacggca tggctgttta cgacgcggac   1140

gcccggcccg acttctggaa gctgcaggtg acgacgacga ggaacgtgac gggctcgtgg   1200

ttggtgcagt ggttctgtgg cggcctcggc taccaggtgg accaccacct gttccccatg   1260

atcccgcggc accgcctagg gaagctccac gggctcgtgg agggtttctg caaggatcac   1320

ggggtgaagt accacgagac gaatatgtgg gaggggacca aagaggtgtt ggctcacttg   1380

agcagtgtga cgaaagagtt cgtggccgat ttccccgcca tgtaa                    1425
```

<210> SEQ ID NO 5
<211> LENGTH: 410

```
<212> TYPE: PRT
<213> ORGANISM: Nannochloropsis oculata

<400> SEQUENCE: 5

Met Val Glu Gln Thr Leu Pro Thr Leu Ser Gln Ile Lys Lys Ala Ile
1               5                   10                  15

Pro Glu Lys Cys Phe Gln Lys Ser Leu Leu Arg Ser Phe Tyr Tyr Met
            20                  25                  30

Leu Arg Asp Phe Ala Ala Leu Ala Ala Leu Tyr Phe Val Tyr Pro Thr
        35                  40                  45

Val Gln Ala Lys Tyr Gly Leu Pro Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Leu Asn Asp Ile Cys Gly His
                85                  90                  95

Ile Cys His Ala Pro Leu Met Val Pro Tyr Trp Pro Trp Gln Lys Ser
            100                 105                 110

His Arg Leu His His Met Tyr His Asn His Leu Thr Lys Asp Met Ser
        115                 120                 125

His Pro Trp Met Thr Lys Glu Val Phe Glu Asp Leu Thr Pro Phe Glu
    130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Met Asp Gly Ser His Val Val Pro Phe
                165                 170                 175

Ser Pro Leu Phe Thr Asp Thr Lys Glu Arg Val Gln Cys Ala Val Ser
            180                 185                 190

Thr Leu Gly Met Val Val Ala Gly Ala Leu Val Tyr Ile Gly Leu Glu
        195                 200                 205

Gly Gly Lys Glu Gly Gly Met Ala Arg Ile Gly Ser Ile Tyr Val Val
    210                 215                 220

Pro Leu Leu Val Phe Asn Ala Trp Ile Thr Met Val Thr Tyr Leu Gln
225                 230                 235                 240

His His Asp Glu Asp Thr Lys Val Tyr Ala Glu Gly Glu Trp Asn Tyr
                245                 250                 255

Ile Lys Gly Ala Leu Glu Thr Ile Asp Arg Glu Tyr Gly Met Gly Ile
            260                 265                 270

Asp Asp Leu Ser His Asn Ile Thr Asp Gly His Val Ala His His Leu
        275                 280                 285

Phe Phe Thr Gln Ile Pro His Tyr His Leu Thr Ala Ala Thr Ala Ala
    290                 295                 300

Val Arg Gln Cys Leu Gln Pro Thr Gly Thr Tyr Lys Lys Arg Arg Ser
305                 310                 315                 320

Trp Asn Phe Leu Ala Arg Phe Thr Glu Leu Asn Tyr Arg Leu Lys Tyr
                325                 330                 335

Val Ala Gly Gln Gly Val Leu Ser Tyr Val Asp Trp Glu Val Ala Arg
            340                 345                 350

Lys Thr Pro Ala Ser Ala Val Thr Ser Ser Phe Ser Ser Ser Ser Ser
        355                 360                 365

Ser Ser Leu Pro Ala Glu Ala Ala Val Lys Ala Ala Ala Val Pro
    370                 375                 380

Val Ala Ala Val Ala Ala Pro Val Arg Glu Gly Arg Pro Thr Arg Lys
385                 390                 395                 400
```

```
Arg Ser Pro Thr Arg Ser Ser Ser Pro Pro
                405                 410


<210> SEQ ID NO 6
<211> LENGTH: 1233
<212> TYPE: DNA
<213> ORGANISM: Nannochloropsis oculata

<400> SEQUENCE: 6

atggttgagc aaacgttacc gaccttgtcc cagatcaaga aagccatccc cgagaaatgc     60

ttccagaaat ccctcctccg ctccttttac tacatgctga gggacttcgc ggccttggcg    120

gcactctact ttgtttatcc cacagttcag gccaagtatg gattgcctgg tttgtttgtg    180

tggtggaacc tcgcaggctt tttcatgtgg tgcctcttcg tgataggcca cgattgcggc    240

catggctcct tctccgagta caagtggctc aatgacattt gcggtcacat ttgccacgcc    300

cccttgatgg tgccttactg gccttggcag aagtcccacc gccttcacca catgtaccac    360

aaccacctga ctaaggacat gtcacacccg tggatgacca aggaggtgtt cgaggacttg    420

accccattcg agcaggcgtt gctggagaac ccgctgtccc tcttcatcaa gtacaccttc    480

ctttacctct ttgcgggcaa gatggatggc agccatgtag ttccattctc ccccctcttc    540

accgacacca aggagcgggt gcaatgcgca gtgtcgacgc tgggtatggt cgtcgcaggc    600

gcccttgtgt acatcgggct cgagggcggg aaggagggag ggatggcgag gataggatcc    660

atttatgtgg tgccgttgct ggtgttcaat gcctggatca cgatggtgac atacctgcag    720

caccacgatg aggacaccaa ggtttatgca gagggggagt ggaactacat caaggggggcc    780

ctggagacga tcgaccgcga atacggcatg gggattgacg acctctccca caatatcacg    840

gatggccacg tggcgcacca cctcttcttc acgcagatcc cgcactacca cctgacggcg    900

gccacggccg ctgtgagaca atgcctgcaa cctacgggga cctacaagaa gaggaggagc    960

tggaattttc tcgctcgttt cacggagctt aactaccgtt tgaaatacgt cgcgggccag   1020

ggcgtgctct cctatgtgga ttgggaggtc gctcgcaaga cccctgcttc cgccgtcacc   1080

tcctctttct cttcctcctc ctcttcctcc cttccggcag aggctgctgt caaggcggct   1140

gctgccgttc ccgttgctgc tgttgctgct cccgtccgag aaggaagacc aacacgcaag   1200

cgctctccca cccgttcatc ctcccctccg taa                                1233


<210> SEQ ID NO 7
<211> LENGTH: 526
<212> TYPE: PRT
<213> ORGANISM: Nannochloropsis oculata

<400> SEQUENCE: 7

Met Pro Pro Gln Asn Asp Ala Ala Leu Gly Gly Gly Phe Phe Arg Asn
1               5                   10                  15

Arg Phe Thr Arg Lys Asn Ser Thr Ser Ser Leu Ile Ile Asp Asp Thr
            20                  25                  30

Pro Ala Thr Ser Thr Glu Ser Val Ala Ala Ala Glu Ala Thr Val Ala
        35                  40                  45

Ala Thr Ala Ala Ala Ala Ala Gly Gly Lys Thr Tyr Thr Trp Glu Glu
    50                  55                  60

Val Ala Glu His Asn Thr Glu Lys Ser Leu Trp Val Thr Val Arg Gly
65                  70                  75                  80

Lys Val Tyr Asp Ile Ser Ser Trp Val Asn Asn His Pro Gly Gly Lys
                85                  90                  95
```

```
Glu Ile Leu Leu Leu Ala Ala Gly Arg Asp Ile Thr Tyr Ala Phe Asp
            100                 105                 110

Ser Tyr His Pro Phe Thr Glu Lys Pro Thr Gln Val Leu Gly Lys Phe
        115                 120                 125

Glu Ile Gly Thr Val Ser Ser His Glu Phe Pro Gln Tyr Lys Pro Asp
    130                 135                 140

Thr Arg Gly Phe Tyr Lys Thr Leu Cys Thr Arg Val Gly Asp Tyr Phe
145                 150                 155                 160

Lys Gln Glu Lys Leu Asn Pro Lys Asp Pro Phe Pro Gly Ile Trp Arg
                165                 170                 175

Met Leu Leu Val Ala Met Val Ala Val Ala Ser Phe Met Val Cys Asn
            180                 185                 190

Gly Trp Val Gly Leu Glu Gly Gly Val Leu Ala Gly Trp Gly Ala Arg
        195                 200                 205

Phe Val Ala Ala Val Val Phe Gly Val Cys Gln Ala Leu Pro Leu Leu
    210                 215                 220

His Val Met His Asp Ser Ser His Leu Ala Phe Gly Asn Thr Glu Arg
225                 230                 235                 240

Trp Trp Gln Met Gly Gly Arg Leu Ala Met Asp Phe Phe Ala Gly Ala
                245                 250                 255

Asn Met Thr Ser Trp His Asn Gln His Val Ile Gly His His Ile Tyr
            260                 265                 270

Thr Asn Val Phe Met Ala Asp Pro Asp Leu Pro Asp Lys Ser Ala Gly
        275                 280                 285

Asp Pro Arg Arg Leu Val Lys Lys Gln Ala Trp Glu Gly Met Tyr Lys
    290                 295                 300

Trp Gln His Leu Tyr Leu Pro Pro Leu Tyr Gly Ile Leu Gly Ile Lys
305                 310                 315                 320

Phe Arg Val Gln Asp Val Met Glu Thr Tyr Gly Ser Gly Ser Asn Gly
                325                 330                 335

Pro Val Arg Val Asn Pro Leu Ser Pro Trp Gln Trp Gly Glu Met Ile
            340                 345                 350

Phe Thr Lys Leu Phe Trp Phe Gly Trp Arg Val Val Phe Pro Leu Met
        355                 360                 365

Ser Ala Ser Phe Arg Thr Ser Met Ala Thr Phe Trp Pro Leu Phe Phe
    370                 375                 380

Val Ser Glu Phe Met Thr Gly Tyr Phe Leu Ala Phe Asn Phe Gln Val
385                 390                 395                 400

Ser His Val Ser Ser Glu Cys Asp Tyr Pro Leu Gly Glu Ala Pro Arg
                405                 410                 415

Glu Glu Ala Val Glu Gly Ser Ala Gly Gly Lys Glu Gly Ile Lys Asp
            420                 425                 430

Glu Trp Ala Val Ser Gln Val Lys Ser Ser Val Asp Tyr Ala His Asn
        435                 440                 445

Asn Ala Leu Thr Thr Phe Leu Cys Gly Ala Leu Asn Tyr Gln Val Thr
    450                 455                 460

His His Leu Phe Pro Thr Val Ser Gln Tyr His Tyr Pro Lys Ile Ala
465                 470                 475                 480

Pro Ile Ile Gln Glu Val Cys Lys Glu Phe Asn Val Asp Tyr Lys Val
                485                 490                 495

Leu Pro Asp Phe Val Thr Ala Phe His Ala His Ile Ala His Leu Lys
            500                 505                 510
```

```
Ala Leu Gly Glu Arg Gly Glu Ala Ala Glu Val His Met Gly
        515                 520                 525


<210> SEQ ID NO 8
<211> LENGTH: 1581
<212> TYPE: DNA
<213> ORGANISM: Nannochloropsis oculata

<400> SEQUENCE: 8

atgcctcccc agaacgacgc tgctcttgga ggcggttttt ttcgcaaccg cttcacccga      60

aagaactcca cttcctccct catcatcgat gacacgccgg ccaccagcac tgagtccgtg     120

gcggcagcag aagcaacagt agcagcgaca gcagccgccg ccgccggcgg taagacctac     180

acatgggagg aagtggcgga gcacaacact gagaagagcc tgtgggtgac cgtgcgagga     240

aaggtgtatg acatcagcag ctgggtgaac aaccaccccgg gagggaagga gattctgttg    300

ttggcggcgg gcagggatat cacctatgcc ttcgactctt accacccttt cacggagaag     360

ccgacgcagg tcctgggcaa gtttgagatc ggcactgtgt cctcccacga attcccgcag     420

tacaaacccg acacccgggg cttctacaag acgctgtgca cgcgcgtagg tgactacttt     480

aagcaggaga agttgaaccc taaggaccct ttcccaggga tatggcggat gctcctggtg     540

gcgatggtgg ccgtagcctc ctttatggtg tgcaacgggt gggtggggct ggaaggaggg     600

gtactggcag gatggggagc gaggtttgtg gcggcggtgg tgtttggtgt gtgccaggcg     660

ttgccccttc tgcacgtcat gcacgactca tcccacctgg cgttcgggaa cacggagagg     720

tggtggcaaa tgggggggag gctggccatg gatttcttcg cgggggcgaa catgacgagt     780

tggcacaatc agcacgtgat agggcatcac atttatacga atgtgttcat ggctgacccg     840

gacttgcccg ataagagcgc tggggacccg aggcggctgg ttaagaagca ggcatgggag     900

gggatgtaca agtggcagca cctctacttg ccacctttgt acggcatcct gggcatcaag     960

ttccgggtgc aagacgtgat ggagacgtac gggagcgggt cgaatgggcc ggtgagggtt    1020

aacccccttga gcccctggca gtggggggag atgatcttca ccaagctctt ctggttcggc   1080

tggcgcgtgg tgttcccgct catgtcggca agctttcgga cgagcatggc cacgttctgg    1140

cccttgttct tcgtgagtga gttcatgacg ggatacttcc tggcgttcaa tttccaggtg    1200

tcacacgtct cgtccgagtg cgattatccg ctgggcgagg cgccgaggga ggaagcggta    1260

gagggctcgg caggagggaa ggaaggtatc aaggacgaat gggccgtgag ccaggtgaag    1320

agtagcgtgg actacgccca caataacgct ttgacgacct tcctgtgcgg ggctttgaac    1380

taccaggtga cgcaccacct gttccccact gtaagtcagt accactaccc caagatcgcg    1440

cccatcatcc aggaggtatg caaggagttt aacgtcgact acaaggtcct gcccgatttt    1500

gtgacggcgt tccatgcgca cattgcgcat ttgaaggcct tgggagagag ggcgaggcg     1560

gcggaggtgc acatgggtta g                                              1581


<210> SEQ ID NO 9
<211> LENGTH: 359
<212> TYPE: PRT
<213> ORGANISM: Nannochloropsis oculata

<400> SEQUENCE: 9

Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
            20                  25                  30
```

```
Val His Leu Ala Gly Tyr Ile Gly Leu Thr Thr Ile Leu Ala Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Asn
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
    210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
        275                 280                 285

Arg Lys Arg Ala Thr Gly Ala Trp Ala Lys Leu Lys Glu Ser Arg Ala
    290                 295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Thr Asp Lys Gly Ala Gln Gln Pro Gly Trp Glu Glu
            340                 345                 350

Ser Asn His Pro Lys Tyr Asn
        355
```

<210> SEQ ID NO 10
<211> LENGTH: 1080
<212> TYPE: DNA
<213> ORGANISM: Nannochloropsis oculata

<400> SEQUENCE: 10

```
atggtcttcc agctcgcccg agactctgtc tcggccctgg tctatcattt caaagaagga     60

aaccttaact ggcctatgat tatctacctc gtccttgtcc acttggcggg ctacatcggt    120

ctgactacca ttctggcttg caaatggcaa actctcctcg aagcgttcat cctatggccc    180

atcaccgggc tggggattac tgccggcgta caccgacttt gggcacaccg ttcgtacaat    240
```

gccacgttgc cttatcgcat cctgttgatg ttgttcaact caattgcgaa ccaaggcagc 300
atctaccact ggtcccggga ccaccgcgtg caccacaagt actccgagac tgatgctgac 360
ccacataacg ccacccgtgg cttcttcttc gcgcacatgg gctggctcat tgttaagaag 420
caccccaagg tcgtcgaagg ggggaagcaa ctcgatttct ccgatttggc tgccgatccc 480
gtggtgcgat tccagcgtga ttgggatccg tggttcgccc agtttatgtg ctttgtcatg 540
ccggcgcttg ttgcatcgag gttctggggt gaggcgttct ggaacgcctt ttgggtggcg 600
ggggctttga ggtatatgtt ggtgctgcac ttcacctgga tggttaacag tgcggcgcac 660
ttgtatggcg accacccgta cgaccctacc atgtggccgg cggagaaccc gttggtatcg 720
gtagtggcga tcggagaagg ctggcataac tggcaccatc gttacccccta cgactacgcg 780 gcttccgagt ttgggatttc gcagcagttc aacccgacca aggcgttcat tgattttttt 840
gcggccatag ggatggtgac gaaccgaaaa cgtgcgacgg gggcttgggc aaagctcaag 900
gaatccaggg caagggatgc ggcgaatggg aagagcatga aagatttcaa gggaagaggc 960
tcggggtcag actatggtac gacaaacacc aattacgcgg tgtcgaacaa gacagtggtg 1020
accgacaagg gggcgcaaca accagggtgg gaggagagca atcaccccaa gtacaactaa 1080

<210> SEQ ID NO 11
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 11
atggccaagc tgaccagcgc cgttccggtg ctcaccgcgc gcgacgtcgc cggagcggtc 60
gagttctgga ccgaccggct cgggttctcc cgggacttcg tggaggacga cttcgccggt 120
gtggtccggg acgacgtgac cctgttcatc agcgcggtcc aggaccaggt ggtgccggac 180
aacaccctgg cctgggtgtg ggtgcgcggc ctggacgagc tgtacgccga gtggtcggag 240
gtcgtgtcca cgaacttccg ggacgcctcc gggccggcca tgaccgagat cggcgagcag 300
ccgtgggggc gggagttcgc cctgcgcgac ccggccggca actgcgtgca cttcgtggcc 360
gaggagcagg actaa 375

<210> SEQ ID NO 12
<211> LENGTH: 500
<212> TYPE: DNA
<213> ORGANISM: Nannochloropsis gaditana

<400> SEQUENCE: 12
actgcgcatg gattgaccga cggccggttg ccaacttttg gggtcggccc ccctttttcta 60 gcccttgccc gtccagcaat taaaaattat caacggcata ccggcactgg aagcttcggg 120
tttacaattt tggcttgcct tcctaatact gtaccgcgga gaacgtatga tattacagaa 180
aaatgccttg cacagttagc gcaaagggaa aacgtttctc cgccattgta ctttttggaa 240
gagggaaagc gattgtaaaa tatggctctc cgctacgaga gtttgggctg ttgatacatg 300
tgaaaataag tgtggacgac tttgaatgac ttgatcaggc tgtttgcaca tataaccagc 360
gcgcatgcac ttctgacatg tcaatgacga aatttcacac ttcaccaata aattgtatcc 420
ttacgttttg tctttctcac acgcacatat atgatcatag ataaaagcca atatcaagaa 480
gctgtctttt ttgtgaagca 500

<210> SEQ ID NO 13
<211> LENGTH: 37
<212> TYPE: DNA
<213> ORGANISM: Artificial Sequence
<220> FEATURE:
<223> OTHER INFORMATION: primer No. 13

<400> SEQUENCE: 13
cttttttgtg aagcaatggc caagttgacc agtgccg 37

<210> SEQ ID NO 14
<211> LENGTH: 36
<212> TYPE: DNA
<213> ORGANISM: Artificial Sequence
<220> FEATURE:
<223> OTHER INFORMATION: primer No. 14

<400> SEQUENCE: 14
tttcccccat cccgattagt cctgctcctc ggccac 36

<210> SEQ ID NO 15
<211> LENGTH: 35
<212> TYPE: DNA
<213> ORGANISM: Artificial Sequence
<220> FEATURE:
<223> OTHER INFORMATION: primer No. 15

<400> SEQUENCE: 15
cgagctcggt acccgactgc gcatggattg accga 35

<210> SEQ ID NO 16
<211> LENGTH: 28
<212> TYPE: DNA
<213> ORGANISM: Artificial Sequence
<220> FEATURE:
<223> OTHER INFORMATION: primer No. 16

<400> SEQUENCE: 16
tgcttcacaa aaaagacagc ttcttgat 28

<210> SEQ ID NO 17
<211> LENGTH: 25
<212> TYPE: DNA
<213> ORGANISM: Artificial Sequence
<220> FEATURE:
<223> OTHER INFORMATION: primer No. 17

<400> SEQUENCE: 17
tcgggatggg ggaaaaaaac ctctg 25

<210> SEQ ID NO 18
<211> LENGTH: 36
<212> TYPE: DNA
<213> ORGANISM: Artificial Sequence
<220> FEATURE:
<223> OTHER INFORMATION: primer No. 18

<400> SEQUENCE: 18
actctagagg atcccctttc gtaaataaat cagctc 36

<210> SEQ ID NO 19
<211> LENGTH: 1000
<212> TYPE: DNA
<213> ORGANISM: Nannochloropsis oculata

<400> SEQUENCE: 19

```
tcgggatggg ggaaaaaaac ctctgtgtgg gctgtcagtt gatactatta gaggtctttt     60

gttttgtttg tggctgcgtg tgtgtgtttg catgagaaat agacttgaga atatcggaag    120

gaactttgac atggtaaacg aggaaaagaa aatcttcaaa aaggaataat gggtaaaaac    180

aaggagcacc gggtctcttt agaaatgctt ctcggcggaa aaccagaaaa aaaggtagaa    240

tatgtcgact ttttcgctta tcattataga atgaaagatc gaatggccaa gggatttata    300

aattctttct ttatgttgtc gtagaactta ctttccatcc cgagggaggt gtatgcaggc    360

caaaccctct gacatgggcg caatatctct atgaaaggtt gttggaatac attgtccgac    420

ctccttcgag gcggagccgc atagttgaag tataggtgct tgcttcatcc atctcatgac    480

gctttgccag tgactcactc atgcatgtga cacatttagt tctgctcgct caagcctggc    540

ccctcctgac atgcacacat tgcacttgta ggtgggccac gtttagtata gacgccaccc    600

ctgtcgcacc atcggtccca gagcaggagc acgcttccct actcctgtac gctccccctg    660

cttccccccc tgctcgtcaa cgatggcgac gccagcggct gcgaattaca gtgacggcgc    720

ggccgctcag gatgacagct cctctccttc aacatctccc aatcttccac ccccgcccat    780

gtcgtcgttc gtacggccta tgctgaccga tatgtaccaa attacaatgg tcttcgcgta    840

ctggaagcaa aagcggcacc aggacagggc catctttgag ctctttttcc ggaagacacc    900

ctttaaggga gagtttgcca ttatggccgg cattgacgaa gtactcaagt acttggccca    960

ctttcgcttc tccgaggagg agctgattta tttacgaaag                          1000
```

```
<210> SEQ ID NO 20
<211> LENGTH: 20
<212> TYPE: DNA
<213> ORGANISM: Artificial Sequence
<220> FEATURE:
<223> OTHER INFORMATION: primer No. 20

<400> SEQUENCE: 20

gggatcctct agagtcgacc                                                  20


<210> SEQ ID NO 21
<211> LENGTH: 20
<212> TYPE: DNA
<213> ORGANISM: Artificial Sequence
<220> FEATURE:
<223> OTHER INFORMATION: primer No. 21

<400> SEQUENCE: 21

cgggtaccga gctcgaattc                                                  20


<210> SEQ ID NO 22
<211> LENGTH: 35
<212> TYPE: DNA
<213> ORGANISM: Artificial Sequence
<220> FEATURE:
<223> OTHER INFORMATION: primer No. 22

<400> SEQUENCE: 22

cagcccgcat caacaatggt cttccagctc gcccg                                 35


<210> SEQ ID NO 23
<211> LENGTH: 38
<212> TYPE: DNA
<213> ORGANISM: Artificial Sequence
<220> FEATURE:
<223> OTHER INFORMATION: primer No. 23

<400> SEQUENCE: 23
```

ctcttccaca gaagcttagt tgtacttggg gtgattgc 38

<210> SEQ ID NO 24
<211> LENGTH: 35
<212> TYPE: DNA
<213> ORGANISM: Artificial Sequence
<220> FEATURE:
<223> OTHER INFORMATION: primer No. 24

<400> SEQUENCE: 24
cagcccgcat caacaatggg acgcggcggt gagaa 35

<210> SEQ ID NO 25
<211> LENGTH: 35
<212> TYPE: DNA
<213> ORGANISM: Artificial Sequence
<220> FEATURE:
<223> OTHER INFORMATION: primer No. 25

<400> SEQUENCE: 25
ctcttccaca gaagcctatg cccgctgctt gtaga 35

<210> SEQ ID NO 26
<211> LENGTH: 35
<212> TYPE: DNA
<213> ORGANISM: Artificial Sequence
<220> FEATURE:
<223> OTHER INFORMATION: primer No. 26

<400> SEQUENCE: 26
cagcccgcat caacaatggg acgcggtggc gagcg 35

<210> SEQ ID NO 27
<211> LENGTH: 35
<212> TYPE: DNA
<213> ORGANISM: Artificial Sequence
<220> FEATURE:
<223> OTHER INFORMATION: primer No. 27

<400> SEQUENCE: 27
ctcttccaca gaagcttaca tggcggggaa atcgg 35

<210> SEQ ID NO 28
<211> LENGTH: 35
<212> TYPE: DNA
<213> ORGANISM: Artificial Sequence
<220> FEATURE:
<223> OTHER INFORMATION: primer No. 28

<400> SEQUENCE: 28
cagcccgcat caacaatgcc tccccagaac gacgc 35

<210> SEQ ID NO 29
<211> LENGTH: 35
<212> TYPE: DNA
<213> ORGANISM: Artificial Sequence
<220> FEATURE:
<223> OTHER INFORMATION: primer No. 29

<400> SEQUENCE: 29
ctcttccaca gaagcctaac ccatgtgcac ctccg 35

<210> SEQ ID NO 30
<211> LENGTH: 35
<212> TYPE: DNA

<213> ORGANISM: Artificial Sequence
<220> FEATURE:
<223> OTHER INFORMATION: primer No. 30

<400> SEQUENCE: 30
cagcccgcat caacaatggt tgagcaaacg ttacc 35

<210> SEQ ID NO 31
<211> LENGTH: 35
<212> TYPE: DNA
<213> ORGANISM: Artificial Sequence
<220> FEATURE:
<223> OTHER INFORMATION: primer No. 31

<400> SEQUENCE: 31
ctcttccaca gaagcttacg gaggggagga tgaac 35

<210> SEQ ID NO 32
<211> LENGTH: 35
<212> TYPE: DNA
<213> ORGANISM: Artificial Sequence
<220> FEATURE:
<223> OTHER INFORMATION: primer No. 32

<400> SEQUENCE: 32
cgagctcggt acccgttctt ccgcttgttg ctgcc 35

<210> SEQ ID NO 33
<211> LENGTH: 25
<212> TYPE: DNA
<213> ORGANISM: Artificial Sequence
<220> FEATURE:
<223> OTHER INFORMATION: primer No. 33

<400> SEQUENCE: 33
tgttgatgcg ggctgagatt ggtgg 25

<210> SEQ ID NO 34
<211> LENGTH: 21
<212> TYPE: DNA
<213> ORGANISM: Artificial Sequence
<220> FEATURE:
<223> OTHER INFORMATION: primer No. 34

<400> SEQUENCE: 34
gcttctgtgg aagagccagt g 21

<210> SEQ ID NO 35
<211> LENGTH: 28
<212> TYPE: DNA
<213> ORGANISM: Artificial Sequence
<220> FEATURE:
<223> OTHER INFORMATION: primer No. 35

<400> SEQUENCE: 35
ggcaagaaaa gctgggggaa aagacagg 28

<210> SEQ ID NO 36
<211> LENGTH: 800
<212> TYPE: DNA
<213> ORGANISM: Nannochloropsis oculata

<400> SEQUENCE: 36
ttcttccgct tgttgctgcc gatggcggcc atggtctcta agatggagtg gatggaggag 60
gaggcgagcg tagcagcaag cgtgagttat acagccaggc acatgtcgca atccttcggt 120
ctcgggctta aaatccacgc actaatcacg ctgggccatg caaagagcaa tgccgaggcc 180
caccacacaa aacgctgtgt cgcgcgttgc ggcctgaagc ttcatacttc ttagtcgccg 240
ccaaaagggc tcgagagacg agacccgttg gcatgaccga tgttgttcga cgcggtttgc 300
ttcgtcacag tcgacgtgat tcaggaatct ggagcctgca gatcattttt ttcagcctga 360
tatcgttctt ttccactgag aaccatcaga ccaccttttc ttccattgtg tgaaggagta 420
ggagttgccg tgctgctttg tgggagacat ctgcgatggt gaccagcctc ccgtcgtctg 480
gtcgacgtga cgagcctctt cactgttctt cgacggagag acgcaagcga gacggctcta 540
gaccttttgg acacgcattc tgtgtgtgaa ctagtggaca gtgataccac gtctgaaagc 600
tcaccactgc ccatggtgca gctacttgtc acaaagtttt gactccgtcg gtatcaccat 660
tcgcgctcgt gtgcctggtt gttccgccac gccggcctgc cccggggcgg ggcaatattc 720
taaaatctca cgcaaaacac cgcacttacc cctcacacat attcgtgata gaccaccacc 780
aatctcagcc cgcatcaaca 800

<210> SEQ ID NO 37
<211> LENGTH: 613
<212> TYPE: DNA
<213> ORGANISM: Nannochloropsis oculata

<400> SEQUENCE: 37
gcttctgtgg aagagccagt ggtagtagca gtagcagcag cagtagcagc cgcagcactc 60
agtgttggcg cgagagattg tccatccctt cttaacctac cggaagagaa ataaggcctt 120
tctcccgtag ctgtcttcgt ttgtttgtgc tgattgcttg atatgagagt gttgaattcc 180
tgcatcatgt ttttctctgt agtcctttcc tacccccgtc attttctttt ctccctggtt 240
cttcttttgt caccccttatt ttacataaaa ttttctttgt ttatagtgag aggaaggtag 300
agaggggaaa acaagaacaa cgaacgcaag cgtgtgaaag gagggcgagt agaagagaaa 360
cagatctgtt gagcattgag agtggagccg ggggaaaggc ttgtgtgttg tctttgaaaa 420
agttgtttaa atcacgaatc cgttagttct catgtgtacc tctttcacta catgtgatgg 480
agaaaacaaa agtgtgagga ttaattgaag aaaaagaaga gttcgacacg tcaaaccgcc 540
caaaagacgt cacaaagaga acttgattct ctttgccgtg ttgatcctgt cttttccccc 600
agcttttctt gcc 613

<210> SEQ ID NO 38
<211> LENGTH: 35
<212> TYPE: DNA
<213> ORGANISM: Artificial Sequence
<220> FEATURE:
<223> OTHER INFORMATION: primer No. 38

<400> SEQUENCE: 38
ccagcttttc ttgccactgc gcatggattg accga 35

<210> SEQ ID NO 39
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 39
atggtcgaga ttcgaagcat ggacgatgcg ttgcgtgcac tgcggggtcg gtatcccggt 60
tgtgagtggg ttgttgtgga ggatggggcc tcgggggctg gtgtttatcg gcttcggggt 120
ggtgggcggg agttgtttgt caaggtggca gctctggggg ccggggtggg cttgttgggt 180
gaggctgaac ggctggtgtg gttggcggag gtggggattc ccgtacctcg tgttgtggag 240
ggtggtgggg acgagagggt cgcctggttg gtcaccgaag cggttccggg gcgtccggcc 300
agtgcgcggt ggccgcggga gcagcggctg gacgtggcgg tggcgctcgc ggggctcgct 360
cgttcgctgc acgcgctgga ctgggagcgg tgtccgttcg atcgcagtct cgcggtgacg 420
gtgccgcagg cggcccgtgc tgtcgctgaa gggagcgtcg acttggagga tctggacgag 480
gagcggaagg ggtggtcggg ggagcggctt ctcgccgagc tggagcggac tcggcctgcg 540
gacgaggatc tggcggtttg ccacggtgac ctgtgcccgg acaacgtgct gctcgaccct 600
cgtacctgcg aggtgaccgg gctgatcgac gtggggcggg tcggccgtgc ggaccggcac 660
tccgatctcg cgctggtgct gcgcgagctg gcccacgagg aggacccgtg gttcgggccg 720
gagtgttccg cggcgttcct gcgggagtac gggcgcgggt gggatggggc ggtatcggag 780
gaaaagctgg cgttttaccg gctgttggac gagttcttct ga 822

<210> SEQ ID NO 40
<211> LENGTH: 35
<212> TYPE: DNA
<213> ORGANISM: Artificial Sequence
<220> FEATURE:
<223> OTHER INFORMATION: primer No. 40

<400> SEQUENCE: 40 ctttttgtg aagcaatggt cgagattcga agcat 35

<210> SEQ ID NO 41
<211> LENGTH: 35
<212> TYPE: DNA
<213> ORGANISM: Artificial Sequence
<220> FEATURE:
<223> OTHER INFORMATION: primer No. 41

<400> SEQUENCE: 41
tttcccccat cccgatcaga agaactcgtc caaca 35

<210> SEQ ID NO 42
<211> LENGTH: 999
<212> TYPE: DNA
<213> ORGANISM: Artificial Sequence
<220> FEATURE:
<223> OTHER INFORMATION: Hygromycin resistance gene

<400> SEQUENCE: 42
atgacacaag aatccctgtt acttctcgac cgtattgatt cggatgattc ctacgcgagc 60
ctgcggaacg accaggaatt ctgggagccg ctggcccgcc gagccctgga ggagctcggg 120
ctgccggtgc cgccggtgct gcgggtgccc ggcgagagca ccaaccccgt actggtcggc 180
gagcccggcc cggtgatcaa gctgttcggc gagcactggt gcggtccgga gagcctcgcg 240
tcggagtcgg aggcgtacgc ggtcctggcg gacgccccgg tgccggtgcc ccgcctcctc 300
ggccgcggcg agctgcggcc cggcaccgga gcctggccgt ggccctacct ggtgatgagc 360
cggatgaccg gcaccacctg gcggtccgcg atggacggca cgaccgaccg gaacgcgctg 420
ctcgccctgg cccgcgaact cggccgggtg ctcggccggc tgcacagggt gccgctgacc 480
gggaacaccg tgctcacccc ccattccgag gtcttcccgg aactgctgcg ggaacgccgc 540
gcggcgaccg tcgaggacca ccgcgggtgg ggctacctct cgccccggct gctggaccgc 600

```
ctggaggact ggctgccgga cgtggacacg ctgctggccg gccgcgaacc ccggttcgtc    660

cacggcgacc tgcacgggac caacatcttc gtggacctgg ccgcgaccga ggtcaccggg    720

atcgtcgact tcaccgacgt ctatgcggga gactcccgct acagcctggt gcaactgcat    780

ctcaacgcct tccggggcga ccgcgagatc ctggccgcgc tgctcgacgg ggcgcagtgg    840

aagcggaccg aggacttcgc ccgcgaactg ctcgccttca ccttcctgca cgacttcgag    900

gtgttcgagg agaccccgct ggatctctcc ggcttcaccg atccggagga actggcgcag    960

ttcctctggg ggccgccgga caccgccccc ggcgcctga                           999


<210> SEQ ID NO 43
<211> LENGTH: 37
<212> TYPE: DNA
<213> ORGANISM: Artificial Sequence
<220> FEATURE:
<223> OTHER INFORMATION: primer No. 43

<400> SEQUENCE: 43

ctttttgtg aagcaatgac acaagaatcc ctgttac                               37


<210> SEQ ID NO 44
<211> LENGTH: 36
<212> TYPE: DNA
<213> ORGANISM: Artificial Sequence
<220> FEATURE:
<223> OTHER INFORMATION: primer No. 44

<400> SEQUENCE: 44

tttcccccat cccgatcagg cgccgggggc ggtgtc                               36


<210> SEQ ID NO 45
<211> LENGTH: 452
<212> TYPE: PRT
<213> ORGANISM: Nannochloropsis gaditana

<400> SEQUENCE: 45

Met Gly Arg Gly Gly Glu Lys Thr Val Thr Pro Pro Ser Lys Ser Phe
1               5                   10                  15

His Ala His Gly His Ser Leu Thr Ala Ser Asp Leu Ser Arg Ala Asp
            20                  25                  30

Ala Ala Ser Thr Ile Ser Ser Ser Val Arg Pro Ser Lys Ser Leu Glu
        35                  40                  45

Ala Met Pro Thr Glu Glu Leu Arg Lys Lys Ala Leu Gln Tyr Gly His
    50                  55                  60

Asp Ala Ser Ala Asp Arg Ala Ser Leu Leu Gln Ile Leu Ala Pro Tyr
65                  70                  75                  80

Gly Asp Ile Leu Leu Arg Thr Asp Ala Pro Pro Ser Leu Pro Leu Ala
                85                  90                  95

Pro Pro Pro Phe Thr Leu Ala Asp Ile Lys Ala Ala Val Pro Arg His
            100                 105                 110

Cys Phe Glu Arg Ser Leu Thr Thr Ser Phe Phe His Leu Ala Cys Asp
        115                 120                 125

Leu Val Leu Val Ala Leu Leu Gly Tyr Leu Ala Thr Leu Ile Gly His
    130                 135                 140

Pro Asp Val Pro Thr Met Ser Arg Tyr Leu Leu Trp Pro Leu Tyr Trp
145                 150                 155                 160

Tyr Ala Gln Gly Ser Val Leu Thr Gly Val Trp Val Ile Ala His Glu
                165                 170                 175
```

```
Cys Gly His Gln Ser Phe Ser Pro Tyr Glu Arg Val Asn Asn Leu Val
            180                 185                 190

Gly Trp Val Leu His Ser Ala Leu Leu Val Pro Tyr His Ser Trp Arg
        195                 200                 205

Ile Ser His Gly Lys His His Asn Asn Thr Gly Ser Cys Glu Asn Asp
    210                 215                 220

Glu Val Phe Ala Pro Pro Ile Lys Glu Asp Leu Met Asp Glu Ile Leu
225                 230                 235                 240

Leu His Ser Pro Leu Ala Asn Leu Ala Gln Ile Ile Ile Met Leu Thr
                245                 250                 255

Val Gly Trp Met Pro Gly Tyr Leu Leu Met Asn Ala Thr Gly Pro Arg
            260                 265                 270

Lys Tyr Lys Gly Lys Asn Asn Ser His Phe Asp Pro Asn Ser Ala Leu
        275                 280                 285

Phe Ser Pro Lys Asp Arg Leu Asp Ile Ile Trp Ser Asp Ile Gly Phe
    290                 295                 300

Phe Leu Ala Leu Ala Gly Val Val Trp Ala Cys Thr Gln Tyr Gly Phe
305                 310                 315                 320

Ser Thr Val Gly Lys Tyr Tyr Leu Leu Pro Tyr Met Val Val Asn Tyr
                325                 330                 335

His Leu Val Leu Ile Thr Tyr Leu Gln His Thr Asp Val Phe Ile Pro
            340                 345                 350

His Phe Arg Gly Ala Glu Trp Ser Trp Phe Arg Gly Ala Leu Cys Thr
        355                 360                 365

Val Asp Arg Ser Phe Gly Trp Leu Leu Asp His Thr Phe His His Ile
    370                 375                 380

Ser Asp Thr His Val Cys His His Ile Phe Ser Lys Met Pro Phe Tyr
385                 390                 395                 400

His Ala Gln Glu Ala Ser Glu His Ile Lys Lys Ala Leu Gly Pro Tyr
                405                 410                 415

Tyr Leu Lys Asp Asp Thr Pro Ile Trp Lys Ala Leu Trp Arg Ser Tyr
            420                 425                 430

Thr Leu Cys Lys Tyr Val Asp Thr Asp Lys Asn Ala Val Phe Tyr Lys
        435                 440                 445

His Arg Ala Ser
    450
```

<210> SEQ ID NO 46
<211> LENGTH: 1359
<212> TYPE: DNA
<213> ORGANISM: Nannochloropsis gaditana

<400> SEQUENCE: 46

```
atggggcgtg gcggtgagaa aactgtcaca cctccatcaa aatccttcca tgctcatggc     60

cactctctga ccgccagtga cctttctcga gcggatgccg catccactat ctcgagctcg    120

gttaggccca gtaagtcgtt ggaggcaatg cccacggaag aattgcgaaa gaaggcactg    180

caatacggac acgacgcctc cgcggacagg gcctcgttgc ttcaaatact ggccccatat    240

ggcgacattc ttcttcgtac ggacgcgcct ccctccctcc ccctcgcccc tcctcccttc    300

acccttgcgg atatcaaagc cgccgtaccc aggcattgct tcgaacgctc cttgaccacc    360

tccttcttcc acctcgcttg tgacctcgtc ctggttgctc tgctcggata cttggccacg    420

ctcatcgggc acccggacgt gccgaccatg tcccgctacc tactgtggcc tctctactgg    480
```

```
tacgcgcagg gctcggtgct gacaggcgtg tgggtcattg cccatgaatg tgggcatcag    540

tctttttccc cgtacgaacg ggtgaacaac ctggtggggt gggtcctgca ctccgccctc    600

ctcgtcccgt accattcctg gcgcatctcc cacggcaagc accacaacaa cacggggagc    660

tgcgagaacg acgaggtgtt cgcgccgcca atcaaggaag acctgatgga cgagatcctc    720

ctccactccc ccttggccaa cctcgcccaa atcatcatca tgttgaccgt gggatggatg    780

cccggctacc tgttgatgaa tgccacggga cctcgaaagt acaagggcaa gaacaacagc    840

cacttcgatc cgaattcggc gctgttctcc cccaaggacc gcttggatat catctggtcg    900

gacataggct tcttcctcgc tttggccggc gtggtgtggg cctgcaccca gtacgggttc    960

tccacggtgg gcaagtacta cctgctcccc tacatggtgg tgaactatca cctggtgctc   1020

atcacctatc tccagcacac ggacgtcttc atccctcatt tccgcggggc agagtggtca   1080

tggttccggg ggctctttg cactgtcgac cgctccttcg gctggctgct cgaccatacg   1140

ttccaccaca tctcggacac gcacgtctgc catcatatct ttagtaagat gcctttctat   1200

cacgcgcaag aagcgagtga gcacatcaag aaggcgctgg ggccgtacta cctgaaggac   1260

gacaccccga tatggaaagc gttgtggcga agttatacgc tttgcaagta tgtggacacg   1320

gataaaaatg ccgtttttta caagcaccga gcatcatag                           1359


<210> SEQ ID NO 47
<211> LENGTH: 475
<212> TYPE: PRT
<213> ORGANISM: Nannochloropsis gaditana

<400> SEQUENCE: 47

Met Gly Arg Gly Gly Glu Arg Val Glu Thr Gln Glu Ser Ile Ala Thr
1               5                   10                  15

Tyr Ser Ala Ser Lys Ser Gly Asp Ile Arg Gln His Gly Gly Lys Ile
            20                  25                  30

Thr Trp Asp Glu Val Arg Gln His Lys Thr Pro Gln Asp Ala Trp Leu
        35                  40                  45

Val Tyr Arg Asn Lys Val Tyr Asp Val Ser Gly Trp Gln Asp His Pro
    50                  55                  60

Gly Gly Asn Val Ile Phe Thr His Ala Gly Gly Asp Cys Thr Asp Ile
65                  70                  75                  80

Phe Ala Ala Phe His Pro Leu Gly Ala Thr Ser Tyr Met Asp Pro Phe
                85                  90                  95

Tyr Ile Gly Glu Leu Val Pro Gly Ser Asp Lys Lys Pro Glu Ala Gln
            100                 105                 110

Ala Ser Phe Glu Arg Ala Tyr Arg Asp Leu Arg Gly Lys Leu Ile Thr
        115                 120                 125

Gly Gly Phe Phe Lys Ala Ser Pro Leu Tyr Tyr Val Trp Lys Val Val
    130                 135                 140

Ser Thr Val Ala Leu Ala Val Gly Ala Trp Met Leu Val Gly Trp Ser
145                 150                 155                 160

Gln Ala Leu Ser Ile Gln Met Leu Ser Ala Phe Ile Leu Ala Leu Phe
                165                 170                 175

Trp Gln Gln Cys Gly Trp Leu Ala His Asp Phe Leu His His Gln Val
            180                 185                 190

Phe Lys Glu Arg Ala Tyr Gly Asp Leu Ala Gly Ile Met Ile Gly Asn
        195                 200                 205

Val Phe Gln Gly Phe Ser Val Ala Trp Trp Lys Asn Lys His Asn Thr
    210                 215                 220
```

```
His His Ala Val Pro Asn Leu Val Glu Ser Ser Pro Asp Ala Gln Asp
225                 230                 235                 240

Gly Asp Pro Asp Ile Asp Thr Met Pro Ile Leu Ala Trp Ser Leu Lys
                245                 250                 255

Met Ala Asp Arg Ala Lys Glu Tyr Ser Trp Gly Pro Phe Phe Leu Arg
            260                 265                 270

His Gln Ala Phe Leu Tyr Phe Pro Ile Leu Leu Val Ala Arg Ile Ser
        275                 280                 285

Trp Leu Leu Gln Ser Phe Leu Phe Val Phe Glu His Val Pro Gly Ala
    290                 295                 300

Ser Leu Trp Ala Thr Lys Gly Ala Thr Thr Glu Arg Gln Ala Ile Lys
305                 310                 315                 320

Asn Val Gly Leu Glu Lys Ala Gly Leu Leu Leu Tyr Tyr Leu Trp Tyr
                325                 330                 335

Gly Ala Leu Met Phe Cys Asn Met Ser Leu Thr Arg Val Leu Ile Tyr
            340                 345                 350

Phe Val Ala Ser Gln Met Met Cys Gly Phe Leu Leu Ala Leu Val Phe
        355                 360                 365

Gly Leu Gly His Asn Gly Met Ala Val Tyr Asp Ala Asp Ala Arg Pro
    370                 375                 380

Asp Phe Trp Lys Leu Gln Val Thr Thr Thr Arg Asn Val Thr Gly Gly
385                 390                 395                 400

Trp Leu Ile Gln Trp Phe Cys Gly Gly Leu Gly Tyr Gln Val Asp His
                405                 410                 415

His Leu Phe Pro Met Ile Pro Arg His Arg Leu Gly Gln Leu His Gly
            420                 425                 430

Leu Val Glu Ser Phe Cys Lys Glu His Gly Val Lys Tyr His Glu Thr
        435                 440                 445

Ser Met Trp Glu Gly Thr Arg Glu Val Leu Ala His Leu Ala Ser Val
    450                 455                 460

Thr Lys Glu Phe Val Thr Asp Phe Pro Ala Met
465                 470                 475
```

<210> SEQ ID NO 48
<211> LENGTH: 1428
<212> TYPE: DNA
<213> ORGANISM: Nannochloropsis gaditana

<400> SEQUENCE: 48

```
atgggacgcg gtggtgaaag agtggagacg caagagtcta tagctactta ctcggcaagc      60

aaaagtggtg acatcaggca gcatgggggt aaaattactt gggatgaggt gcgtcaacac     120

aagacccctc aagatgcgtg gctcgtctac cgcaacaaag tctacgacgt gtcaggctgg     180

caagatcatc ctgggggggaa tgtcatcttt acgcatgcgg ggggtgactg tactgacatc     240

tttgcagcct tccacccttt gggtgcgaca tcttacatgg atcccttcta cattggcgag     300

ctcgttcccg gctctgacaa aaagcccgag gcgcaagcca gcttcgagcg agcgtatcga     360

gacttgaggg ggaaactcat cacgggcggg ttcttcaagg cgagtccttt gtactatgtg     420

tggaaagtcg tgtccaccgt cgccctggcc gtgggtgcct ggatgctcgt cggctggtcc     480

caagccctgt cgattcagat gctctctgcc ttcatcctcg ccctcttctg gcagcagtgc     540

gggtggctgg cccatgactt cttgcaccat caagttttca aagagcgagc atacggcgat     600

ctcgcgggga tcatgatcgg caatgtattc cagggcttct cggtggcctg gtggaagaac     660
```

```
aagcacaaca ctcatcacgc cgtgcccaac cttgtcgagt cctctccaga cgcccaggac    720

ggtgatcccg acattgacac catgcccatc ctggcctggt ccctgaagat ggcggaccgc    780

gcaaaggaat actcgtgggg ccctttcttc ctccggcatc aggctttcct ctactttccc    840

atcctccttg tcgcccgcat ctcctggctc ttgcaatcct tcctttttgt cttcgaacac    900

gtccccggtg caagcttatg ggctacgaaa ggcgcaacga ccgagcgaca ggccataaag    960

aacgtgggac tagagaaagc ggggcttctc ctttactatt tgtggtacgg cgctctcatg   1020

ttctgcaaca tgtctcttac gcgggtcctg atctacttcg tggcttctca gatgatgtgc   1080

ggctttctct tggccctcgt cttcggcctc ggccacaacg gcatggcggt ctacgacgcc   1140

gacgcccgcc cggacttctg gaaactgcaa gtgacgacca cgagaaatgt gacggggggc   1200

tggttgatac aatggttctg tggcggtctt ggctaccaag tagaccacca cctttttcca   1260

atgattccgc gccaccgtct tggtcagtta cacggtttgg tggaatcttt ctgcaaggag   1320

catggggtaa agtatcacga gacaagtatg tgggaaggga cacgggaggt gttggcccac   1380

ttggcgagcg tgacaaaaga attcgtaaca gatttcccag caatgtag                1428
```

<210> SEQ ID NO 49
<211> LENGTH: 407
<212> TYPE: PRT
<213> ORGANISM: Nannochloropsis gaditana

<400> SEQUENCE: 49

```
Met Val Glu Gln Thr Leu Pro Thr Leu Ser Gln Leu Lys Lys Ala Ile
1               5                   10                  15

Pro Glu Lys Cys Phe Gln Lys Ser Leu Leu Arg Ser Val Tyr Tyr Met
            20                  25                  30

Leu Arg Asp Phe Ala Ala Leu Ala Ala Leu Tyr Ile Ile Tyr Pro Ser
        35                  40                  45

Val Gln Ala Asn Phe Gly Leu Ala Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Phe Asn Asp Val Cys Gly His
                85                  90                  95

Ile Cys His Ala Pro Leu Met Val Pro Tyr Trp Pro Trp Gln Lys Ser
            100                 105                 110

His Arg Leu His His Met Tyr His Asn His Leu Thr Lys Asp Met Ser
        115                 120                 125

His Pro Trp Met Thr Gln Glu Ile Phe Glu Asp Leu Thr Pro Phe Glu
    130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Leu Asp Gly Ser His Val Leu Pro Thr
                165                 170                 175

Ser Pro Leu Phe Ser Asp Thr Lys Glu Arg Ile Gln Cys Ala Val Ser
            180                 185                 190

Thr Leu Cys Met Leu Val Ala Gly Val Leu Ile Tyr Val Gly Leu Glu
        195                 200                 205

Gly Gly Ala Glu Gly Gly Leu Ala Arg Ile Gly Ser Met Tyr Leu Ile
    210                 215                 220

Pro Leu Leu Val Phe Asn Ala Trp Ile Thr Met Val Thr Tyr Leu Gln
225                 230                 235                 240
```

-continued

```
His His Asp Glu Asp Thr Lys Val Tyr Ala Glu Gly Glu Trp Ser Tyr
                245                 250                 255

Ile Lys Gly Ala Leu Glu Thr Ile Asp Arg Glu Tyr Gly Met Gly Ile
            260                 265                 270

Asp Asp Leu Ser His Asn Ile Thr Asp Gly His Val Ala His His Leu
        275                 280                 285

Phe Phe Thr Gln Ile Pro His Tyr His Leu Lys Asp Ala Thr Ala Ala
    290                 295                 300

Val Arg Gln Leu Leu Thr Pro Thr Gly Thr Tyr Lys Lys Lys Gln Ser
305                 310                 315                 320

Trp Asn Phe Leu Gly Lys Phe Thr Glu Leu Asn Tyr Lys Leu Lys Tyr
                325                 330                 335

Val Ala Gly Gln Gly Val Leu Ser Tyr Val Asp Trp Glu Ala Ile Gln
            340                 345                 350

Lys Gly Ala Ser Pro Pro Val Cys Ser Thr Asp Ala Ser Pro Ala Thr
        355                 360                 365

Pro Ala Ala Pro Leu Pro Lys Val Ala Val Thr Cys Ala Thr Glu Pro
    370                 375                 380

Leu Ile Ala Leu Glu Ala Lys Gly Arg Ser Thr Arg Lys Arg Ser Pro
385                 390                 395                 400

Ala Arg Ser Ser Ser Pro Pro
                405
```

<210> SEQ ID NO 50
<211> LENGTH: 1224
<212> TYPE: DNA
<213> ORGANISM: Nannochloropsis gaditana

<400> SEQUENCE: 50

```
atggttgagc aaacgctacc gacactttct caattgaaga aagccattcc cgagaaatgc      60

ttccagaaat cacttctccg ctctgtgtac tacatgctgc gagactttgc cgccctggca     120

gctctgtata ttatataccc cagcgtgcag gctaattttg gccttgccgg actctttgtg     180

tggtggaacc tggcgggatt ttttatgtgg tgtctctttg tgatcggtca cgactgtggt     240

cacggctcct tctcggagta taagtggttc aacgacgtct gtggccatat ttgccacgcc     300

ccgctcatgg tgccctactg gccctggcag aagtcccatc gcctgcacca catgtaccac     360

aaccacctga cgaaagacat gtcacatcca tggatgacgc aagagatctt cgaggaccta     420

acaccgttcg agcaagcctt gctggagaac ccactctccc tcttcatcaa atacacattc     480

ctctacctct tcgcgggcaa actcgacggc agccacgtcc tgcccacctc ccccctcttc     540

agcgatacca aggagcgcat ccagtgcgcc gtctccaccc tctgcatgct cgtggccggg     600

gtcctcattt atgtgggcct tgaaggaggg gcggagggag ggctggctcg gatcggctcc     660

atgtatttga tcccgctgtt ggtgttcaac gcctggatca ccatggtcac gtacctgcag     720

catcacgacg aggacacgaa ggtgtacgcg gagggggagt ggagctacat caagggggcg     780

ctcgagacca tcgatcggga gtatgggatg ggcattgatg acctgtcgca caacatcacg     840

gacggccacg tcgcccacca cctcttcttc acccagatcc cgcactacca cctgaaggac     900

gctacggccg ccgtacggca gctcttgacg cccacgggca cctacaagaa gaagcaatcc     960

tggaattttc tgggaaaatt cactgagttg aactacaagt tgaagtatgt tgcgggacaa    1020

ggggtgctct cctacgtgga ctgggaggct attcagaagg gtgcttcccc cccggtttgt    1080

tccaccgacg cctcccctgc cactcccgca gcgcccctac ctaaggtggc tgtcacctgc    1140
```

```
gcgacagaac cgttaatcgc ccttgaagcg aagggaagat caacccgaaa gcgctctccg   1200

gcacgctcct cttcacctcc gtag                                          1224


<210> SEQ ID NO 51
<211> LENGTH: 515
<212> TYPE: PRT
<213> ORGANISM: Nannochloropsis gaditana

<400> SEQUENCE: 51

Met Pro Pro Gln Asn Asp Ala Ala Leu Gly Ser Gly Leu Phe Arg Asn
1               5                   10                  15

Arg Phe Gly Arg Lys Ser Ser Ala Ser Ser Leu Leu Val Asn Asp Gly
            20                  25                  30

Ser Met Gly Ser Thr Glu Pro Val Leu Ser Thr Ala Ala Val Pro Ala
        35                  40                  45

Thr Glu Pro Ala Gly Lys Ser Tyr Thr Trp Gln Glu Val Ala Glu His
    50                  55                  60

Asn Thr Glu Lys Ser Leu Trp Val Thr Val Arg Gly Lys Val Tyr Asp
65                  70                  75                  80

Ile Ser Ser Trp Val Asp Asn His Pro Gly Gly Lys Glu Ile Leu Leu
                85                  90                  95

Leu Ala Ala Gly Arg Asp Ile Thr Tyr Ala Phe Asp Ser Tyr His Pro
            100                 105                 110

Phe Thr Glu Lys Pro Thr Gln Val Leu Asn Lys Phe Glu Ile Gly Arg
        115                 120                 125

Val Thr Ser Tyr Glu Phe Pro Gln Tyr Lys Ala Asp Thr Arg Gly Phe
    130                 135                 140

Tyr Lys Ala Leu Cys Thr Arg Val Asn Asp Tyr Phe Val Ala His Lys
145                 150                 155                 160

Leu Asn Pro Lys Asp Pro Ile Pro Gly Ile Trp Arg Met Cys Leu Val
                165                 170                 175

Ala Leu Val Ala Leu Ala Ser Phe Val Val Cys Asn Gly Tyr Val Gly
            180                 185                 190

Val Glu Gly Thr Trp Ala Gly Thr Thr Trp Ala Arg Leu Val Ala Ala
        195                 200                 205

Val Val Phe Gly Ile Cys Gln Ala Leu Pro Leu Leu His Val Met His
    210                 215                 220

Asp Ser Ser His Leu Ala Phe Gly Asn Thr Glu Arg Trp Trp Gln Val
225                 230                 235                 240

Gly Gly Arg Leu Ala Met Asp Phe Phe Ala Gly Ala Asn Met Thr Ser
                245                 250                 255

Trp His Asn Gln His Val Ile Gly His His Ile Tyr Thr Asn Val Phe
            260                 265                 270

Leu Ala Asp Pro Asp Leu Pro Asp Lys Ala Ala Gly Asp Pro Arg Arg
        275                 280                 285

Leu Val Gln Lys Gln Ala Trp Gln Ala Met Tyr Lys Trp Gln His Leu
    290                 295                 300

Tyr Leu Pro Pro Leu Tyr Gly Ile Leu Gly Ile Lys Phe Arg Val Gln
305                 310                 315                 320

Asp Ile Met Glu Thr Phe Gly Ser Gly Thr Asn Gly Pro Val Arg Val
                325                 330                 335

Asn Pro Leu Ser Phe Phe Gln Trp Ala Glu Met Ile Phe Thr Lys Met
            340                 345                 350

Phe Trp Ala Gly Trp Arg Ile Ala Phe Pro Leu Leu Ser Pro Ser Phe
```

```
        355                 360                 365

His Thr Gly Trp Ala Ala Phe Ser Ala Leu Phe Leu Val Ser Glu Phe
    370                 375                 380

Met Thr Gly Tyr Phe Leu Ala Phe Asn Phe Gln Val Ser His Val Ser
385                 390                 395                 400

Ser Glu Cys Asp Tyr Pro Leu Gly Glu Ala Pro Arg Glu Gly Glu Asp
                405                 410                 415

Gly Asn Ile Val Asp Glu Trp Ala Val Ser Gln Ile Lys Ser Ser Val
            420                 425                 430

Asp Tyr Ala His Asn Asn Pro Val Thr Thr Phe Leu Cys Gly Ala Leu
        435                 440                 445

Asn Tyr Gln Val Thr His His Leu Phe Pro Thr Val Ser Gln Tyr His
    450                 455                 460

Tyr Pro Ala Ile Ala Pro Ile Ile Gln Asp Val Cys Arg Glu Phe Asn
465                 470                 475                 480

Val Asp Tyr Lys Val Leu Pro Asp Phe Val Thr Ala Phe His Ala His
                485                 490                 495

Ile Ala His Leu Lys Thr Leu Gly Glu Arg Gly Glu Ala Ala Glu Val
            500                 505                 510

His Met Gly
        515


<210> SEQ ID NO 52
<211> LENGTH: 1548
<212> TYPE: DNA
<213> ORGANISM: Nannochloropsis gaditana

<400> SEQUENCE: 52

atgcctccgc agaacgacgc tgccctcgga agtggtctct ttcggaaccg cttcggtcgc      60

aaaagctccg cttcttccct tcttgtcaat gacggcagta tgggaagcac cgagcctgtc     120

ctttccacgg cggccgtacc ggcaacggag ccggcgggga aatcctacac atggcaagaa     180

gtagccgagc acaacacaga gaaaagtttg tgggtcactg tgcgagggaa ggtgtacgac     240

atatccagtt gggtggacaa ccatccgggg ggcaaggaga tcctgctgtt ggcggcgggg     300

agggacatca cgtacgcctt cgattcctac cacccgttca cggagaaacc gacgcaggtg     360

ctcaacaagt ttgagatcgg ccgggtcacc tcctacgaat tcccccagta caaggcggac     420

actcgtggtt tctacaaggc cctgtgcacc cgcgtgaatg actactttgt ggcccacaag     480

ctcaacccta aggacccaat ccccggcatc tggcgcatgt gcctcgtcgc cctggtggcc     540

ttggcctctt tcgtggtctg caacggctac gtgggtgtgg aagggacatg ggccgggact     600

acgtgggccc ggctagtggc ggcggtggtg tttgggatct gtcaggccct tcctttgttg     660

cacgtcatgc acgactcctc ccacctggcg tttggcaata cagaacgctg gtggcaggtg     720

ggggggcggc tggcgatgga tttcttcgcc ggggcgaaca tgaccagctg gcacaaccaa     780

cacgtgatcg gccaccatat ctacacgaat gtcttcctcg ccgacccgga tttacccgac     840

aaagccgcgg gagatccgag aagattggtg cagaaacagg cgtggcaagc catgtataaa     900

tggcagcact tgtaccttcc ccctctgtac ggcatcctgg ggatcaaatt tcgagtccaa     960

gatatcatgg agaccttcgg aagtggcacg aacgggcccg tacgggtgaa ccccttgtcc    1020

tttttccaat gggccgagat gattttcacc aaaatgtttt gggcaggatg gaggatcgcg    1080

ttccccttgc tctccccgtc tttccacacc ggctgggctg ctttttccgc cctcttcctg    1140

gtcagcgagt ttatgaccgg gtacttcctc gcctttaatt tccaagtctc ccacgtctcc    1200
```

```
tccgaatgcg actacccctt gggcgaagcc ccccgagagg gagaggatgg caacatcgtg   1260

gacgaatggg cggtctccca aataaagagc agtgtggact atgcgcacaa caacccagta   1320

accaccttcc tctgcggcgc cctgaactac caagtcactc accatctgtt ccccactgtg   1380

agtcaatacc actacccagc catcgcgccc atcatccaag acgtgtgtcg ggagttcaat   1440

gtggattaca aggttctgcc ggattttgtg acggctttcc acgcccacat agcgcatctg   1500

aagacgttgg gggagcgggg ggaggcagca gaagttcaca tgggctaa                1548
```

<210> SEQ ID NO 53
<211> LENGTH: 340
<212> TYPE: PRT
<213> ORGANISM: Nannochloropsis gaditana

<400> SEQUENCE: 53

```
Met Val Phe Gln Leu Ala Arg Asp Ala Leu Ser Ala Leu Val Tyr His
1               5                   10                  15

Tyr Lys Glu Gly Asn Leu Asn Trp Pro Met Ile Ile Tyr Leu Val Leu
            20                  25                  30

Ala His Leu Ala Ala Tyr Met Gly Leu Val Ser Ile Pro Ser Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Thr
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Arg Tyr Phe Trp Gly Glu Ala
            180                 185                 190

Phe Trp Asn Ala Phe Trp Val Ala Gly Gly Leu Arg Tyr Cys Leu Val
        195                 200                 205

Leu His Phe Thr Trp Met Val Asn Ser Ala Ala His Leu Tyr Gly Asp
    210                 215                 220

His Pro Tyr Asp Pro Thr Ile Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Arg Gln Phe Asn Pro
            260                 265                 270

Thr Lys Ala Phe Ile Asp Phe Phe Ala Ala Ile Gly Met Val Ser Asn
        275                 280                 285

Arg Lys Arg Ala Thr Gly Ala Trp Ala Lys Leu Arg Glu Ser Arg Ala
    290                 295                 300

Lys Asp Glu Ala Asn Gly Lys Ser Ile Lys Asp Phe Arg Gly Arg Gly
```

-continued

```
305                 310                 315                 320

Val Val Gln Gly Thr Ala Gln Pro Pro Gly Trp Glu Gln Ser Ala His
                325                 330                 335

Pro Lys Tyr Asn
            340
```

<210> SEQ ID NO 54
<211> LENGTH: 1023
<212> TYPE: DNA
<213> ORGANISM: Nannochloropsis gaditana

<400> SEQUENCE: 54

```
atggtcttcc agttggctcg cgatgccttg tcggcgcttg tctaccacta caaagagggc     60

aacctgaatt ggcccatgat catctaccta gtcctcgcgc accttgccgc ctacatgggg    120

ctggtctcca tcccttcatg caagtggcag acccttctgg aggccttcat cctgtggccc    180

atcaccgggt tgggcatcac ggccggcgtc catcgtctgt gggcgcatcg ctcctacact    240

gccaccttgc cgtaccgcat cctcctcatg ctcttcaatt cgattgcgaa tcaaggcagc    300

atctaccact ggtcccggga tcatcgcgtt caccacaagt actcggagac agatgcggat    360

cctcacaatg ccacccgtgg cttcttcttc gcgcacatgg ggtggcttat cgttaagaaa    420

cacccgaagg tagtagaagg cggcaaacag ttggatttct ctgatcttgc tgcggacccg    480

gtggtccgtt tccagcgtga ctgggacccg tggttcgcgc aattcatgtg cttcgtcatg    540

ccggcgctgg tcgccagata tttctggggt gaggcctttt ggaacgcatt ttgggttgca    600

gggggcctcc gctactgtct ggtcctgcat ttcacctgga tggtgaactc cgccgcccac    660

ttatacggcg atcaccccta cgacccccacc atctggcccg ccgagaaccc gctagtatcg    720

gtggtggcca tcggggaggg atggcacaat tggcatcacc ggtatcccta cgactatgcg    780

gcatctgagt tcgggatctc ccgacaattt aaccctacga aggctttcat tgacttcttt    840

gctgccatcg gtatggtctc gaatcgaaag cgggcgacag gggcctgggc caagctcagg    900

gagtcacggg cgaaggacga ggcgaacggg aagagcatca aagatttcg aggacgagga      960

gttgtccaag gcaccgcaca gccaccggga tgggaacaaa gcgcgcaccc caagtacaac   1020

tga                                                                 1023
```

<210> SEQ ID NO 55
<211> LENGTH: 1000
<212> TYPE: DNA
<213> ORGANISM: Nannochloropsis oculata

<400> SEQUENCE: 55

```
tctctcactc acctccactc tcacacgcca cgtacccgtg cttggttgct atatagattg     60

ctaggttgca cacggcaccg gtgcctgggc tggtatactt gctcgatccg ctggtgcccg    120

cggcctcctc aatgcccccct ccaaaaagct ggcattcgtt agcacacaga tcttccggca   180

ccatgtgaac aaatgatgct tatggaatga aaagcaattt gtcgtttctg aatgcgaaag    240

ccaaccaata ggtgcttagg tgctcgcgtc gatcgtgtaa atgatgtggc gcatgatgga    300

gcatgacacg ctttcatcgc atcgcaaaat atcatttttg tccaggactt gtgtcataca    360

taaaagagct tgaatcgacg atcggaaaaa gcgacagctg gcggtgccag caaggcaact    420

ggcgtgtgat gatgcgcctg ccgttggaaa gggaaaggcg aagcgcagcc gtccaatcca    480

tgtccaatag acacgaccac agtggaaagc ctctctctta gaccgtcaca atacttttgg    540

ccaaggcttc ggcagttcaa ctgccaagca ggcaaaagtc aagggcaacc acatgatgct    600
```

```
gggaggaatg ttagcaggaa cccggagctt gtgtcgttgt tcttcctcgt cagccgggat    660

tgctcgccag cgcgaccaca ccagcccccc acttcttctt gttgtgactt gcgcaagcat    720

ttaacctctt atcgcgcact gtaatttgcc ggccacgcct gtggcgttca caaccccatc    780

ctgctgctga cggggatttg atgcctacca gggtctgaac gcccgcttat tagagaagcc    840

acgtaagcat accatcacag atcgccttct tgccgcggca tgtcccaatc aaatgaagtc    900

agatggattg gttcctcatg cccaccgaca gctcagcctc tcatacgccc tctacactcc    960

tcacatcaca gactcccttc ccacccatcc gagccaaacc                         1000
```

<210> SEQ ID NO 56
<211> LENGTH: 1000
<212> TYPE: DNA
<213> ORGANISM: Nannochloropsis oculata

<400> SEQUENCE: 56

```
gaatcgctat gaccaaaggg ggggaggttg tttggctgcg cgccgttgta gcggcgccag      60

acgctagatg atgtcgtgga tggggcagta attataatgg agaaatacac caaccaattg    120

ccacggtact tccgacgtga aagtaggcga cttgcggcat tcgcgccgta gtgttgccct    180

ttgcccccgt gtcccagtcc ctgcctggct ctctctctca ctgtgtttct cgtgcctccc    240

gaggccagtc caaacctcca gcgtgacgag acaacggcta ggatttcgcg tcgccgagag    300

agcaacgcag cactttccgt ctgatccatc caagaacaac ggccgtggcg cgtcgacaaa    360

cttaggcaat tatattctta aatcctggca aaagcatgta agcgtgaccg gaacactctt    420

gcttgggtcg tggttgaggc ttggccgcgt aaatcacccc cggagcgaca acatcgccgc    480

cccgagtgct gagctggcca cggaggcaag aggcgaggtg gaacaatata cagatgaatt    540

atgaacattt cgtggcctta ttgatgcctg tagtctcgca aatcgctgcc ttgttctcat    600

tttcgatgtt tcttcagtga cgagctacag cgggaatggt gatggctgtg tcacttggga    660

gtgcagcgtc gtcgggtttt gcgccgaccg gctgaggcat gttgcctgcg tcggcttgcg    720

gtcctagatc gcggcgacca caccacctcg aaagcgcgtt cacgaagaca tggcttgtat    780

tggtactacg gcagcatacg cattatgttc atctgctgca cgcaaagcca gcttctctca    840

cacttgctgt ccacctgacc ttggctctgt caaaccacca cctacttggg gcctaactca    900

cccatccctc cactccaact ccacattcac cccaaaggtt gagcgcctgt cgtctcttgt    960

acttaggaaa cctaattcct ccacccattt caagttaaca                         1000
```

<210> SEQ ID NO 57
<211> LENGTH: 1000
<212> TYPE: DNA
<213> ORGANISM: Nannochloropsis oculata

<400> SEQUENCE: 57

```
caaaaagtca taagcccaag ccgttgcgac ttctccgccg gcgaggctgc ttgatgatgc      60

tgcctgtgac tcaccatcct ctctcccggc cgatggtctc tccaccttga ctttggaccg    120

cctcgtgaag caccacctca ccctcttctt cgtgtcgctg ggtcttctgt tgtagactac    180

ttatattcac agtaatggca aggaaaaatg acacttctct ggtcagttta catccgatcc    240

tggtatggtt gtgacaaggc gagtcgcgtc gccgcttttc ttcgctcact cccggccact    300

cccagcccaa cgcacatagc aactgctgat ccaagttcca cgaccacctg caaacgtgcc    360

tgtttaagct agctcggctt gatcttttcc ttgcaatgat tacagccttg ccataaacct    420
```

```
cgttgatatc cccaaggatg catcattgac atcctaccac gccttagggt ttccttgtct    480

aggaggcaca ctgacgtgtc ccgcatggag cgatttggat caagccagca agaagaaaat    540

gaaccaaaca acgaattaga gatctgacca gcttacccaa atactgcaaa gatcattcaa    600

aaccacatag cgacgcaggg cgatggtgtc caatcaggct gtttgggtgg cttttcaact    660

cccttttctt tccttgtcct gaggcccgta gctcggcaag gagaatgtac caaaatgcgt    720

gcctgcgggg acgaatgaat cgtcacgggc cattgaccca gccaattgaa aaacagtgcc    780

gacttttggc tgaccctctc cccctccctc cctccctccc ctcactcgcc ttttcacaga    840

ggagacgaca acaccccgtt gccgcccacc tgttgtgagt agctgcccct cgcctatcct    900

ccttggtgta gacgagtcag cactttccac gccgacgcca aatcgctttc cctagagtac    960

ctatatacta gccaccaagc accccctcct atctacaatc                         1000
```

<210> SEQ ID NO 58
<211> LENGTH: 1000
<212> TYPE: DNA
<213> ORGANISM: Nannochloropsis oculata

<400> SEQUENCE: 58

```
gccctccgat aatggtacca caggcagacc acgggtcaag acgcgatact gctgcttgtc     60

gtgttgcatc gcgtcgattc gatccatcgg aggaggtggg ttgtccgtgg ctgcaggcct    120

tcaagtcttg ggtttgcgat gatctccttc tacttgctgt cttccatttt tcgttgaggg    180

ggttagaggt aaaaccacac attgtacaag ttgaagagga aagatagatg gatacaggca    240

agaagaaact caaagggtga gagccaaggc atgtagcgtg ggcctcgctt gtcaagttaa    300

acgcaagata ccactgcacc cgcgacgagc ggacgccctc aagccgaaat gacctgctgc    360

tacacaattg gcggaagtag actgcccgag ggccaagatt acggcaggga ggggaaagct    420

tgatctcgcg caacaaccga catgggaaaa aatgatgatg atggtgccgc ggcccgagaa    480

aggggtgctt cgctttggtt gctggtgaat ttaaaagcaa tggacatatg caatcgaggg    540

ggctgggaag cccgagatta gtcttttgtg ggctgcgtga gaatattgcg tagcttggac    600

ctggttccat tgcttggcat tggtgtgctg taaagtgcgt tttctctcta cagccccccgg    660

aagacatatg caaggggcac gattcagatc gtgctggcgt ggccgtcttt tgtcgagagt    720

gtaagcccct tgttgccccg cattcgatgg gctgtttggc tgggtatact gtgactaaca    780

ctacgtcaat aaggtgtggt ttggatatgt tgtggcaacg aatgtcatga gctggcgtcg    840

gacgaagcag cgcgtcggcg tgccttgtcg acattcactt actcccccac ctggctcttt    900

tgttctcgtt gcggtcgtgg tcttttaaca acaaacaata ctcacatttc ggctgcttaa    960

cacatacaca acctggatac acagggacac tccgggaagg                         1000
```

<210> SEQ ID NO 59
<211> LENGTH: 1000
<212> TYPE: DNA
<213> ORGANISM: Nannochloropsis oculata

<400> SEQUENCE: 59

```
tcgtcacccc tggtccacct gtctttgttt acgatgccaa gtggtgagta gttcaatcga     60

cgcctgtcgt tgactgcttt tcgttctctt gcttgacttt acattttcag tctgcccgca    120

cctccaagat catggtgcac cacatgatat gacatccccg ggccttagag catgatgcgt    180

cgacaatctt cgggcgagcc atcacggcaa ctagaacact tgttggtatg ggaaaagatc    240

agggagtggt gcgctgactc aagccctttt cttatttttc ttgtatgccc ctttggctat    300
```

```
gcgcagcgca ttctgcatgc acacaccacg tgcccacaca catagcaggc cttgtcatgc    360

ggcgccggag ttgttgaccg gcagcttttt cgacggcgtg cctggcctcc tcaccccact    420

cacggcgccg acgctccggg gcatacgtgg ttgtggaggg gacaccagag tgatgcagct    480

ccttagagtg tcgctgtgta cacttgtgct cttccacacg ctgtcatttc acactcattc    540

cactgtcgcg cacgcacact gaaggtctga ggcggtcgtc gcgtcacgcc tgcacccgct    600

gagaatcata acagccaggc ccttcgacac taccccatcg atcctctgcc cggccgatgg    660

gggctcgaac catgcatttt gtgggcgatt ggaacgcgtc ctttctgtcc caccgtgctc    720

ttagggaggg tgggctggtg cgtgtgacct tcacaaattc gccgtggcct tgcacgcagc    780

gaccgaggaa gagaaccttt tttggtgcgg gcgcgtgccc cacatggtac gcgcagccct    840

cacacagcca tcatcatctt aagagacaca cacttagaga catgcacgta cacaccacct    900

ctacgtactt ggcattccga agcacacact ttcctcttat atcccacccg tatctgactc    960

acccccccc tcattttcta cccatcacag acacgcaaac                          1000


<210> SEQ ID NO 60
<211> LENGTH: 475
<212> TYPE: PRT
<213> ORGANISM: Nannochloropsis oculata

<400> SEQUENCE: 60

Met Met Glu Lys Leu Thr Leu Ala Val Val Gly Ser Leu Ala Leu Thr
1               5                   10                  15

Ser Ala Phe Gln Pro Ser Ser Phe Phe Leu Arg Gln Thr Ser Ser Val
            20                  25                  30

Ser Ser Ser Ser Ser Ser Ser Arg Thr Val Arg Arg Ala Ser Gly Glu
        35                  40                  45

Val Ser Met Ala Asp Leu Pro Pro Leu Val Arg Lys Arg Val Val Ile
    50                  55                  60

Thr Gly Val Gly Ala Val Ser Pro Leu Gly Trp Gly Asp Asp Phe Trp
65                  70                  75                  80

Asn Gly Leu Val Glu Gly Arg Ser Gly Ile Val Arg Leu Pro Ser Trp
                85                  90                  95

Ala Asp Glu Tyr Pro Ala Arg Ile Gly Gly Leu Val Pro Asp His Phe
            100                 105                 110

Lys Pro Ser Asp Tyr Met Asn Ala Lys Glu Val Lys Arg Gln Ala Arg
        115                 120                 125

Phe Thr His Phe Ala Met Ala Ala Ala Arg Met Ala Val Glu Asp Ala
    130                 135                 140

Lys Leu Asp Leu Glu Lys Val Asp Arg Ser Arg Ala Gly Cys Met Ile
145                 150                 155                 160

Gly Ser Gly Ile Gly Gly Val Glu Ile Phe Glu Lys Asn Cys Gly Glu
                165                 170                 175

Phe Asp Lys Lys Gly Gly Gly Leu Pro Gly Leu Lys Ala Val Ser Pro
            180                 185                 190

Phe Leu Ile Pro Ala Leu Ile Ala Asn Thr Ala Ala Gly Thr Val Ala
        195                 200                 205

Ile Glu Leu Gly Leu Lys Gly Pro Asn Tyr Cys Ser Val Ser Ala Cys
    210                 215                 220

Ala Ser Gly Thr His Thr Ile Gly Asp Ala Phe Phe Phe Leu Gln Asn
225                 230                 235                 240

Gly Met Ala Asp Val Cys Val Thr Gly Gly Thr Glu Ala Ala Ile Thr
```

```
                245                 250                 255

Pro Leu Cys Phe Ala Gly Phe Val Ala Ile Arg Ala Leu Thr Thr Ser
            260                 265                 270

Gly Asn Asp Asp Pro Thr Lys Ala Ser Lys Pro Phe Asp Lys Asn Arg
        275                 280                 285

Ala Gly Phe Val Met Ala Glu Gly Ala Gly Met Leu Val Leu Glu Thr
    290                 295                 300

Glu Glu His Ala Lys Ala Arg Gly Ala Thr Ile Tyr Ala Glu Leu Ala
305                 310                 315                 320

Gly Tyr Gly Ala Ser Cys Asp Ala His His Ile Thr Ala Pro His Pro
                325                 330                 335

Glu Gly Glu Gly Leu Ala Asn Ala Met Asn Met Ala Leu Thr Ser Ala
            340                 345                 350

Gly Leu Lys Pro Thr Asp Val Asp Tyr Ile Asn Ala His Gly Thr Ser
        355                 360                 365

Thr Ala Tyr Asn Asp Lys Phe Glu Thr Leu Ala Ile His Arg Val Phe
    370                 375                 380

Gly Glu His Ala Lys Lys Leu Lys Val Ser Ser Ile Lys Ser Met Thr
385                 390                 395                 400

Gly His Ser Leu Gly Ala Ala Gly Ala Phe Glu Ala Val Ala Cys Ala
                405                 410                 415

Lys Ala Ile Lys Glu Gly Ile Ile Pro Pro Thr Ile Asn Tyr Glu Thr
            420                 425                 430

Pro Asp Pro Asp Cys Asp Leu Asp Tyr Val Pro Asn Lys Ala Ile Lys
        435                 440                 445

His Asp Val Asn Val Ala Ile Ser Asp Asn Leu Gly Phe Gly Gly His
    450                 455                 460

Asn Ala Ala Leu Val Phe Lys Lys Tyr Val Ala
465                 470                 475


<210> SEQ ID NO 61
<211> LENGTH: 1428
<212> TYPE: DNA
<213> ORGANISM: Nannochloropsis oculata

<400> SEQUENCE: 61

atgatggaga agctgaccct cgcagtggtg ggctcccttg ccctgacttc ggccttccag     60

ccctcgtcct tcttcctccg gcagacttcc tccgtcagca gcagcagcag cagcagcagg    120

actgtgcgtc gtgcatcagg ggaagtgagc atggcggact tgccccccgct tgtccgcaag    180

agggtggtga tcacgggtgt cggcgccgtg tctcctctcg ggtggggaga cgacttctgg    240

aacggtctcg tggagggaag gagcggcatt gtccgcctcc cttcgtgggc ggacgagtac    300

cccgcgcgaa tcggaggctt ggtcccggat cactttaagc cgagcgacta catgaatgcc    360

aaggaggtga aacgacaggc ccgcttcacc cattttgcca tggcagctgc ccgtatggcc    420

gtggaagacg ccaagctcga cctggagaag gtggaccgct cgcgtgccgg gtgcatgata    480

ggatccggca ttggtggtgt agaaatcttc gagaaaaact gtggggaatt cgacaagaag    540

ggcggagggc tccctggcct caaggctgtc tccccccttcc tgattccggc cctcatcgcc    600

aacaccgcag ccgggacagt ggctattgaa ctcggcttga agggcccgaa ctactgctct    660

gtctccgcct gcgcctcggg cacgcatacc atcggtgatg ccttcttctt cctccaaaac    720

ggcatggcgg acgtttgtgt aacgggcggg acggaagccg ccatcacccc cctctgtttt    780

gcgggatttg tcgccattcg cgcccttacc accagtggca acgacgaccc caccaaggcc    840
```

```
tccaagccgt tcgacaagaa ccgagccggt ttcgttatgg ccgagggagc ggggatgctc    900

gtccttgaga cggaggaaca cgcgaaggcc cgaggtgcca ccatctatgc cgagcttgct    960

ggctacggcg catcctgcga cgcccaccac atcaccgccc cccatcccga aggcgagggg   1020

ctggcgaacg cgatgaatat ggctctgacg tccgccggcc tcaagcctac ggacgtggac   1080

tacattaatg cccatggaac cagcacggcc tacaacgaca aattcgagac gctggccatt   1140

caccgcgtct ttggcgagca cgccaagaag ctgaaggttt cttccatcaa gtcaatgact   1200

ggtcactccc tcggggccgc cggtgccttc gaggccgtgg cgtgcgcgaa ggcaatcaag   1260

gagggcatca tcccgcccac catcaactac gagactcccg atccagactg cgacttggac   1320

tatgttccca acaaggcgat caagcacgac gtgaatgtgg ccatctccga taacctgggc   1380

ttcggcgggc acaacgcggc tttggtcttc aagaagtatg ttgcctag                1428


<210> SEQ ID NO 62
<211> LENGTH: 146
<212> TYPE: PRT
<213> ORGANISM: Nannochloropsis oculata

<400> SEQUENCE: 62

Met Ala Leu Arg Gln Phe Leu Lys Leu Ala Ser Ser Ala Ala Arg Ser
1               5                   10                  15

Gln Ala Gln Gln Arg Gly Ile Met Thr Val Ala Arg Arg Gly Thr Pro
            20                  25                  30

Ala Leu Val Thr Ala Met Arg Gln Gln Gln Ala Leu Leu Ala Arg Pro
        35                  40                  45

Val Val Gly Gly Leu Ser Ser Arg Asn Phe Gly Asn Ala Gln Thr Phe
    50                  55                  60

Leu Asp Glu Lys Glu Val Ala Asp Arg Val Leu Gln Val Val Lys Asn
65                  70                  75                  80

Phe Glu Lys Val Glu Pro Gly Lys Val Thr Ala Ala Ala Arg Phe Lys
                85                  90                  95

Glu Asp Leu Ser Leu Asp Ser Leu Asp Val Val Glu Val Val Met Ala
            100                 105                 110

Ile Glu Glu Glu Phe Ala Leu Glu Ile Pro Asp Asn Glu Ala Asp Lys
        115                 120                 125

Ile Ala Ser Ile Gly Asp Ala Ile Lys Tyr Ile Thr Ser His Pro Gln
    130                 135                 140

Ala Lys
145


<210> SEQ ID NO 63
<211> LENGTH: 441
<212> TYPE: DNA
<213> ORGANISM: Nannochloropsis oculata

<400> SEQUENCE: 63

atggctctcc gtcaatttct gaagctggca tctagtgccg cccgctccca ggcacagcaa     60

cgggggatca tgacagtcgc tcgtcgaggg acgcctgcct tggtgacggc catgcggcag    120

caacaggcgc ttttagcccg gcctgtggtg gggggtttga gcagccggaa ctttggcaat    180

gcgcagacgt ttctggacga gaaggaggtg gcggaccgcg ttctccaagt ggtgaagaat    240

tttgagaagg tggagcccgg gaaggtgacg gccgccgccc gcttcaagga ggatctctcc    300

ctggactcct tggacgtggt ggaggtggta atggcgatcg aggaagaatt tgcgttggag    360
```

```
attccagaca acgaggcaga taagattgct tccattggtg atgccattaa atatatcaca    420

tcccatcccc aggcaaaata a                                              441


<210> SEQ ID NO 64
<211> LENGTH: 274
<212> TYPE: PRT
<213> ORGANISM: Nannochloropsis gaditana

<400> SEQUENCE: 64

Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser


<210> SEQ ID NO 65
<211> LENGTH: 287
<212> TYPE: PRT
<213> ORGANISM: Nannochloropsis oculata

<400> SEQUENCE: 65

Met Thr Pro Leu Ala Phe Thr Val Leu Gly Lys Leu Gly Gly Thr Leu
1               5                   10                  15

Thr Phe Ala Cys Val Arg Arg Arg Leu Tyr His Leu Leu Arg Arg Ala
            20                  25                  30
```

```
Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285


<210> SEQ ID NO 66
<211> LENGTH: 285
<212> TYPE: PRT
<213> ORGANISM: Nannochloropsis granulata

<400> SEQUENCE: 66

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125
```

```
Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285


<210> SEQ ID NO 67
<211> LENGTH: 348
<212> TYPE: PRT
<213> ORGANISM: Nannochloropsis oculata

<400> SEQUENCE: 67

Met Arg Ile Pro Ser Leu Ile Leu Cys Phe Ala Phe Leu Ala Ser Ala
1               5                   10                  15

Pro Ala Val Ala Phe Leu Leu Pro Pro Leu Pro Cys Phe Ser Ser Ser
            20                  25                  30

Leu Gln Thr Val Thr Asn Thr Ile Thr Thr Ser Ser Arg Phe Ser Ser
        35                  40                  45

Ser Ser Ser Ser Ser Ser Ser Ser Ser Ser Ser Ser Ser Arg Pro Arg
    50                  55                  60

Cys Ser Pro Leu Leu Ser Val Thr Thr Ala Ala Thr Ala Ser Ser Ala
65                  70                  75                  80

Thr Glu Glu Ala Glu Asn Pro Ser Leu Thr Gln Gly Val Phe Ile Glu
                85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
    130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Glu Ala Leu Arg Lys Val
        195                 200                 205

Val Ala Ser Pro Asp Lys Val Met Glu Ala Val Leu Trp Thr Asp Glu
```

```
    210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
                245                 250                 255

Leu Met Asp Asp Gly Tyr Met Phe Val Val Ala Arg Ile Asp Gly Tyr
            260                 265                 270

Arg Phe Asp Pro Ser Leu Arg Leu Glu Glu Gly Glu Ala Leu Gln Val
        275                 280                 285

Leu Gly Arg Phe Lys Pro Lys Ser Asp Ala Ile Val Val Cys Glu Gln
    290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Lys Leu Arg Gly Val Pro
                325                 330                 335

Ser Lys Ala Leu Glu Ser Met Asn Met Gly Thr Thr
            340                 345
```

<210> SEQ ID NO 68
<211> LENGTH: 552
<212> TYPE: DNA
<213> ORGANISM: Artificial Sequence
<220> FEATURE:
<223> OTHER INFORMATION: Bialaphos resistance gene

<400> SEQUENCE: 68

```
atgagcccag aacgacgccc ggccgacatc cgccgtgcca ccgaggcgga catgccggcg     60

gtctgcacca tcgtcaacca ctacatcgag acaagcacgg tcaacttccg taccgagccg    120

caggaaccgc aggagtggac ggacgacctc gtccgtctgc gggagcgcta tccctggctc    180

gtcgccgagg tggacggcga ggtcgccggc atcgcctacg cgggcccctg gaaggcacgc    240

aacgcctacg actggacggc cgagtcgacc gtgtacgtct ccccccgcca ccagcggacg    300

ggactgggct ccacgctcta cacccacctg ctgaagtccc tggaggcaca gggcttcaag    360

agcgtggtcg ctgtcatcgg gctgcccaac gacccgagcg tgcgcatgca cgaggcgctc    420

ggatatgccc cccgcggcat gctgcgggcg gccggcttca agcacgggaa ctggcatgac    480

gtgggtttct ggcagctgga cttcagcctg ccggtaccgc cccgtccggt cctgcccgtc    540

accgagatct ga                                                        552
```

<210> SEQ ID NO 69
<211> LENGTH: 35
<212> TYPE: DNA
<213> ORGANISM: Artificial Sequence
<220> FEATURE:
<223> OTHER INFORMATION: primer No. 69

<400> SEQUENCE: 69

```
ctttttgtg aagcaatgag cccagaacga cgccc                                 35
```

<210> SEQ ID NO 70
<211> LENGTH: 37
<212> TYPE: DNA
<213> ORGANISM: Artificial Sequence
<220> FEATURE:
<223> OTHER INFORMATION: primer No. 70

<400> SEQUENCE: 70

```
tttcccccat cccgatcaga tctcggtgac gggcagg                              37
```

<210> SEQ ID NO 71
<211> LENGTH: 37
<212> TYPE: DNA
<213> ORGANISM: Artificial Sequence
<220> FEATURE:
<223> OTHER INFORMATION: primer No. 71

<400> SEQUENCE: 71
cagcccgcat caacaatggc cgccgccctt cttgcag 37

<210> SEQ ID NO 72
<211> LENGTH: 36
<212> TYPE: DNA
<213> ORGANISM: Artificial Sequence
<220> FEATURE:
<223> OTHER INFORMATION: primer No. 72

<400> SEQUENCE: 72
ctcttccaca gaagcttaag ccttcttgga aaccgg 36

<210> SEQ ID NO 73
<211> LENGTH: 831
<212> TYPE: DNA
<213> ORGANISM: Nannochloropsis oculata

<400> SEQUENCE: 73
atggccgccg cccttcttgc agactatcaa aaaacctgca cggacttgtc cgccgccatt 60
tttaagtggg ctgaccctgc gggcgccatg gtcaaggcgc ccactcgcac ctggcccttg 120
gcgggtttgg acgtggccct ggctatcgcg gctttctacc tcatcattgt ctttgtgggt 180
tcggccatga tgaagaacgc aaagccagta aaattgtacg gcttgcaatt cttctacaac 240
atctcccagg tcgccctatg ctcctatatg tgcatcgagg ctgccattca ggcctaccgt 300
aacaactaca ccttcctccc ttgcgagccg ttcaatgcta ccaacccacc aatcgcccct 360
ctcctgtggc tcttctacgt ctccaaggtc ttcgacttcg ccgacaccgt cttcatcatc 420
ctgggaaaga agtggaacca gctatcattt ctgcatgtgt accaccacgt gaccatcttt 480
ttggtgtatt ggttgaattt gaatgcggga tatgatggcg atattttcct gacagtcatt 540
cttaacgggg caatccacac ggtaatgtac acttactact tcctctccat gcacaccaag 600
gacatttggt ggaagaagta cttgacactg ttccagatta ttcagttcct gaccatgaat 660
gctcaggcga tctacttgtt atgtgtgggt tgcaaggggt tctcgcctca gattacgaag 720
ctgtatcttg ggtacatcct gtcgctgttg gtgcttttcc tcaattttta cttcaaatcg 780
tattctggtg tgaagcccaa tggtaagaag ccggtttcca agaaggctta a 831

<210> SEQ ID NO 74
<211> LENGTH: 276
<212> TYPE: PRT
<213> ORGANISM: Nannochloropsis oculata

<400> SEQUENCE: 74

Met Ala Ala Ala Leu Leu Ala Asp Tyr Gln Lys Thr Cys Thr Asp Leu
1 5 10 15

Ser Ala Ala Ile Phe Lys Trp Ala Asp Pro Ala Gly Ala Met Val Lys
20 25 30

Ala Pro Thr Arg Thr Trp Pro Leu Ala Gly Leu Asp Val Ala Leu Ala
35 40 45

Ile Ala Ala Phe Tyr Leu Ile Ile Val Phe Val Gly Ser Ala Met Met

```
    50                  55                  60

Lys Asn Ala Lys Pro Val Lys Leu Tyr Gly Leu Gln Phe Phe Tyr Asn
65                  70                  75                  80

Ile Ser Gln Val Ala Leu Cys Ser Tyr Met Cys Ile Glu Ala Ala Ile
                85                  90                  95

Gln Ala Tyr Arg Asn Asn Tyr Thr Phe Leu Pro Cys Glu Pro Phe Asn
            100                 105                 110

Ala Thr Asn Pro Pro Ile Ala Pro Leu Leu Trp Leu Phe Tyr Val Ser
        115                 120                 125

Lys Val Phe Asp Phe Ala Asp Thr Val Phe Ile Ile Leu Gly Lys Lys
    130                 135                 140

Trp Asn Gln Leu Ser Phe Leu His Val Tyr His His Val Thr Ile Phe
145                 150                 155                 160

Leu Val Tyr Trp Leu Asn Leu Asn Ala Gly Tyr Asp Gly Asp Ile Phe
                165                 170                 175

Leu Thr Val Ile Leu Asn Gly Ala Ile His Thr Val Met Tyr Thr Tyr
            180                 185                 190

Tyr Phe Leu Ser Met His Thr Lys Asp Ile Trp Trp Lys Lys Tyr Leu
        195                 200                 205

Thr Leu Phe Gln Ile Ile Gln Phe Leu Thr Met Asn Ala Gln Ala Ile
    210                 215                 220

Tyr Leu Leu Cys Val Gly Cys Lys Gly Phe Ser Pro Gln Ile Thr Lys
225                 230                 235                 240

Leu Tyr Leu Gly Tyr Ile Leu Ser Leu Leu Val Leu Phe Leu Asn Phe
                245                 250                 255

Tyr Phe Lys Ser Tyr Ser Gly Val Lys Pro Asn Gly Lys Lys Pro Val
            260                 265                 270

Ser Lys Lys Ala
        275


<210> SEQ ID NO 75
<211> LENGTH: 1000
<212> TYPE: DNA
<213> ORGANISM: Nannochloropsis oculata

<400> SEQUENCE: 75

ggcgagggtg ataaagggtg cgatgaggga tgttttgata tgggtgcgtt ccagtgagtt      60

gccggaacag gcgacgtatc ctcatttggc tccgttgtgt gtgtatgcga cggcggggat     120

agggtatgag gaagaaacgg cggacgatgg agaggatgag gaaggggagg aagagaacga     180

ggagctggat gagcagcagg agcagcagga ggaagggcag gagatggtat tgtaacggac     240

gagtcagaca atcatttctc atacataacc aagactgcga gagcagcaat gaagcaaacc     300

aagtaatttg gcatttttat catatttgta tatttgatat acatatgtat atgagtggtg     360

gagtacagcg cgtgcacgca aaaagctcgt acacgatcca agcacgatcc aaacacgacc     420

acaacctaaa atatagcccg accgaaagca aatcgaaatg acccttggtt tatttaacat     480

ggtagttgaa agaaactgac tccaagaaga aagtacacta aatgaatggg cccatggtgc     540

tattgctgta gctaacgctg cttgatggac ggacggcgag cgacgggttg ttgatgcttc     600

actccctctg gagcccccac cttcattagg taatctccac attgcttcct ttgctatcta     660

tgccacaagc ctctagataa ctcgcgaaga tgctggcggg gattggaccg cgtcgtaacc     720

ctggcttgcc caccaccatt cgtacgtcat tcatcccttt ccacctcaag caagaggccc     780

aatccatttt actgccccat gccaagggcg gcatgtactg gagttgtctc acgttacatg     840
```

-continued

```
catcatgcga cccgcgcaaa ccaggcacaa ttgttatagt tttgatcggc tcctcctcgc    900

atagagtatc ttatctcctc tcccaaccat ctcaccactc tccctcatcc tcaacacata    960

tcaggcagcc ctcacttgtc ccatcaccat aaaaagcatc                         1000
```